(12) United States Patent
Kostenuik et al.

(10) Patent No.: US 6,756,480 B2
(45) Date of Patent: Jun. 29, 2004

(54) MODULATORS OF RECEPTORS FOR PARATHYROID HORMONE AND PARATHYROID HORMONE-RELATED PROTEIN

(75) Inventors: Paul Kostenuik, Newbury Park, CA (US); Chuan-Fa Liu, Longmont, CO (US); David Lee Lacey, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/843,221

(22) Filed: Apr. 26, 2001

(65) Prior Publication Data

US 2003/0039654 A1 Feb. 27, 2003

Related U.S. Application Data

(60) Provisional application No. 60/266,673, filed on Feb. 6, 2001, provisional application No. 60/214,860, filed on Jun. 28, 2000, and provisional application No. 60/200,053, filed on Apr. 27, 2000.

(51) Int. Cl.[7] .......................... C07K 16/00; A61K 39/00
(52) U.S. Cl. ................. 530/387.1; 424/130.1; 424/178.1
(58) Field of Search .................. 530/300, 350, 530/387.1; 424/130.1, 178.1; 514/2

(56) References Cited

U.S. PATENT DOCUMENTS

| | | |
|---|---|---|
| 4,423,037 A | 12/1983 | Rosenblatt et al. |
| 4,656,250 A | 4/1987 | Morita et al. |
| 4,968,669 A | 11/1990 | Rosenblatt et al. |
| 5,087,562 A | 2/1992 | Rosenblatt et al. |
| 5,118,667 A | 6/1992 | Adams et al. |
| 5,171,670 A | 12/1992 | Kronenberg et al. |
| 5,393,869 A * | 2/1995 | Nakagawa et al. ......... 530/324 |
| 5,434,246 A | 7/1995 | Fukuda et al. |
| 5,494,806 A | 2/1996 | Segre et al. |
| 5,529,915 A | 6/1996 | Phillips et al. |
| 5,556,940 A * | 9/1996 | Willick et al. ............... 530/317 |
| 5,589,452 A * | 12/1996 | Krstenansky et al. ......... 514/12 |
| 5,599,792 A | 2/1997 | Kronis et al. |
| 5,599,822 A | 2/1997 | Cullinan et al. |
| 5,670,514 A | 9/1997 | Audia et al. |
| 5,693,616 A * | 12/1997 | Krstenansky et al. ......... 514/12 |
| 5,723,577 A | 3/1998 | Dong |
| 5,807,823 A | 9/1998 | Krstenansky et al. |
| 5,840,853 A | 11/1998 | Segre et al. |
| 5,874,086 A | 2/1999 | Krstenansky et al. |
| 5,886,148 A | 3/1999 | Segre et al. |
| 5,955,574 A | 9/1999 | Dong |
| 5,969,095 A | 10/1999 | Dong |
| 6,147,186 A | 11/2000 | Gardella et al. |
| 6,242,495 B1 | 6/2001 | Leone-Bay et al. |
| 6,417,333 B1 | 7/2002 | Bringhurst et al. |

FOREIGN PATENT DOCUMENTS

| | | |
|---|---|---|
| EP | 0 483 509 | 5/1992 |
| EP | 0 526 452 | 2/2001 |
| WO | WO 94/01460 | 1/1994 |
| WO | WO 99/06535 | 2/1999 |
| WO | WO 99/38535 | 8/1999 |
| WO | WO 99/38536 | 8/1999 |
| WO | WO 99/46283 | 9/1999 |
| WO | WO 99/52933 | 10/1999 |
| WO | WO 00/04047 | 1/2000 |
| WO | WO 00/13651 | 3/2000 |
| WO | WO 00/19823 | 4/2000 |
| WO | WO 00/23594 | 4/2000 |
| WO | WO 00/31137 | 6/2000 |
| WO | WO 00/40611 | 7/2000 |
| WO | WO 00/50633 | 8/2000 |
| WO | WO 00/77042 | 12/2000 |
| WO | WO 01/08673 | 2/2001 |
| WO | WO 01/23427 | 4/2001 |
| WO | WO 01/23521 | 4/2001 |

OTHER PUBLICATIONS

Hill, et al. (1997), "Multiple Extracellular Signals Promote Osteoblast Survival and Apoptosis," *Endocrinology* 138(9):3849–3858.
Barbier et al. (1997), "Bioactivities and Secondary Structures of Constrained Analogues of Human Parathyroid Hormone: Cyclic Lactams of the Receptor Binding Region", *J. Med. Chem.* 40:1373–1380.
Bergeron et al. (1981), "In Vivo Demonstration of Receptors in Rat Liver to the Amino–Terminal Region of Parathyroid Hormone", *Endocrinology* 109(5):1552–1559.
Coltrera et al. (1981), "Identification of a Renal Receptor for Parathyroid Hormone by Photoaffinity Radiolabeling Using a Synthetic Analogue", *The Journal of Biological Chemistry* 256(20):10555–10559.

(List continued on next page.)

*Primary Examiner*—Gary Kunz
*Assistant Examiner*—Christopher James Nichols
(74) *Attorney, Agent, or Firm*—Robert B. Winter; Stuart L. Watt

(57) ABSTRACT

The present invention concerns therapeutic agents that modulate the activity of PTH and PTHrP. In accordance with the present invention, modulators of PTH and PTHrP comprise:
(a) a PTH/PTHrP modulating domain; and
(b) a vehicle, such as a polymer (e.g., PEG or dextran) or an Fc domain, which is preferred;
wherein the vehicle is covalently attached to the C-terminus of the PTH/PTHrP modulating domain. The vehicle and the PTH/PTHrP modulating domain may be linked through the N- or C-terminus of the PTH/PTHrP modulating domain, as described further below. The preferred vehicle is an Fc domain, and the preferred Fc domain is an IgG Fc domain. Preferred PTH/PTHrP modulating domains comprise the PTH and PTHrP-derived amino acid sequences described hereinafter. Other PTH/PTHrP modulating domains can be generated by phage display, RNA-peptide screening and the other techniques mentioned herein. Such peptides typically will be modulators of both PTH activity and PTHrP activity, although such techniques can be used to generate peptide sequences that serve as selective modulators (e.g., agonists of PTH activity but not PTHrP activity).

24 Claims, 15 Drawing Sheets

OTHER PUBLICATIONS

Dobnig et al. (1997), "The Effects of Programmed Administration of Human Parathyroid Hormone Fragment (1–34) on Bone Histomorphometry and Serum Chemistry in Rats," *Endocrinology* 138(11):4607–4612.

Doppelt et al. (1981), "Human Parathyroid Hormone 1–34–Mediated Hypercalcemia in a Rat Model, and Its Inhibition by Dichloromethane Diphosphonate", *Calcif. Tissue Int.* 33:649–654.

Dresner–Pollak et al. (1996), "Evaluation In Vivo of a Poatent Parathyroid Hormone Antagonist:[Nle$^{8,18}$, D–Trp$^{12}$, Tyr$^{34}$]bPTH(7–34)NH$^{2}$"; *Journal of Bone and Mineral Research* 11:1061–1065.

Fenton et al. (1991), "A Carboxyl–Terminal Peptide from the Parathyroid Hormone–Related Protein Inhibits Bone Resorption by Osteoclasts", *Endocrinology* 129(4):1762–1768.

Fenton et al. (1991), "A Potent Inhibitor of Osteoclastic Bone Resorption within a Highly Conserved Pentapeptide Region of Parathyroid Hormone–Related Protein; PTHrP [107–111]" *Endocrinology* 129(6):3424–3426.

Fukayama et al. (1998), "New insights into interactions between the human PTH/PTHrP receptor and agonist/antagonist binding", *American Journal of Physiological* 274:E297–E303.

Gardella et al. (1996), "Converting Parathyroid Hormone–related Peptide (PTHrP) into a Potent PTH–2 Receptor Agonist", *The Journal of Biological Chemistry* 271(33):19888–19893.

Gardella et al. (1996), "Inverse Agonism of Amino–Terminally Truncated Parathyroid Hormone (PTH) and PTH–Related (PTHrP) Analogs Revealed with Constitutively Active Mutant PTH/PTHrP Receptors", *Endocrinology* 137(9):3936–3941.

Goldman et al. (1988), "A New Highly Potent Parathyroid Hormone Antagonist: [D–TRP$^{12}$, TYR$^{34}$]bPTH–(7—34)NH$_2$", *Endocrinology* 123(5):2597–2599.

Gray et al. (1982), "In Vivo Studies on an Antagonist of Parathyroid Hormone [Nle–8, Nle–18, Tyr–34] bPTH–(3–34) Amide", *Br. J. Pharmac.* 76:259–263.

Heinrich et al. (1984), "Gene Encoding Parathyroid Hormone" *The Journal of Biological Chemistry* 259(5):3320–3329.

Hendy et al. (1981), "Nucleotide sequence of cloned cDNAs encoding human preproparathyroid hormone", *Proc. Natl. Acad. Sci. USA* 78(12):7365–7369.

Holick et al. (1994), "A parathyroid hormone antagonist, stimulates epidermal proliferation and hair growth in mice", *Proc. Natl. Acad. Sci. USA* 91:8014–8016.

Holick et al. (1995), "A PTHrP Antagonist Stimulates Epidermal Proliferation, and Hair Growth, and Regulates the Hair Cycle. A New Insight into the Biologic Function of PTHrP in the Skin", *Bone* 16:140S.

Horiuchi et al. (1983), "A Parathyroid Hormone Inhibitor in vivo: Design and Biological Evaluation of a Hormone Analog", *Science* 220:1053–1055.

Huang et al. (1999), "Role of Signal Transduction in Internalization of the G Protein–Coupled Receptor for Parathyroid Hormone (PTH) and PTH–Related Protein", *Endocrinology* 140(3):1294–1300.

Jobert et al. (1997), "Parathyroid Hormone–Induced Calcium Release from Intracellular Stores in a Human Kidney Cell Line in the Absence of Stimulation of Cyclic Adenosine 3', 5'–Monophosphate Production", *Endocrinology* 138(12):5282–5292.

Jouishomme et al. (1994), "Further Definition of the Protein Kinase C Activation Domain of the Parathyroid Hormone" *Journal of Bone and Mineral Research* 9:943–949.

Kemp et al. (1987), "Parathyroid Hormone–Related Protein of Malignancy: Active Synthetic Fragments", *Science* 238:1568–1570.

Kent et al. (1985), "Pharmacokinetics of synthetic human parathyroid hormone 1–34 in man measured by cytochemical bioassay and radioimmunoassay", *Clinical Science* 68:171–177.

Kimura et al. (1983), "Solution Synthesis of [ASN$^{76}$]–Human Parathyroid Hormone (1–84)", *Biochemical and Biophysical Research Communications* 114(2):493–499.

Law et al. (1983), "Preparation of Synthetic Bovine Parathyroid Hormone Fragment 1–34 for Parenteral Use in Human Studies", *Journal of Clinical Endocrinology and Metabolism* 56(6):1335–1337.

Lee, et al. (1989), "Two–Dimensional $^1$H–NMR Study of the 1–34 Fragment of Human Parathyroid Hormone," *Biopolymers* 28:1115–1127.

Li, et al. (1996), "Human Chorionic Gonadotropin Down–Regulates the Expression of Gonadotropin–Releasing Hormone Receptor Gene in GT1–7 Neurons," *Endocrinology* 137(3):899–904.

Li, et al. (1996), "Detection of Extended Distribution of $\beta_2$Thyroid Hormone Receptor Messenger Ribonucleic Acid (RNA) in Adult Rat Brain Using Complementary RNA in Situ Hybridization Histochemistry," *Endocrinology* 137(4):1272–1275.

Li, et al. (1996), "The Ontogeny of Hepatic Growth Hormone Receptor and Insulin–Like Growth Factor I Gene Expression in the Sheep Fetus during Late Gestation: Developmental Regulation by Cortisol," *Endocrinology* 137(5):1650–1657.

Li, et al. (1996), "An Oviposition–Inducing Peptide: Isolation, Localization, and Function of Avian Galanin in the Quail Oviduct," *Endocrinology* 137(5):1618–1626.

Li, et al. (1996), "Regulation of Hen Granulosa Cell Prostaglandin Production by Transforming Growth Factors during Follicular Development: Involvement of Cyclooxygenase II," *Endocrinology* 137(6):2522–2529.

Li, et al. (1996), "Effect of Endogenously Produced Parathyroid Hormone–Related Peptide on Growth of a Human Hepatoma Cell Line (Hep G2)," *Endocrinology* 137(6):2367–2374.

Lowik et al. (1985), "A Two–Receptor Model for the Action of Parathyroid Hormone on Osteoblasts: A Role for Intracellular Free Calcium and cAMP", *Cell Calcium* 6:311–326.

Mannstadt et al. (1999), "Receptors for PTH and PTHrP: their biological important and functional properties",*American Journal of Physiological* 277:F665–F675.

McGowan et al. (1983), "Parathyroid Hormone: Effects of the 3–34 Fragment in vivo and in vitro", *Science* 219:67–69.

McKee et al. (1989), "Synthetic Peptides as Tools for Investigating the Pathogenicity of Disease: Humoral Hypercalcemia of Malignancy", *Peptide Research* 2(2):161–166.

Moseley et al. (1987), "Parathyroid hormone–related protein purified from a human lung cancer cell line", *Proc. Natl. Acad. Sci. USA* 84:5048–5052.

Nagasaki et al. (1989), "In vitro and in vivo antagonists against parathyroid hormone–related protein", *Biochemical and Biophysical Research Communications* 158(3):1036–1042.

Nakabayashi et al. (1987), "Role of Protein Kinase C in the Regulation of Rat Liver Glycogen Synthase" *Archives of Biochemistry and Biophysics* 252(1):81–90.

Nakamura et al. (1981), "Acute Hypotensive Action of Parathyroid Hormone–(1–34) Fragments in Hypertensive Rats", *Proc. Soc. Exp. Biol. Med.* 168:168–171.

Neugebauer et al. (1994), "Structure and protein kinase C stimulating activities of lactam analogues of human parathyroid hormone fragment", *Int. J. Peptide Protein Res.* 43:555–562.

Nussbaum et al. (1980), "Parathyroid Hormone—Renal Receptor Interactions", *The Journal of Biological Chemistry* 255(21):10183–10187.

Nutt et al. (1990), "Removal of Partial agonism from Parathyroid Hormone (PTH)–Related Protein (7–34)$NH_2$ by Substitution of PTH Amino Acids at Positions 10 and 11", *Endocrinology* 127(1):491–493.

Paspaliaris et al. (1995), "Daily Administration of PTHrP(1–34) Inhibits the Raid Decline in Osteoblast Marker mRNA Levels and Bone Formation in Rat Tibia Following Denervation", *Bone* 16:141S.

Podbesek et al. (1983), "Effects of Two Treatment Regimes with Synthetic Human Parathyroid Hormone Fragment on Bone Formation and the Tissue Balance of Trabecular Bone in Greyhounds" *Endocrinology* 112(3):1000–1006.

Reeve et al. (1990), "Treatment of osteoporosis with human parathyroid peptide and observations on effect of sodium fluoride", *Br. Med. J.* 301:314–318.

Rosenblatt et al. (1977), "Parathyroid Hormone Inhibitors", *The Journal of Biological Chemistry* 252(16):5847–5851.

Scharla et al. (1989), "Osteolytic Activity of Walker Carcinosarcoma 256 is Due to Parathyroid Hormone–Related Protein (PTHrP)", *Horm. Metab. Res.* 23:66–69.

Schipani et al. (1993), "Identical Complementary Deoxyribonucleic Acids Encode a Human Renal and Bone Parathyroid Hormone (PTH)/PTH–Related Peptide Receptor", *Endocrinology* 132(5):2157–2165.

Segre et al. (1979), "Characterization of Parathyroid Hormone Receptors in Canine Renal Cortical Plasma Membranes Using a Radioiodinated Sulfur–free Hormone Analogue", *The Journal of Biological Chemistry* 254(15):6980–6986.

Sham et al. (1986), "Comparative Study on the Cardiac Actions of Bovine Parathyroid Hormone (1–34)", *General and Comparative Endocrinology* 61:148–152.

Suva et al. (1987), "A Parathyroid Hormone–Related Protein Implicated in Malignant Hypercalcemia: Cloning and Expression", *Science* 237:893–896.

Usdin, et al. (1999), "TIP39: a new neuropeptide and PTH2–receptor agonist from hypothalamus," *Nature* 2(11):941–943.

Usdin, et al. (1996), "Distribution of Parathyroid Hormone–2 Receptor Messenger Ribonucleic Acid in Rat," *Endocrinology* 137(10):4285–4297.

Usdin, et al. (1995), "Identification and Functional Expression of a Receptor Selectively Recognizing Parathyroid Hormone, the PTH2 Receptor," *J. of Biol. Chem.* 270(26):15455–15458.

Usdin, et al. (1999), "Distribution of Parathyroid Hormone 2 Receptor in Rat: Immunolocalization Reveals Expression by Several Endocrine Cells," *Endocrinology* 140(7):3363–3371.

Wang et al. (1984), "Effects of Synthetic Parathyroid Hormone on Hemodynamics and Regional Blood Flows", *European Journal of Pharmacology* 97:209–215.

Whitfield et al. (1994), "C–Terminal Fragments of Parathyroid Hormone–Related Protein, PTHrP–(107–111) and (107–139), and the N–Terminal PTHrP–(1–40) Fragment Stimulate Membrane–Associated Protein Kinase C Activity in Rat Spleen Lymphocytes", *Journal of Cellular Physiology* 158:518–522.

Whitfield et al. (1995), "Small bone–building fragments of parathyroid hormone: new therapeutic agents for osteoporosis", *TIPS* 16:382–386.

Williams et al. (1998), "Effect of antagonism of the parathyroid hormone (PTH)/PTH–related protein receptor on decidualization in rat uterus", *Journal of Reproduction and Fertility* 112:59–67.

Wingender et al. (1989), "Expression of Human Parathyroid Hormone in *Escherichia coli*", *The Journal of Biological Chemistry* 264(8):4367–4373.

Yasuda et al. (1989), "Characterization of the Human Parathyroid Hormone–like Peptide Gene", *The Journal of Biological Chemistry* 264(13):7720–7725.

Zanelli et al. (1985), "Biological Activities of Synthetic Human Parathyroid Hormone (PTH) 1–84 Relative to Natural Bovine 1–84 PTH in Two Different in Vivo Bioassay Systems" *Endocrinology* 117(5):1962–1967.

Schilli et al. (1997), "Control of Hair Growth with Parathyroid Hormone (7–34)", *Journal of Investigative Dermatology* 108:928–932.

Cottingham, et al. (2001), "A method for the amidation of recombinant peptides expressed as intein fusion proteins in *Escherichia coli*," *Nature Biotechnology* 19:974–977.

Baumann et al., Response of Cortical Bone to Antiresorptive Agents and Parathyroid Hormone in Aged Ovariectomized Rats. BONE, 16(6): 247–253. (Feb. 1995).

Berning et al., Tibolone and its effects on bone: a review. CLIMACTERIC, 4(2):120–136. (Jun. 2001).

Crandall, C., Parathyroid Hormone for Treatment of Osteoporosis. Archives of Internal Medicine, 162:2297–2309. (Nov. 11, 2002).

Hodsman, A. B. et al., Biochemical responses to sequential human parathyroid hormone (1–38) and calcitonin in osteoporotic patients. Bone and Mineral., 9(2): 137–152. (May 1990).

Hofbauer, L. C. et al., Stimulation of Osteoprotegerin Ligand and Inhibition of Osteoprotegerin Production by Glucocorticoids in Human Osteoblastic Lineage Cells: Potential Paracrine Mechanisms of Glucocorticoid–Induced Osteoporosis. ENDOCRINOLOGY, 140(10): 4382–4389. (Oct. 1999).

Kostenuik, P. J. et al., OPG and PTH(1–34) Have Additive Effects on Bone Density and Mechanical Strength in Osteopenic Ovariectomized Rats. ENDOCRINOLOGY, 142(10): 4295–4304. (Oct. 2001).

Li, M. et al., Parathyroid Hormone Monotherapy and cotherapy with Antiresorptive Agents Restore Vertebral Bone Mass and Strength in Aged Ovariectomized Rates. BONE, 16(6): 629–635. (Jun. 1995).

Morley, P. et al., Parathyroid Hormone: An Anabolic Treatment for Osteoporosis. Current Pharmaceutical Design, 7(8): 671–687. (May 2001).

Reeve, J. et al., Treatment with parathyroid peptides and estrogen replacement for severe postmenopausal vertebral osteoporosis: prediction of long–term responses in spine and femur. J. Bone Minr. Metab., 19(2): 102–114. (Mar. 9, 2001).

Rosen et al., Clinical Review 123: Hot Topic Anabolic Therapy for Osteoporosis. The Journal of Clinical Endocrinology & Metabolism, 86(3): 957–964, (Mar. 2001).

Tanizawa et al., Effects of human PTH (1–34) and bisphosphonate on the osteopenic rat model. Toxicology Letters. 102–103: 399–403, (Dec. 1998).

Wronski, T. J., et al., Parathyroid Hormone is More Effective Than Estrogen or Bisphosphonates for Restoration of Lost Bone Mass in Ovariectomized Rats. ENDOCRINOLOGY, 132(2): 823–831, (Feb. 1993).

* cited by examiner

FIG. 3A

```
    ATGGACAAAACTCACACATGTCCACCTTGTCCAGCTCCGGAACTCCTGGGGGGACCGTCA
  1 ------+---------+---------+---------+---------+---------+  60
    TACCTGTTTTGAGTGTGTACAGGTGGAACAGGTCGAGGCCTTGAGGACCCCCCTGGCAGT

M  D  K  T  H  T  C  P  P  C  P  A  P  E  L  L  G  G  P  S  -

GTCTTCCTCTTCCCCCCAAAACCCAAGGACACCCTCATGATCTCCCGGACCCCTGAGGTC
 61 ------+---------+---------+---------+---------+---------+ 120
    CAGAAGGAGAAGGGGGGTTTTGGGTTCCTGTGGGAGTACTAGAGGGCCTGGGGACTCCAG

V  F  L  F  P  P  K  P  K  D  T  L  M  I  S  R  T  P  E  V  -

ACATGCGTGGTGGTGGACGTGAGCCACGAAGACCCTGAGGTCAAGTTCAACTGGTACGTG
121 ------+---------+---------+---------+---------+---------+ 180
    TGTACGCACCACCACCTGCACTCGGTGCTTCTGGGACTCCAGTTCAAGTTGACCATGCAC

T  C  V  V  V  D  V  S  H  E  D  P  E  V  K  F  N  W  Y  V  -

GACGGCGTGGAGGTGCATAATGCCAAGACAAAGCCGCGGGAGGAGCAGTACAACAGCACG
181 ------+---------+---------+---------+---------+---------+ 240
    CTGCCGCACCTCCACGTATTACGGTTCTGTTTCGGCCCTCCTCGTCATGTTGTCGTGC

```
      TACCGTGTGGTCAGCGTCCTCACCGTCCTGCACCAGGACTGGCTGAATGGCAAGGAGTAC
241   ------------+---------+---------+---------+---------+---------+   300
      ATGGCACACCAGTCGCAGGAGTGGCAGGACGTGGTCCTGACCGACTTACCGTTCCTCATG

Y  R  V  V  S  V  L  T  V  L  H  Q  D  W  L  N  G  K  E  Y     -
  a

AAGTGCAAGGTCTCCAACAAAGCCCTCCCAGCCCCCATCGAGAAAACCATCTCCAAAGCC
301   ------------+---------+---------+---------+---------+---------+   360
      TTCACGTTCCAGAGGTTGTTTCGGGAGGGTCGGGGGTAGCTCTTTTGGTAGAGGTTTCGG

K  C  K  V  S  N  K  A  L  P  A  P  I  E  K  T  I  S  K  A     -
  a

AAAGGGCAGCCCCGAGAACCACAGGTGTACACCCTGCCCCCATCCCGGGATGAGCTGACC
361   ------------+---------+---------+---------+---------+---------+   420
      TTTCCCGTCGGGGCTCTTGGTGTCCACATGTGGGACGGGGGTAGGGCCCTACTCGACTGG

K  G  Q  P  R  E  P  Q  V  Y  T  L  P  P  S  R  D  E  L  T     -
  a

AAGAACCAGGTCAGCCTGACCTGCCTGGTCAAAGGCTTCTATCCCAGCGACATCGCCGTG
421   ------------+---------+---------+---------+---------+---------+   480
      TTCTTGGTCCAGTCGGACTGGACGGACCAGTTTCCGAAGATAGGGTCGCTGTAGCGGCAC

```
     GAGTGGGAGAGCAATGGGCAGCCGGAGAACAACTACAAGACCACGCCTCCCGTGCTGGAC
481  ------+---------+---------+---------+---------+---------+    540
     CTCACCCTCTCGTTACCCGTCGGCCTCTTGTTGATGTTCTGGTGCGGAGGGCACGACCTG a    E  W  E  S  N  G  Q  P  E  N  N  Y  K  T  T  P  P  V  L  D    -

TCCGACGGCTCCTTCTTCCTCTACAGCAAGCTCACCGTGGACAAGAGCAGGTGGCAGCAG
541  ------+---------+---------+---------+---------+---------+    600
     AGGCTGCCGAGGAAGAAGGAGATGTCGTTCGAGTGGCACCTGTTCTCGTCCACCGTCGTC a    S  D  G  S  F  F  L  Y  S  K  L  T  V  D  K  S  R  W  Q  Q    -

GGGAACGTGTTCTCATGCTCCGTGATGCATGAGGCTCTGCACAACCACTACACGCAGAAG
601  ------+---------+---------+---------+---------+---------+    660
     CCCTTGCACAAGAGTACGAGGCACTACGTACTCCGAGACGTGTTGGTGATGTGCGTCTTC a    G  N  V  F  S  C  S  V  M  H  E  A  L  H  N  H  Y  T  Q  K    -

AGCCTCTCCCTGTCTCCGGGTAAA
661  ------+---------+----    684
     TCGGAGAGGGACAGAGGCCCATTT a    S  L  S  L  S  P  G  K    -
```

Effect of Single Dose SC Administration of PTH(1-34)Fc on Calcium

- Animal #1 Dose 1 μg/kg
- Animal #2 Dose 3 μg/kg
- Animal #3 Dose 10 μg/kg
- Animal #4 Dose 30 μg/kg
- Animal #5 Dose 100 μg/kg
- Animal #6 Dose 300 μg/kg
- Animal #7 Dose 1000 μg/kg
- Animal #8 Dose 100 μg/kg
- Animal #9 Dose 30 μg/kg
- Animal #10 Dose 300 μg/kg

SEQUENCE LISTING

```
<160> NUMBER OF SEQ ID NOS: 170

<210> SEQ ID NO 1
<211> LENGTH: 684
<212> TYPE: DNA
<213> ORGANISM: Homo sapiens
<220> FEATURE:
<221> NAME/KEY: CDS
<222> LOCATION: (1)..(684)
<223> OTHER INFORMATION:

<400> SEQUENCE: 1 atg gac aaa act cac aca tgt cca cct tgt cca gct ccg gaa ctc ctg        48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc        96
Gly Gly Pro Ser Val Phe Leu Phe Pro Pro Lys Pro Lys Asp Thr Leu
                20                  25                  30 atg atc tcc cgg acc cct gag gtc aca tgc gtg gtg gtg gac gtg agc       144
Met Ile Ser Arg Thr Pro Glu Val Thr Cys Val Val Val Asp Val Ser
            35                  40                  45 cac gaa gac cct gag gtc aag ttc aac tgg tac gtg gac ggc gtg gag       192
His Glu Asp Pro Glu Val Lys Phe Asn Trp Tyr Val Asp Gly Val Glu
        50                  55                  60 gtg cat aat gcc aag aca aag ccg cgg gag gag cag tac aac agc acg       240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat       288
Tyr Arg Val Val Ser Val Leu Thr Val Leu His Gln Asp Trp Leu Asn
                85                  90                  95
```

```
ggc aag gag tac aag tgc aag gtc tcc aac aaa gcc ctc cca gcc ccc      336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag      384
Ile Glu Lys Thr Ile Ser Lys Ala Lys Gly Gln Pro Arg Glu Pro Gln
        115                 120                 125 gtg tac acc ctg ccc cca tcc cgg gat gag ctg acc aag aac cag gtc      432
Val Tyr Thr Leu Pro Pro Ser Arg Asp Glu Leu Thr Lys Asn Gln Val
    130                 135                 140 agc ctg acc tgc ctg gtc aaa ggc ttc tat ccc agc gac atc gcc gtg      480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct      528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc      576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg      624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg      672
Met His Glu Ala Leu His Asn His Tyr Thr Gln Lys Ser Leu Ser Leu
    210                 215                 220 tct ccg ggt aaa                                                      684
Ser Pro Gly Lys
225

<210> SEQ ID NO 2
<211> LENGTH: 228
<212> TYPE: PRT
<213> ORGANISM: Homo sapiens

<400> SEQUENCE: 2

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190
```

```
Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 3
<211> LENGTH: 21
<212> TYPE: PRT
<213> ORGANISM: Artificial Sequence
<220> FEATURE:
<223> OTHER INFORMATION: PTH/PTHrP
<221> NAME/KEY: misc_feature
<222> LOCATION: (1 )..(1)
<223> OTHER INFORMATION: Optional attachment to X3X4X5X6X7,
      X2X3X4X5X6X7,  X1X2X3X4X5X6X7, or YX1X2X3X4X5X6X7
<221> NAME/KEY: misc_feature
<222> LOCATION: (1)..(1)
<223> OTHER INFORMATION: X8 is an amino acid residue (nonfunctional
      residue preferred, M or Nle most preferred)
<221> NAME/KEY: misc_feature
<222> LOCATION: (3)..(3)
<223> OTHER INFORMATION: X10 is an amino acid residue (an acidic or
      hydrophilic residue preferred, N or D most preferred)
<221> NAME/KEY: misc_feature
<222> LOCATION: (4)..(4)
<223> OTHER INFORMATION: X11 is an amino acid residue (nonfunctional or
      basic residue preferred, L, R, or K most preferred)
<221> NAME/KEY: misc_feature
<222> LOCATION: (5)..(5)
<223> OTHER INFORMATION: X12 is an amino acid residue (nonfunctional or
      aromatic residue preferred, G, F, or W most preferred)
<221> NAME/KEY: misc_feature
<222> LOCATION: (7)..(7)
<223> OTHER INFORMATION: X14 is an amino acid residue (basic or
      hydrophilic residue preferred, H or S most preferred)
<221> NAME/KEY: misc_feature
<222> LOCATION: (8)..(8)
<223> OTHER INFORMATION: X15 is an amino acid residue (nonfunctional
      residue preferred, with L or I most preferred)
<221> NAME/KEY: misc_feature
<222> LOCATION: (9)..(9)
<223> OTHER INFORMATION: X16 is an amino acid residue (nonfunctional
      or hydrophilic residue preferred, Q, N, S, or A most preferred)
<221> NAME/KEY: misc_feature
<222> LOCATION: (10)..(10)
<223> OTHER INFORMATION: X17 is an amino acid residue (acidic,
      hydrophilic, or nonfunctional residue preferred, S, D, or L most
      preferred)
<221> NAME/KEY: misc_feature
<222> LOCATION: (11)..(11)
<223> OTHER INFORMATION: X18 is an amino acid residue (nonfunctional
      residue preferred, M, L, V or Nle most preferred)
<221> NAME/KEY: misc_feature
<222> LOCATION: (12)..(12)
<223> OTHER INFORMATION: X19 is an amino acid residue (acidic or basic
      residue preferred, E or R most preferred)
<221> NAME/KEY: misc_feature
<222> LOCATION: (14)..(14)
<223> OTHER INFORMATION: X21  is an amino acid residue (nonfunctional
      residue or basic residue preferred; V, M, R, or Nle most
      preferred)
<221> NAME/KEY: misc_feature
<222> LOCATION: (15)..(15)
<223> OTHER INFORMATION: X22  is an amino acid residue (hydrophilic,
      acidic, or aromatic residue preferred, E or F most preferred)
<221> NAME/KEY: misc_feature
<222> LOCATION: (16)..(16)
<223> OTHER INFORMATION: X23 is an aromatic or lipophilic residue (W or
      F preferred)
<221> NAME/KEY: misc_feature
<222> LOCATION: (17)..(17)
<223> OTHER INFORMATION: X24 is a lipophilic residue (L preferred)
<221> NAME/KEY: misc_feature
```

```
<222> LOCATION: (18)..(18)
<223> OTHER INFORMATION: X25  is an amino acid residue (hydrophilic or
      basic residue preferred, R or H most preferred)
<221> NAME/KEY: misc_feature
<222> LOCATION: (19)..(19)
<223> OTHER INFORMATION: X26  is an amino acid residue (hydrophilic or
      basic residue preferred, K or H most preferred)
<221> NAME/KEY: misc_feature
<222> LOCATION: (20)..(20)
<223> OTHER INFORMATION: X27  is an amino acid residue (lipophilic,
      basic, or nonfunctional residue preferred, K or L most preferred)
<221> NAME/KEY: misc_feature
<222> LOCATION: (21)..(21)
<223> OTHER INFORMATION: X28 is an amino acid residue (lipophilic or
      nonfunctional residue preferred, L or I most preferred)
<221> NAME/KEY: misc_feature
<222> LOCATION: (21)..(21)
<223> OTHER INFORMATION: Optional attachment to X29, X29X30, X29X30X31,
      X29X30 X31X32, X29X30X31X32X33,  X29X30X31X32X33X34,
      X29X30X31X32X33X34X35, or X29X30X31X32X33X34X35X36

<400> SEQUENCE: 3

Xaa His Xaa Xaa Xaa Lys Xaa Xaa Xaa Xaa Xaa Xaa Arg Xaa Xaa Xaa
1               5                   10                  15

Xaa Xaa Xaa Xaa Xaa
            20

<210> SEQ ID NO 4
<211> LENGTH: 22
<212> TYPE: PRT
<213> ORGANISM: Artificial Sequence
<220> FEATURE:
<223> OTHER INFORMATION: PTH/PTHrP
<221> NAME/KEY: misc_feature
<222> LOCATION: (1)..(1)
<223> OTHER INFORMATION: Optional attachment to J1J2J3J4J5J6,
      J2J3J4J5J6, J3J4J5J6
<221> NAME/KEY: misc_feature
<222> LOCATION: (1)..(1)
<223> OTHER INFORMATION: J7 is an amino acid residue (nonfunctional or
      aromatic residue preferred, L or F most preferred)
<221> NAME/KEY: misc_feature
<222> LOCATION: (2)..(2)
<223> OTHER INFORMATION: J8 is an amino acid residue (nonfunctional
      residue preferred, M or Nle most preferred)
<221> NAME/KEY: misc_feature
<222> LOCATION: (6)..(6)
<223> OTHER INFORMATION: J12 is an amino acid residue (nonfunctional
      or aromatic residue preferred, G or W most preferred)
<221> NAME/KEY: misc_feature
<222> LOCATION: (10)..(10)
<223> OTHER INFORMATION: J16 is an amino acid residue (nonfunctional or
      hydrophilic residue preferred, N, S, or A most preferred)
<221> NAME/KEY: misc_feature
<222> LOCATION: (12)..(12)
<223> OTHER INFORMATION: J18 is an amino acid residue (nonfunctional
      residue preferred, M, Nle, L, or V most preferred)
<221> NAME/KEY: misc_feature
<222> LOCATION: (13)..(13)
<223> OTHER INFORMATION: J19 is an acidic or basic residue (E or R
      preferred)
<221> NAME/KEY: misc_feature
<222> LOCATION: (15)..(15)
<223> OTHER INFORMATION: J21 is an amino acid residue (nonfunctional
      residue preferred, V, M, or Nle most preferred)
<221> NAME/KEY: misc_feature
<222> LOCATION: (22)..(22)
<223> OTHER INFORMATION: Optional attachment to J29, J29J30, J29J30J31,
      J29J30J31J32, J29J30J31J32J33, or J29J30J31J32J33J3

<400> SEQUENCE: 4

Xaa Xaa His Asn Leu Xaa Lys His Leu Xaa Ser Xaa Xaa Arg Xaa Glu
1               5                   10                  15

Trp Leu Arg Lys Lys Leu
```

```
<210> SEQ ID NO 5
<211> LENGTH: 21
<212> TYPE: PRT
<213> ORGANISM: Artificial Sequence
<220> FEATURE:
<223> OTHER INFORMATION: PTH/PTHrP
<221> NAME/KEY: misc_feature
<222> LOCATION: (1)..(1)
<223> OTHER INFORMATION: Optional attachment to Y01O2O3O4O5O6O7,
      O1O2O3O4O5O6O7, O2O3O4O5O6O7, O3O4O5O6O7, O4O5O6O7, O5O6O7, O6O7,
      or O7
<221> NAME/KEY: misc_feature
<222> LOCATION: (3)..(3)
<223> OTHER INFORMATION: O10 is an amino acid residue (acidic or
      hydrophilic residue preferred, N or D most preferred)
<221> NAME/KEY: misc_feature
<222> LOCATION: (4)..(4)
<223> OTHER INFORMATION: O11 is an amino acid residue (basic or
      nonfunctional residue preferred, K or L most preferred)
<221> NAME/KEY: misc_feature
<222> LOCATION: (5)..(5)
<223> OTHER INFORMATION: O12 is an amino acid residue (aromatic or
      nonfunctional residue preferred, G, F, or W most preferred)
<221> NAME/KEY: misc_feature
<222> LOCATION: (9)..(9)
<223> OTHER INFORMATION: O15 is an amino acid residue (hydrophilic or
      nonfunctional residue preferred, I or S most preferred)
<221> NAME/KEY: misc_feature
<222> LOCATION: (10)..(10)
<223> OTHER INFORMATION: O16 is an amino acid residue (hydrophilic
      residue preferred, Q or N most preferred)
<221> NAME/KEY: misc_feature
<222> LOCATION: (16)..(16)
<223> OTHER INFORMATION: O23 is an amino acid residue (aromatic residue
      preferred, with F or W most preferred)
<221> NAME/KEY: misc_feature
<222> LOCATION: (21)..(21)
<223> OTHER INFORMATION: Optional attachment to O29, O29O30, O29O30O31,
      O29O30O31O32, O29O30O31O32O33, O29O30O31O32O33O34,
      O29O30O31O32O33O34O35, or O29O30O31O32O33O34O35O36

<400> SEQUENCE: 5

Leu His Xaa Xaa Xaa Lys Ser Ile Xaa Xaa Leu Arg Arg Arg Phe Xaa
1               5                   10                  15

Leu His His Leu Ile
            20

<210> SEQ ID NO 6
<211> LENGTH: 8
<212> TYPE: PRT
<213> ORGANISM: Artificial Sequence
<220> FEATURE:
<223> OTHER INFORMATION: Preferred linker

<400> SEQUENCE: 6

Gly Gly Gly Lys Gly Gly Gly Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Preferred linker

<400> SEQUENCE: 7

Gly Gly Gly Asn Gly Ser Gly Gly
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: Preferred linker

<400> SEQUENCE: 8

Gly Gly Gly Cys Gly Gly Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Preferred linker

<400> SEQUENCE: 9

Gly Pro Asn Gly Gly
1               5

<210> SEQ ID NO 10
<211> LENGTH: 84
<212> TYPE: PRT
<213> ORGANISM: Homo sapiens

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 11
<211> LENGTH: 84
<212> TYPE: PRT
<213> ORGANISM: Rattus rattus

<400> SEQUENCE: 11

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
                20                  25                  30

Asn Phe Val Ser Leu Gly Val Gln Met Ala Ala Arg Glu Gly Ser Tyr
            35                  40                  45

Gln Arg Pro Thr Lys Lys Glu Asp Asn Val Leu Val Asp Gly Asn Ser
        50                  55                  60

Lys Ser Leu Gly Glu Gly Asp Lys Ala Asp Val Asp Val Leu Val Lys
65                  70                  75                  80

Ala Lys Ser Gln

<210> SEQ ID NO 12
<211> LENGTH: 78
<212> TYPE: PRT
```

<213> ORGANISM: Homo sapiens

<400> SEQUENCE: 12

Leu Met His Asn Leu Gly Lys His Leu Asn Ser Met Glu Arg Val Glu
1               5                   10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
50                  55                  60

Asp Lys Ala Asp Val Asn Val Leu Thr Lys Ala Lys Ser Gln
65                  70                  75

<210> SEQ ID NO 13
<211> LENGTH: 44
<212> TYPE: PRT
<213> ORGANISM: Homo sapiens

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg
        35                  40

<210> SEQ ID NO 14
<211> LENGTH: 38
<212> TYPE: PRT
<213> ORGANISM: Homo sapiens

<400> SEQUENCE: 14

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly
        35

<210> SEQ ID NO 15
<211> LENGTH: 37
<212> TYPE: PRT
<213> ORGANISM: Homo sapiens

<400> SEQUENCE: 15

Val Ser Glu Ile Gln Leu Met His Asn Leu Gly Lys His Leu Asn Ser
1               5                   10                  15

Met Glu Arg Val Glu Trp Leu Arg Lys Lys Leu Gln Asp Val His Asn
            20                  25                  30

Phe Val Ala Leu Gly
        35

<210> SEQ ID NO 16
<211> LENGTH: 34
<212> TYPE: PRT
<213> ORGANISM: Homo sapiens

<400> SEQUENCE: 16

Ser Val Ser Glu Ile Gln Leu Met His Asn Leu Gly Lys His Leu Asn

-continued

```
                1               5                  10                 15
Ser Met Glu Arg Val Glu Trp Leu Arg Lys Lys Leu Gln Asp Val His
            20                  25                  30

Asn Phe

<210> SEQ ID NO 17
<211> LENGTH: 34
<212> TYPE: PRT
<213> ORGANISM: Artificial Sequence
<220> FEATURE:
<223> OTHER INFORMATION: modified human PTH

<400> SEQUENCE: 17

Ser Val Ser Glu Ile Gln Leu Met His Asn Arg Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 18
<211> LENGTH: 34
<212> TYPE: PRT
<213> ORGANISM: Artificial Sequence
<220> FEATURE:
<223> OTHER INFORMATION: modified human PTH

<400> SEQUENCE: 18

Ser Val Ser Glu Ile Gln Leu Met His Asn Lys Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 19
<211> LENGTH: 34
<212> TYPE: PRT
<213> ORGANISM: Artificial Sequence
<220> FEATURE:
<223> OTHER INFORMATION: modified human PTH

<400> SEQUENCE: 19

Ser Val Ser Glu Ile Gln Leu Met His Asn Leu Gly Lys His Leu Asn
1               5                   10                  15

Ser Met Arg Arg Val Glu Trp Leu Arg Lys Lys Leu Gln Asp Val His
            20                  25                  30

Asn Phe

<210> SEQ ID NO 20
<211> LENGTH: 34
<212> TYPE: PRT
<213> ORGANISM: Artificial Sequence
<220> FEATURE:
<223> OTHER INFORMATION: modified human PTH

<400> SEQUENCE: 20

Tyr Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```

```
<210> SEQ ID NO 21
<211> LENGTH: 34
<212> TYPE: PRT
<213> ORGANISM: Artificial Sequence
<220> FEATURE:
<223> OTHER INFORMATION: modified human PTH

<400> SEQUENCE: 21

Ser Val Ser Glu Ile Gln Leu Leu His Asn Leu Gly Lys His Leu Asn
1               5                   10                  15

Ser Leu Glu Arg Val Glu Trp Leu Arg Lys Lys Leu Gln Asp Val His
            20                  25                  30

Asn Tyr

<210> SEQ ID NO 22
<211> LENGTH: 34
<212> TYPE: PRT
<213> ORGANISM: Artificial Sequence
<220> FEATURE:
<223> OTHER INFORMATION: bovine

<400> SEQUENCE: 22

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe

<210> SEQ ID NO 23
<211> LENGTH: 34
<212> TYPE: PRT
<213> ORGANISM: Artificial Sequence
<220> FEATURE:
<223> OTHER INFORMATION: modified bovine PTH

<400> SEQUENCE: 23

Ala Val Ser Glu Ile Gln Phe Leu His Asn Leu Gly Lys His Leu Ser
1               5                   10                  15

Ser Leu Glu Arg Val Glu Trp Leu Arg Lys Lys Leu Gln Asp Val His
            20                  25                  30

Asn Tyr

<210> SEQ ID NO 24
<211> LENGTH: 34
<212> TYPE: PRT
<213> ORGANISM: Artificial Sequence
<220> FEATURE:
<223> OTHER INFORMATION: porcine

<400> SEQUENCE: 24

Ser Val Ser Glu Ile Gln Leu Met His Asn Leu Gly Lys His Leu Ser
1               5                   10                  15

Ser Leu Glu Arg Val Glu Trp Leu Arg Lys Lys Leu Gln Asp Val His
            20                  25                  30

Asn Phe

<210> SEQ ID NO 25
<211> LENGTH: 34
<212> TYPE: PRT
<213> ORGANISM: Rattus rattus

<400> SEQUENCE: 25
```

```
Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 26
<211> LENGTH: 34
<212> TYPE: PRT
<213> ORGANISM: Artificial Sequence
<220> FEATURE:
<223> OTHER INFORMATION: modified rat PTH

<400> SEQUENCE: 26

Ala Val Ser Glu Ile Gln Leu Leu His Asn Leu Gly Lys His Leu Ala
1               5                   10                  15

Ser Val Glu Arg Leu Gln Trp Leu Arg Lys Lys Leu Gln Asp Val His
            20                  25                  30

Asn Tyr

<210> SEQ ID NO 27
<211> LENGTH: 31
<212> TYPE: PRT
<213> ORGANISM: Homo sapiens

<400> SEQUENCE: 27

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: modified human PTH

<400> SEQUENCE: 28

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Val
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: PTH

<400> SEQUENCE: 29

Ser Glu Ile Gln Leu Leu His Asn Leu Gly Lys His Leu Asn Ser Leu
1               5                   10                  15

Glu Arg Val Glu Trp Leu Arg Lys Lys Leu Gln Asp Val His Asn Tyr
            20                  25                  30

<210> SEQ ID NO 30
<211> LENGTH: 32
<212> TYPE: PRT
<213> ORGANISM: Artificial Sequence
<220> FEATURE:
```

<223> OTHER INFORMATION: bovine

<400> SEQUENCE: 30

Ser Glu Ile Gln Phe Met His Asn Leu Gly Lys His Leu Ser Ser Met
1               5                   10                  15

Glu Arg Val Glu Trp Leu Arg Lys Lys Leu Gln Asp Val His Asn Phe
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: modified bovine PTH

<400> SEQUENCE: 31

Ser Glu Ile Gln Phe Leu His Asn Leu Gly Lys His Leu Ser Ser Leu
1               5                   10                  15

Glu Arg Val Glu Trp Leu Arg Lys Lys Leu Gln Asp Val His Asn Tyr
            20                  25                  30

<210> SEQ ID NO 32
<211> LENGTH: 28
<212> TYPE: PRT
<213> ORGANISM: Homo sapiens

<400> SEQUENCE: 32

Leu Met His Asn Leu Gly Lys His Leu Asn Ser Met Glu Arg Val Glu
1               5                   10                  15

Trp Leu Arg Lys Lys Leu Gln Asp Val His Asn Phe
            20                  25

<210> SEQ ID NO 33
<211> LENGTH: 28
<212> TYPE: PRT
<213> ORGANISM: Artificial Sequence
<220> FEATURE:
<223> OTHER INFORMATION: modified human PTH

<400> SEQUENCE: 33

Leu Leu His Asn Leu Gly Lys His Leu Asn Ser Leu Glu Arg Val Glu
1               5                   10                  15

Trp Leu Arg Lys Lys Leu Gln Asp Val His Asn Tyr
            20                  25

<210> SEQ ID NO 34
<211> LENGTH: 28
<212> TYPE: PRT
<213> ORGANISM: Artificial Sequence
<220> FEATURE:
<223> OTHER INFORMATION: bovine PTH

<400> SEQUENCE: 34

Phe Met His Asn Leu Gly Lys His Leu Ser Ser Met Glu Arg Val Glu
1               5                   10                  15

Trp Leu Arg Lys Lys Leu Gln Asp Val His Asn Phe
            20                  25

<210> SEQ ID NO 35
<211> LENGTH: 28
<212> TYPE: PRT
<213> ORGANISM: Artificial Sequence
<220> FEATURE:
<223> OTHER INFORMATION: modified bovine PTH

```
<400> SEQUENCE: 35

Phe Met His Asn Leu Gly Lys His Leu Ser Ser Met Glu Arg Val Glu
1               5                   10                  15

Trp Leu Arg Lys Lys Leu Gln Asp Val His Asn Tyr
            20                  25

<210> SEQ ID NO 36
<211> LENGTH: 28
<212> TYPE: PRT
<213> ORGANISM: Artificial Sequence
<220> FEATURE:
<223> OTHER INFORMATION: modified bovine PTH

<400> SEQUENCE: 36

Phe Leu His Asn Leu Gly Lys His Leu Ser Ser Leu Glu Arg Val Glu
1               5                   10                  15

Trp Leu Arg Lys Lys Leu Gln Asp Val His Asn Tyr
            20                  25

<210> SEQ ID NO 37
<211> LENGTH: 5
<212> TYPE: PRT
<213> ORGANISM: Artificial Sequence
<220> FEATURE:
<223> OTHER INFORMATION: modified bovine PTH

<400> SEQUENCE: 37

Cys Asn Gly Arg Cys
1               5

<210> SEQ ID NO 38
<211> LENGTH: 27
<212> TYPE: PRT
<213> ORGANISM: Artificial Sequence
<220> FEATURE:
<223> OTHER INFORMATION: modified bovine PTH

<400> SEQUENCE: 38

Phe Met His Asn Leu Lys His Leu Ser Ser Met Glu Arg Val Glu Trp
1               5                   10                  15

Leu Arg Lys Lys Leu Gln Asp Val His Asn Tyr
            20                  25

<210> SEQ ID NO 39
<211> LENGTH: 30
<212> TYPE: PRT
<213> ORGANISM: Homo sapiens

<400> SEQUENCE: 39

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: modified human PTH

<400> SEQUENCE: 40

Ser Val Ser Glu Ile Gln Leu Met His Asn Arg Gly Lys His Leu Asn
```

```
                   1               5                  10                 15
Ser Met Glu Arg Val Glu Trp Leu Arg Lys Lys Leu Gln Asp
        20                  25                 30

<210> SEQ ID NO 41
<211> LENGTH: 30
<212> TYPE: PRT
<213> ORGANISM: Artificial Sequence
<220> FEATURE:
<223> OTHER INFORMATION: modified human PTH

<400> SEQUENCE: 41

Ser Val Ser Glu Ile Gln Leu Met His Asn Lys Gly Lys His Leu Asn
1               5                  10                 15
Ser Met Glu Arg Val Glu Trp Leu Arg Lys Lys Leu Gln Asp
        20                  25                 30

<210> SEQ ID NO 42
<211> LENGTH: 30
<212> TYPE: PRT
<213> ORGANISM: Artificial Sequence
<220> FEATURE:
<223> OTHER INFORMATION: modified human PTH

<400> SEQUENCE: 42

Ser Val Ser Glu Ile Gln Leu Met His Asn Leu Gly Lys His Leu Asn
1               5                  10                 15
Ser Met Arg Arg Val Glu Trp Leu Arg Lys Lys Leu Gln Asp
        20                  25                 30

<210> SEQ ID NO 43
<211> LENGTH: 30
<212> TYPE: PRT
<213> ORGANISM: Artificial Sequence
<220> FEATURE:
<223> OTHER INFORMATION: modified human PTH

<400> SEQUENCE: 43

Tyr Val Ser Glu Ile Gln Leu Met His Asn Leu Gly Lys His Leu Asn
1               5                  10                 15
Ser Met Glu Arg Val Glu Trp Leu Arg Lys Lys Leu Gln Asp
        20                  25                 30

<210> SEQ ID NO 44
<211> LENGTH: 30
<212> TYPE: PRT
<213> ORGANISM: Artificial Sequence
<220> FEATURE:
<223> OTHER INFORMATION: modified human PTH

<400> SEQUENCE: 44

Ser Val Ser Glu Ile Gln Leu Leu His Asn Leu Gly Lys His Leu Asn
1               5                  10                 15
Ser Leu Glu Arg Val Glu Trp Leu Arg Lys Lys Leu Gln Asp
        20                  25                 30

<210> SEQ ID NO 45
<211> LENGTH: 30
<212> TYPE: PRT
<213> ORGANISM: Artificial Sequence
<220> FEATURE:
<223> OTHER INFORMATION: bovine

<400> SEQUENCE: 45
```

```
Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp
            20                  25                  30
```

<210> SEQ ID NO 46
<211> LENGTH: 30
<212> TYPE: PRT
<213> ORGANISM: Artificial Sequence
<220> FEATURE:
<223> OTHER INFORMATION: modified bovine PTH

<400> SEQUENCE: 46

```
Ala Val Ser Glu Ile Gln Phe Leu His Asn Leu Gly Lys His Leu Ser
1               5                   10                  15

Ser Leu Glu Arg Val Glu Trp Leu Arg Lys Lys Leu Gln Asp
            20                  25                  30
```

<210> SEQ ID NO 47
<211> LENGTH: 30
<212> TYPE: PRT
<213> ORGANISM: Artificial Sequence
<220> FEATURE:
<223> OTHER INFORMATION: porcine PTH

<400> SEQUENCE: 47

```
Ser Val Ser Glu Ile Gln Leu Met His Asn Leu Gly Lys His Leu Ser
1               5                   10                  15

Ser Leu Glu Arg Val Glu Trp Leu Arg Lys Lys Leu Gln Asp
            20                  25                  30
```

<210> SEQ ID NO 48
<211> LENGTH: 30
<212> TYPE: PRT
<213> ORGANISM: Artificial Sequence
<220> FEATURE:
<223> OTHER INFORMATION: rat PTH

<400> SEQUENCE: 48

```
Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp
            20                  25                  30
```

<210> SEQ ID NO 49
<211> LENGTH: 30
<212> TYPE: PRT
<213> ORGANISM: Artificial Sequence
<220> FEATURE:
<223> OTHER INFORMATION: modified rat PTH

<400> SEQUENCE: 49

```
Ala Val Ser Glu Ile Gln Leu Leu His Asn Leu Gly Lys His Leu Ala
1               5                   10                  15

Ser Val Glu Arg Leu Gln Trp Leu Arg Lys Lys Leu Gln Asp
            20                  25                  30
```

<210> SEQ ID NO 50
<211> LENGTH: 30
<212> TYPE: PRT
<213> ORGANISM: Artificial Sequence
<220> FEATURE:
<223> OTHER INFORMATION: modified human PTH

<400> SEQUENCE: 50

```
Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp
            20                  25                  30

<210> SEQ ID NO 51
<211> LENGTH: 29
<212> TYPE: PRT
<213> ORGANISM: Homo sapiens

<400> SEQUENCE: 51

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 52
<211> LENGTH: 28
<212> TYPE: PRT
<213> ORGANISM: Homo sapiens

<400> SEQUENCE: 52

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 53
<211> LENGTH: 28
<212> TYPE: PRT
<213> ORGANISM: Artificial Sequence
<220> FEATURE:
<223> OTHER INFORMATION: modified PTH

<400> SEQUENCE: 53

Ser Glu Ile Gln Leu Leu His Asn Leu Gly Lys His Leu Asn Ser Leu
1               5                   10                  15

Glu Arg Val Glu Trp Leu Arg Lys Lys Leu Gln Asp
            20                  25

<210> SEQ ID NO 54
<211> LENGTH: 28
<212> TYPE: PRT
<213> ORGANISM: Artificial Sequence
<220> FEATURE:
<223> OTHER INFORMATION: bovine

<400> SEQUENCE: 54

Ser Glu Ile Gln Phe Met His Asn Leu Gly Lys His Leu Ser Ser Met
1               5                   10                  15

Glu Arg Val Glu Trp Leu Arg Lys Lys Leu Gln Asp
            20                  25

<210> SEQ ID NO 55
<211> LENGTH: 28
<212> TYPE: PRT
<213> ORGANISM: Artificial Sequence
<220> FEATURE:
<223> OTHER INFORMATION: modified bovine PTH

<400> SEQUENCE: 55

Ser Glu Ile Gln Phe Leu His Asn Leu Gly Lys His Leu Ser Ser Leu
1               5                   10                  15
```

Glu Arg Val Glu Trp Leu Arg Lys Lys Leu Gln Asp
            20                  25

<210> SEQ ID NO 56
<211> LENGTH: 24
<212> TYPE: PRT
<213> ORGANISM: Homo sapiens

<400> SEQUENCE: 56

Leu Met His Asn Leu Gly Lys His Leu Asn Ser Met Glu Arg Val Glu
1               5                   10                  15

Trp Leu Arg Lys Lys Leu Gln Asp
            20

<210> SEQ ID NO 57
<211> LENGTH: 24
<212> TYPE: PRT
<213> ORGANISM: Artificial Sequence
<220> FEATURE:
<223> OTHER INFORMATION: modified human PTH

<400> SEQUENCE: 57

Leu Leu His Asn Leu Gly Lys His Leu Asn Ser Leu Glu Arg Val Glu
1               5                   10                  15

Trp Leu Arg Lys Lys Leu Gln Asp
            20

<210> SEQ ID NO 58
<211> LENGTH: 24
<212> TYPE: PRT
<213> ORGANISM: Artificial Sequence
<220> FEATURE:
<223> OTHER INFORMATION: bovine

<400> SEQUENCE: 58

Phe Met His Asn Leu Gly Lys His Leu Ser Ser Met Glu Arg Val Glu
1               5                   10                  15

Trp Leu Arg Lys Lys Leu Gln Asp
            20

<210> SEQ ID NO 59
<211> LENGTH: 24
<212> TYPE: PRT
<213> ORGANISM: Artificial Sequence
<220> FEATURE:
<223> OTHER INFORMATION: modified bovine PTH

<400> SEQUENCE: 59

Phe Leu His Asn Leu Gly Lys His Leu Ser Ser Leu Glu Arg Val Glu
1               5                   10                  15

Trp Leu Arg Lys Lys Leu Gln Asp
            20

<210> SEQ ID NO 60
<211> LENGTH: 24
<212> TYPE: PRT
<213> ORGANISM: Artificial Sequence
<220> FEATURE:
<223> OTHER INFORMATION: modified bovine PTH

<400> SEQUENCE: 60

Phe Leu His Asn Leu Trp Lys His Leu Ser Ser Leu Glu Arg Val Glu
1               5                   10                  15

Trp Leu Arg Lys Lys Leu Gln Asp
            20

<210> SEQ ID NO 61
<211> LENGTH: 24
<212> TYPE: PRT
<213> ORGANISM: Artificial Sequence
<220> FEATURE:
<223> OTHER INFORMATION: modified bovine PTH
<221> NAME/KEY: misc_feature
<222> LOCATION: (7)..(7)
<223> OTHER INFORMATION: D amino acid

<400> SEQUENCE: 61

Phe Met His Asn Leu Lys Trp His Leu Ser Ser Met Glu Arg Val Glu
1               5                   10                  15

Trp Leu Arg Lys Lys Leu Gln Asp
            20

<210> SEQ ID NO 62
<211> LENGTH: 86
<212> TYPE: PRT
<213> ORGANISM: Homo sapiens

<400> SEQUENCE: 62

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro
                85

<210> SEQ ID NO 63
<211> LENGTH: 34
<212> TYPE: PRT
<213> ORGANISM: Homo sapiens

<400> SEQUENCE: 63

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala

<210> SEQ ID NO 64
<211> LENGTH: 36
<212> TYPE: PRT
<213> ORGANISM: Artificial Sequence
<220> FEATURE:
<223> OTHER INFORMATION: modified human PTHrP

<400> SEQUENCE: 64

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Tyr
        35

<210> SEQ ID NO 65
<211> LENGTH: 36
<212> TYPE: PRT
<213> ORGANISM: Artificial Sequence
<220> FEATURE:
<223> OTHER INFORMATION: modified human PTHrP

<400> SEQUENCE: 65

Ala Val Ser Glu Ile Gln Leu Leu His Asp Lys Gly Lys Ser Ile Gln
1               5                   10                  15

Asp Leu Arg Arg Arg Phe Trp Leu His His Leu Ile Ala Glu Ile His
            20                  25                  30

Thr Ala Glu Tyr
        35

<210> SEQ ID NO 66
<211> LENGTH: 35
<212> TYPE: PRT
<213> ORGANISM: Artificial Sequence
<220> FEATURE:
<223> OTHER INFORMATION: modified human PTHrP

<400> SEQUENCE: 66

Tyr Ala Val Ser Glu His Gln Leu Leu His Asp Lys Gly Lys Ser Ile
1               5                   10                  15

Gln Asp Leu Arg Arg Arg Phe Phe Leu His His Leu Ile Ala Glu Ile
            20                  25                  30

His Thr Ala
        35

<210> SEQ ID NO 67
<211> LENGTH: 33
<212> TYPE: PRT
<213> ORGANISM: Artificial Sequence
<220> FEATURE:
<223> OTHER INFORMATION: modified human PTHrP

<400> SEQUENCE: 67

Ala Val Ser Glu His Gln Leu Leu His Asn Leu Lys Ser Ile Gln Asp
1               5                   10                  15

Leu Arg Arg Arg Phe Phe Leu His His Leu Ile Ala Glu Ile His Thr
            20                  25                  30

Ala

<210> SEQ ID NO 68
<211> LENGTH: 28
<212> TYPE: PRT
<213> ORGANISM: Homo sapiens

<400> SEQUENCE: 68

Leu Leu His Asp Lys Gly Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 69
<211> LENGTH: 28
<212> TYPE: PRT
<213> ORGANISM: Artificial Sequence

```
<220> FEATURE:
<223> OTHER INFORMATION: modified human PTHrP

<400> SEQUENCE: 69

Leu Leu His Asn Leu Gly Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 70
<211> LENGTH: 28
<212> TYPE: PRT
<213> ORGANISM: Artificial Sequence
<220> FEATURE:
<223> OTHER INFORMATION: modified PTHrP

<400> SEQUENCE: 70

Leu Leu His Asp Lys Gly Lys Ser Ile Asn Leu Leu Arg Arg Arg Phe
1               5                   10                  15

Phe Leu His His Leu Ile Ala Glu Ile His Thr Ala
            20                  25

<210> SEQ ID NO 71
<211> LENGTH: 28
<212> TYPE: PRT
<213> ORGANISM: Artificial Sequence
<220> FEATURE:
<223> OTHER INFORMATION: modified human PTHrP
<221> NAME/KEY: misc_feature
<222> LOCATION: (6)..(6)
<223> OTHER INFORMATION: D amino acid

<400> SEQUENCE: 71

Leu Leu His Asp Leu Trp Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 72
<211> LENGTH: 28
<212> TYPE: PRT
<213> ORGANISM: Artificial Sequence
<220> FEATURE:
<223> OTHER INFORMATION: modified PTHrP
<221> NAME/KEY: misc_feature
<222> LOCATION: (6)..(6)
<223> OTHER INFORMATION: D amino acid

<400> SEQUENCE: 72

Leu Leu His Asn Leu Trp Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 73
<211> LENGTH: 27
<212> TYPE: PRT
<213> ORGANISM: Artificial Sequence
<220> FEATURE:
<223> OTHER INFORMATION: modified PTHrP
<221> NAME/KEY: misc_feature
<222> LOCATION: (5)..(5)
<223> OTHER INFORMATION: D amino acid

<400> SEQUENCE: 73

Leu His Asn Leu Trp Lys Ser Ile Gln Asp Leu Arg Arg Arg Phe Phe
```

```
                 1               5                  10                 15
Leu His His Leu Ile Ala Glu Ile His Thr Ala
                20                  25

<210> SEQ ID NO 74
<211> LENGTH: 27
<212> TYPE: PRT
<213> ORGANISM: Artificial Sequence
<220> FEATURE:
<223> OTHER INFORMATION: modified PTHrP
<221> NAME/KEY: misc_feature
<222> LOCATION: (5)..(5)
<223> OTHER INFORMATION: D amino acid

<400> SEQUENCE: 74

Leu His Asn Leu Phe Lys Ser Ile Gln Asp Leu Arg Arg Arg Phe Phe
1               5                  10                  15
Leu His His Leu Ile Ala Glu Ile His Thr Ala
                20                  25

<210> SEQ ID NO 75
<211> LENGTH: 28
<212> TYPE: PRT
<213> ORGANISM: Artificial Sequence
<220> FEATURE:
<223> OTHER INFORMATION: modified human PTHrP
<221> NAME/KEY: misc_feature
<222> LOCATION: (6)..(6)
<223> OTHER INFORMATION: D amino acid

<400> SEQUENCE: 75

Leu Leu His Asn Leu Trp Lys Ser Ile Gln Asp Leu Arg Arg Arg Phe
1               5                  10                  15
Phe Leu His His Leu Ile Ala Glu Ile His Thr Ala
                20                  25

<210> SEQ ID NO 76
<211> LENGTH: 30
<212> TYPE: PRT
<213> ORGANISM: Homo sapiens

<400> SEQUENCE: 76

Ala Val Ser Glu His Gln Leu Leu His Asp Lys Gly Lys Ser Ile Gln
1               5                  10                  15
Asp Leu Arg Arg Arg Phe Phe Leu His His Leu Ile Ala Glu
                20                  25                  30

<210> SEQ ID NO 77
<211> LENGTH: 30
<212> TYPE: PRT
<213> ORGANISM: Artificial Sequence
<220> FEATURE:
<223> OTHER INFORMATION: modified human PTHrP

<400> SEQUENCE: 77

Ala Val Ser Glu Ile Gln Leu Leu His Asp Lys Gly Lys Ser Ile Gln
1               5                  10                  15
Asp Leu Arg Arg Arg Phe Trp Leu His His Leu Ile Ala Glu
                20                  25                  30

<210> SEQ ID NO 78
<211> LENGTH: 31
<212> TYPE: PRT
<213> ORGANISM: Artificial Sequence
<220> FEATURE:
```

<223> OTHER INFORMATION: human PTHrP with non-human N-terminal peptide

<400> SEQUENCE: 78

Tyr Ala Val Ser Glu His Gln Leu Leu His Asp Lys Gly Lys Ser Ile
1               5                   10                  15

Gln Asp Leu Arg Arg Arg Phe Phe Leu His His Leu Ile Ala Glu
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: modified human PTHrP
<221> NAME/KEY: misc_feature
<222> LOCATION: (12)..(12)
<223> OTHER INFORMATION: D amino acid

<400> SEQUENCE: 79

Ala Val Ser Glu His Gln Leu Leu His Asn Leu Phe Lys Ser Ile Gln
1               5                   10                  15

Asp Leu Arg Arg Arg Phe Phe Leu His His Leu Ile Ala Glu
            20                  25                  30

<210> SEQ ID NO 80
<211> LENGTH: 24
<212> TYPE: PRT
<213> ORGANISM: Homo sapiens

<400> SEQUENCE: 80

Leu Leu His Asp Lys Gly Lys Ser Ile Gln Asp Leu Arg Arg Arg Phe
1               5                   10                  15

Phe Leu His His Leu Ile Ala Glu
            20

<210> SEQ ID NO 81
<211> LENGTH: 24
<212> TYPE: PRT
<213> ORGANISM: Artificial Sequence
<220> FEATURE:
<223> OTHER INFORMATION: modified human PTHrP

<400> SEQUENCE: 81

Leu Leu His Asn Leu Gly Lys Ser Ile Gln Asp Leu Arg Arg Arg Phe
1               5                   10                  15

Phe Leu His His Leu Ile Ala Glu
            20

<210> SEQ ID NO 82
<211> LENGTH: 24
<212> TYPE: PRT
<213> ORGANISM: Artificial Sequence
<220> FEATURE:
<223> OTHER INFORMATION: modified PTHrP

<400> SEQUENCE: 82

Leu Leu His Asp Lys Gly Lys Ser Ile Asn Leu Leu Arg Arg Arg Phe
1               5                   10                  15

Phe Leu His His Leu Ile Ala Glu
            20

<210> SEQ ID NO 83
<211> LENGTH: 23
<212> TYPE: PRT

<213> ORGANISM: Artificial Sequence
<220> FEATURE:
<223> OTHER INFORMATION: modified human PTHrP

<400> SEQUENCE: 83

Leu Leu His Asp Leu Lys Ser Ile Gln Asp Leu Arg Arg Arg Phe Phe
1               5                   10                  15
Leu His His Leu Ile Ala Glu
            20

<210> SEQ ID NO 84
<211> LENGTH: 23
<212> TYPE: PRT
<213> ORGANISM: Artificial Sequence
<220> FEATURE:
<223> OTHER INFORMATION: modified PTHrP

<400> SEQUENCE: 84

Leu Leu His Asn Leu Lys Ser Ile Gln Asp Leu Arg Arg Arg Phe Phe
1               5                   10                  15
Leu His His Leu Ile Ala Glu
            20

<210> SEQ ID NO 85
<211> LENGTH: 23
<212> TYPE: PRT
<213> ORGANISM: Artificial Sequence
<220> FEATURE:
<223> OTHER INFORMATION: modified PTHrP
<221> NAME/KEY: misc_feature
<222> LOCATION: (5)..(5)
<223> OTHER INFORMATION: D amino acid

<400> SEQUENCE: 85

Leu His Asn Leu Trp Lys Ser Ile Gln Asp Leu Arg Arg Arg Phe Phe
1               5                   10                  15
Leu His His Leu Ile Ala Glu
            20

<210> SEQ ID NO 86
<211> LENGTH: 23
<212> TYPE: PRT
<213> ORGANISM: Artificial Sequence
<220> FEATURE:
<223> OTHER INFORMATION: modified PTHrP
<221> NAME/KEY: misc_feature
<222> LOCATION: (5)..(5)
<223> OTHER INFORMATION: D amino acid

<400> SEQUENCE: 86

Leu His Asn Leu Phe Lys Ser Ile Gln Asp Leu Arg Arg Arg Phe Phe
1               5                   10                  15
Leu His His Leu Ile Ala Glu
            20

<210> SEQ ID NO 87
<211> LENGTH: 24
<212> TYPE: PRT
<213> ORGANISM: Artificial Sequence
<220> FEATURE:
<223> OTHER INFORMATION: modified human PTHrP
<221> NAME/KEY: misc_feature
<222> LOCATION: (6)..(6)
<223> OTHER INFORMATION: D amino acid

<400> SEQUENCE: 87

-continued

Leu Leu His Asn Leu Trp Lys Ser Ile Gln Asp Leu Arg Arg Arg Phe
1               5                   10                  15

Phe Leu His His Leu Ile Ala Glu
            20

<210> SEQ ID NO 88
<211> LENGTH: 34
<212> TYPE: PRT
<213> ORGANISM: Artificial Sequence
<220> FEATURE:
<223> OTHER INFORMATION: modified human PTH

<400> SEQUENCE: 88

Ser Val Ser Glu Ile Gln Leu Met His Asn Leu Gly Lys His Leu Asn
1               5                   10                  15

Ser Met Glu Arg Val Glu Leu Leu Glu Lys Leu Leu Glu Lys Leu His
            20                  25                  30

Asn Phe

<210> SEQ ID NO 89
<211> LENGTH: 34
<212> TYPE: PRT
<213> ORGANISM: Artificial Sequence
<220> FEATURE:
<223> OTHER INFORMATION: modified human PTH

<400> SEQUENCE: 89

Ser Val Ser Glu Ile Gln Leu Met His Asn Leu Gly Lys His Leu Asn
1               5                   10                  15

Ser Met Glu Arg Val Glu Leu Leu Glu Lys Leu Leu Lys Lys Leu His
            20                  25                  30

Asn Phe

<210> SEQ ID NO 90
<211> LENGTH: 34
<212> TYPE: PRT
<213> ORGANISM: Artificial Sequence
<220> FEATURE:
<223> OTHER INFORMATION: modified human PTH

<400> SEQUENCE: 90

Ser Val Ser Glu Ile Gln Leu Met His Asn Leu Gly Lys His Leu Asn
1               5                   10                  15

Ser Met Glu Arg Val Ala Leu Ala Glu Ala Leu Ala Glu Ala Leu His
            20                  25                  30

Asn Phe

<210> SEQ ID NO 91
<211> LENGTH: 34
<212> TYPE: PRT
<213> ORGANISM: Artificial Sequence
<220> FEATURE:
<223> OTHER INFORMATION: modified human PTH

<400> SEQUENCE: 91

Ser Val Ser Glu Ile Gln Leu Met His Asn Leu Gly Lys His Leu Asn
1               5                   10                  15

Ser Met Glu Arg Val Ser Leu Leu Ser Ser Leu Leu Ser Ser Leu His
            20                  25                  30

Asn Phe

```
<210> SEQ ID NO 92
<211> LENGTH: 34
<212> TYPE: PRT
<213> ORGANISM: Artificial Sequence
<220> FEATURE:
<223> OTHER INFORMATION: modified human PTH

<400> SEQUENCE: 92

Ser Val Ser Glu Ile Gln Leu Met His Asn Leu Gly Lys His Leu Asn
1               5                  10                  15

Ser Met Glu Arg Val Ala Phe Tyr Asp Lys Val Ala Glu Lys Leu His
            20                  25                  30

Asn Phe

<210> SEQ ID NO 93
<211> LENGTH: 28
<212> TYPE: PRT
<213> ORGANISM: Artificial Sequence
<220> FEATURE:
<223> OTHER INFORMATION: modified human PTH

<400> SEQUENCE: 93

Leu Met His Asn Leu Gly Lys His Leu Asn Ser Met Glu Arg Val Glu
1               5                  10                  15

Leu Leu Glu Lys Leu Leu Glu Lys Leu His Asn Phe
            20                  25

<210> SEQ ID NO 94
<211> LENGTH: 28
<212> TYPE: PRT
<213> ORGANISM: Artificial Sequence
<220> FEATURE:
<223> OTHER INFORMATION: modified human PTH

<400> SEQUENCE: 94

Leu Met His Asn Leu Gly Lys His Leu Asn Ser Met Glu Arg Val Glu
1               5                  10                  15

Leu Leu Glu Lys Leu Leu Lys Lys Leu His Asn Phe
            20                  25

<210> SEQ ID NO 95
<211> LENGTH: 28
<212> TYPE: PRT
<213> ORGANISM: Artificial Sequence
<220> FEATURE:
<223> OTHER INFORMATION: modified human PTH

<400> SEQUENCE: 95

Leu Met His Asn Leu Gly Lys His Leu Asn Ser Met Glu Arg Val Ala
1               5                  10                  15

Leu Ala Glu Ala Leu Ala Glu Ala Leu His Asn Phe
            20                  25

<210> SEQ ID NO 96
<211> LENGTH: 28
<212> TYPE: PRT
<213> ORGANISM: Artificial Sequence
<220> FEATURE:
<223> OTHER INFORMATION: modified human PTH

<400> SEQUENCE: 96

Leu Met His Asn Leu Gly Lys His Leu Asn Ser Met Glu Arg Val Ser
1               5                  10                  15

Leu Leu Ser Ser Leu Leu Ser Ser Leu His Asn Phe
```

20                  25

<210> SEQ ID NO 97
<211> LENGTH: 28
<212> TYPE: PRT
<213> ORGANISM: Artificial Sequence
<220> FEATURE:
<223> OTHER INFORMATION: modified human PTH

<400> SEQUENCE: 97

Leu Met His Asn Leu Gly Lys His Leu Asn Ser Met Glu Arg Val Ala
1               5                   10                  15

Phe Tyr Asp Lys Val Ala Glu Lys Leu His Asn Phe
            20                  25

<210> SEQ ID NO 98
<211> LENGTH: 34
<212> TYPE: PRT
<213> ORGANISM: Artificial Sequence
<220> FEATURE:
<223> OTHER INFORMATION: modified human PTHrP

<400> SEQUENCE: 98

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr Ala

<210> SEQ ID NO 99
<211> LENGTH: 34
<212> TYPE: PRT
<213> ORGANISM: Artificial Sequence
<220> FEATURE:
<223> OTHER INFORMATION: modified human PTHrP

<400> SEQUENCE: 99

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Lys Leu His
            20                  25                  30

Thr Ala

<210> SEQ ID NO 100
<211> LENGTH: 34
<212> TYPE: PRT
<213> ORGANISM: Artificial Sequence
<220> FEATURE:
<223> OTHER INFORMATION: modified human PTHrP

<400> SEQUENCE: 100

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala Leu His
            20                  25                  30

Thr Ala

<210> SEQ ID NO 101
<211> LENGTH: 34
<212> TYPE: PRT
<213> ORGANISM: Artificial Sequence
<220> FEATURE:
<223> OTHER INFORMATION: modified human PTHrP

<400> SEQUENCE: 101

Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Leu His
            20                  25                  30

Thr Ala

<210> SEQ ID NO 102
<211> LENGTH: 34
<212> TYPE: PRT
<213> ORGANISM: Artificial Sequence
<220> FEATURE:
<223> OTHER INFORMATION: modified human PTHrP

<400> SEQUENCE: 102

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys Leu His
            20                  25                  30

Thr Ala

<210> SEQ ID NO 103
<211> LENGTH: 28
<212> TYPE: PRT
<213> ORGANISM: Artificial Sequence
<220> FEATURE:
<223> OTHER INFORMATION: modified human PTHrP

<400> SEQUENCE: 103

Leu Leu His Asp Lys Gly Lys Ser Ile Gln Asp Leu Arg Arg Arg Glu
1               5                   10                  15

Leu Leu Glu Lys Leu Leu Glu Lys Leu His Thr Ala
            20                  25

<210> SEQ ID NO 104
<211> LENGTH: 28
<212> TYPE: PRT
<213> ORGANISM: Artificial Sequence
<220> FEATURE:
<223> OTHER INFORMATION: modified human PTHrP

<400> SEQUENCE: 104

Leu Leu His Asp Lys Gly Lys Ser Ile Gln Asp Leu Arg Arg Arg Glu
1               5                   10                  15

Leu Leu Glu Lys Leu Leu Lys Lys Leu His Thr Ala
            20                  25

<210> SEQ ID NO 105
<211> LENGTH: 28
<212> TYPE: PRT
<213> ORGANISM: Artificial Sequence
<220> FEATURE:
<223> OTHER INFORMATION: modified human PTHrP

<400> SEQUENCE: 105

Leu Leu His Asp Lys Gly Lys Ser Ile Gln Asp Leu Arg Arg Arg Ala
1               5                   10                  15

Leu Ala Glu Ala Leu Ala Glu Ala Leu His Thr Ala
            20                  25

<210> SEQ ID NO 106

```
<211> LENGTH: 28
<212> TYPE: PRT
<213> ORGANISM: Artificial Sequence
<220> FEATURE:
<223> OTHER INFORMATION: modified human PTHrP

<400> SEQUENCE: 106

Leu Leu His Asp Lys Gly Lys Ser Ile Gln Asp Leu Arg Arg Arg Ser
1               5                   10                  15

Leu Leu Ser Ser Leu Leu Ser Ser Leu His Thr Ala
            20                  25

<210> SEQ ID NO 107
<211> LENGTH: 28
<212> TYPE: PRT
<213> ORGANISM: Artificial Sequence
<220> FEATURE:
<223> OTHER INFORMATION: modified human PTHrP

<400> SEQUENCE: 107

Leu Leu His Asp Lys Gly Lys Ser Ile Gln Asp Leu Arg Arg Arg Ala
1               5                   10                  15

Phe Tyr Asp Lys Val Ala Glu Lys Leu His Thr Ala
            20                  25

<210> SEQ ID NO 108
<211> LENGTH: 34
<212> TYPE: PRT
<213> ORGANISM: Artificial Sequence
<220> FEATURE:
<223> OTHER INFORMATION: modified human PTHrP

<400> SEQUENCE: 108

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Arg Lys Leu His
            20                  25                  30

Thr Ala

<210> SEQ ID NO 109
<211> LENGTH: 34
<212> TYPE: PRT
<213> ORGANISM: Artificial Sequence
<220> FEATURE:
<223> OTHER INFORMATION: modified human PTHrP

<400> SEQUENCE: 109

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr Ser

<210> SEQ ID NO 110
<211> LENGTH: 37
<212> TYPE: PRT
<213> ORGANISM: Artificial Sequence
<220> FEATURE:
<223> OTHER INFORMATION: modified human PTHrP

<400> SEQUENCE: 110

Ala Val Ser Glu His Gln Leu Leu His Asp Lys Gly Lys Ser Ile Gln
1               5                   10                  15
```

-continued

Asp Leu Arg Arg Arg Glu Leu Leu Glu Lys Leu Leu Glu Lys Leu His
            20                  25                  30

Thr Ala Gly Arg Arg
        35

<210> SEQ ID NO 111
<211> LENGTH: 34
<212> TYPE: PRT
<213> ORGANISM: Artificial Sequence
<220> FEATURE:
<223> OTHER INFORMATION: modified human PTHrP

<400> SEQUENCE: 111

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu Lys
            20                  25                  30

Glu Leu

<210> SEQ ID NO 112
<211> LENGTH: 34
<212> TYPE: PRT
<213> ORGANISM: Artificial Sequence
<220> FEATURE:
<223> OTHER INFORMATION: modified human PTHrP

<400> SEQUENCE: 112

Ala Val Ser Glu His Gln Leu Leu His Asp Lys Gly Lys Ser Ile Gln
1               5                   10                  15

Asp Leu Ala Arg Arg Glu Leu Leu Glu Lys Leu Leu Glu Lys Leu His
            20                  25                  30

Thr Ala

<210> SEQ ID NO 113
<211> LENGTH: 34
<212> TYPE: PRT
<213> ORGANISM: Artificial Sequence
<220> FEATURE:
<223> OTHER INFORMATION: modified human PTHrP

<400> SEQUENCE: 113

Ala Val Ser Glu His Gln Leu Leu His Asp Lys Gly Lys Ser Ile Gln
1               5                   10                  15

Asp Leu Arg Arg Ala Glu Leu Leu Glu Lys Leu Leu Glu Lys Leu His
            20                  25                  30

Thr Ala

<210> SEQ ID NO 114
<211> LENGTH: 34
<212> TYPE: PRT
<213> ORGANISM: Artificial Sequence
<220> FEATURE:
<223> OTHER INFORMATION: modified human PTHrP

<400> SEQUENCE: 114

Ala Val Ser Glu Ala Gln Leu Leu His Asp Leu Gly Lys Ser Ile Gln
1               5                   10                  15

Asp Leu Arg Arg Arg Glu Leu Leu Glu Lys Leu Leu Glu Lys Leu His
            20                  25                  30

Ala Leu

<210> SEQ ID NO 115
<211> LENGTH: 34
<212> TYPE: PRT
<213> ORGANISM: Artificial Sequence
<220> FEATURE:
<223> OTHER INFORMATION: modified human PTHrP

<400> SEQUENCE: 115

Ala Val Ser Glu His Gln Leu Leu His Asp Lys Gly Lys Ser Ile Gln
1               5                   10                  15

Asp Leu Arg Arg Arg Glu Leu Leu Glu Arg Leu Leu Glu Arg Leu His
            20                  25                  30

Thr Ala

<210> SEQ ID NO 116
<211> LENGTH: 33
<212> TYPE: PRT
<213> ORGANISM: Artificial Sequence
<220> FEATURE:
<223> OTHER INFORMATION: modified human PTHrP

<400> SEQUENCE: 116

Ala Val Ser Glu His Gln Leu Leu His Asp Arg Gly Arg Ser Ile Gln
1               5                   10                  15

Asp Arg Arg Arg Glu Leu Leu Glu Arg Leu Leu Glu Arg Leu His Thr
            20                  25                  30

Ala

<210> SEQ ID NO 117
<211> LENGTH: 34
<212> TYPE: PRT
<213> ORGANISM: Artificial Sequence
<220> FEATURE:
<223> OTHER INFORMATION: modified human PTHrP

<400> SEQUENCE: 117

Ala Val Ser Glu His Gln Leu Leu His Asp Arg Gly Lys Ser Ile Gln
1               5                   10                  15

Asp Leu Arg Arg Arg Glu Leu Leu Glu Arg Leu Leu Lys Arg Leu His
            20                  25                  30

Thr Ala

<210> SEQ ID NO 118
<211> LENGTH: 34
<212> TYPE: PRT
<213> ORGANISM: Artificial Sequence
<220> FEATURE:
<223> OTHER INFORMATION: modified human PTHrP

<400> SEQUENCE: 118

Ala Val Ser Glu His Gln Leu Leu His Asp Arg Gly Arg Ser Ile Gln
1               5                   10                  15

Asp Leu Arg Arg Arg Glu Leu Leu Glu Arg Leu Leu Lys Arg Leu His
            20                  25                  30

Thr Ala

<210> SEQ ID NO 119
<211> LENGTH: 34
<212> TYPE: PRT
<213> ORGANISM: Artificial Sequence
<220> FEATURE:
<223> OTHER INFORMATION: modified human PTHrP

```
<400> SEQUENCE: 119

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala Leu His
            20                  25                  30

Thr Ala

<210> SEQ ID NO 120
<211> LENGTH: 34
<212> TYPE: PRT
<213> ORGANISM: Artificial Sequence
<220> FEATURE:
<223> OTHER INFORMATION: modified human PTHrP

<400> SEQUENCE: 120

Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Ser Leu His
            20                  25                  30

Thr Ala

<210> SEQ ID NO 121
<211> LENGTH: 34
<212> TYPE: PRT
<213> ORGANISM: Artificial Sequence
<220> FEATURE:
<223> OTHER INFORMATION: modified human PTHrP

<400> SEQUENCE: 121

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys Leu His
            20                  25                  30

Thr Ala

<210> SEQ ID NO 122
<211> LENGTH: 34
<212> TYPE: PRT
<213> ORGANISM: Artificial Sequence
<220> FEATURE:
<223> OTHER INFORMATION: modified human PTHrP

<400> SEQUENCE: 122

Ala Val Ser Glu Ile Gln Phe Met His Asn Leu Gly Lys His Leu Ser
1               5                   10                  15

Ser Met Glu Arg Val Glu Leu Leu Glu Lys Leu Leu Glu Lys Leu His
            20                  25                  30

Asn Tyr

<210> SEQ ID NO 123
<211> LENGTH: 34
<212> TYPE: PRT
<213> ORGANISM: Artificial Sequence
<220> FEATURE:
<223> OTHER INFORMATION: modified human PTHrP

<400> SEQUENCE: 123

Ala Val Ser Glu Ile Gln Phe Met His Asn Leu Gly Lys His Leu Ser
1               5                   10                  15

Ser Met Arg Arg Arg Glu Leu Leu Glu Lys Leu Leu Glu Lys Leu His
            20                  25                  30
```

Asn Tyr

<210> SEQ ID NO 124
<211> LENGTH: 30
<212> TYPE: PRT
<213> ORGANISM: Artificial Sequence
<220> FEATURE:
<223> OTHER INFORMATION: modified human PTH

<400> SEQUENCE: 124

Ser Val Ser Glu Ile Gln Leu Met His Asn Leu Gly Lys His Leu Asn
1               5                   10                  15

Ser Met Glu Arg Val Glu Leu Leu Glu Lys Leu Leu Glu Lys
            20                  25                  30

<210> SEQ ID NO 125
<211> LENGTH: 30
<212> TYPE: PRT
<213> ORGANISM: Artificial Sequence
<220> FEATURE:
<223> OTHER INFORMATION: modified human PTH

<400> SEQUENCE: 125

Ser Val Ser Glu Ile Gln Leu Met His Asn Leu Gly Lys His Leu Asn
1               5                   10                  15

Ser Met Glu Arg Val Glu Leu Leu Glu Lys Leu Leu Lys Lys
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: modified human PTH

<400> SEQUENCE: 126

Ser Val Ser Glu Ile Gln Leu Met His Asn Leu Gly Lys His Leu Asn
1               5                   10                  15

Ser Met Glu Arg Val Ala Leu Ala Glu Ala Leu Ala Glu Ala
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: modified human PTH

<400> SEQUENCE: 127

Ser Val Ser Glu Ile Gln Leu Met His Asn Leu Gly Lys His Leu Asn
1               5                   10                  15

Ser Met Glu Arg Val Ser Leu Leu Ser Ser Leu Leu Ser Ser
            20                  25                  30

<210> SEQ ID NO 128
<211> LENGTH: 34
<212> TYPE: PRT
<213> ORGANISM: Artificial Sequence
<220> FEATURE:
<223> OTHER INFORMATION: modified human PTH

<400> SEQUENCE: 128

Ser Val Ser Glu Ile Gln Leu Met His Asn Leu Gly Lys His Leu Asn
1               5                   10                  15

Ser Met Glu Arg Val Ala Phe Tyr Asp Lys Val Ala Glu Lys Leu His
            20                  25                  30

Asn Phe

<210> SEQ ID NO 129
<211> LENGTH: 24
<212> TYPE: PRT
<213> ORGANISM: Artificial Sequence
<220> FEATURE:
<223> OTHER INFORMATION: modified human PTH

<400> SEQUENCE: 129

Leu Met His Asn Leu Gly Lys His Leu Asn Ser Met Glu Arg Val Glu
1               5                   10                  15

Leu Leu Glu Lys Leu Leu Glu Lys
            20

<210> SEQ ID NO 130
<211> LENGTH: 24
<212> TYPE: PRT
<213> ORGANISM: Artificial Sequence
<220> FEATURE:
<223> OTHER INFORMATION: modified human PTH

<400> SEQUENCE: 130

Leu Met His Asn Leu Gly Lys His Leu Asn Ser Met Glu Arg Val Glu
1               5                   10                  15

Leu Leu Glu Lys Leu Leu Lys Lys
            20

<210> SEQ ID NO 131
<211> LENGTH: 24
<212> TYPE: PRT
<213> ORGANISM: Artificial Sequence
<220> FEATURE:
<223> OTHER INFORMATION: modified human PTH

<400> SEQUENCE: 131

Leu Met His Asn Leu Gly Lys His Leu Asn Ser Met Glu Arg Val Ala
1               5                   10                  15

Leu Ala Glu Ala Leu Ala Glu Ala
            20

<210> SEQ ID NO 132
<211> LENGTH: 24
<212> TYPE: PRT
<213> ORGANISM: Artificial Sequence
<220> FEATURE:
<223> OTHER INFORMATION: modified human PTH

<400> SEQUENCE: 132

Leu Met His Asn Leu Gly Lys His Leu Asn Ser Met Glu Arg Val Ser
1               5                   10                  15

Leu Leu Ser Ser Leu Leu Ser Ser
            20

<210> SEQ ID NO 133
<211> LENGTH: 24
<212> TYPE: PRT
<213> ORGANISM: Artificial Sequence
<220> FEATURE:
<223> OTHER INFORMATION: modified human PTH

<400> SEQUENCE: 133

Leu Met His Asn Leu Gly Lys His Leu Asn Ser Met Glu Arg Val Ala
1               5                   10                  15

Phe Tyr Asp Lys Val Ala Glu Lys
            20

<210> SEQ ID NO 134
<211> LENGTH: 30
<212> TYPE: PRT
<213> ORGANISM: Artificial Sequence
<220> FEATURE:
<223> OTHER INFORMATION: modified human PTHrP

<400> SEQUENCE: 134

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: modified human PTHrP

<400> SEQUENCE: 135

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Lys Lys
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: modified human PTHrP

<400> SEQUENCE: 136

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: modified human PTHrP

<400> SEQUENCE: 137

Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Ser
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: modified human PTHrP -continued

```
<400> SEQUENCE: 138

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys
            20                  25                  30

<210> SEQ ID NO 139
<211> LENGTH: 24
<212> TYPE: PRT
<213> ORGANISM: Artificial Sequence
<220> FEATURE:
<223> OTHER INFORMATION: modified human PTHrP

<400> SEQUENCE: 139

Leu Leu His Asp Lys Gly Lys Ser Ile Gln Asp Leu Arg Arg Arg Glu
1               5                   10                  15

Leu Leu Glu Lys Leu Leu Glu Lys
            20

<210> SEQ ID NO 140
<211> LENGTH: 24
<212> TYPE: PRT
<213> ORGANISM: Artificial Sequence
<220> FEATURE:
<223> OTHER INFORMATION: modified human PTHrP

<400> SEQUENCE: 140

Leu Leu His Asp Lys Gly Lys Ser Ile Gln Asp Leu Arg Arg Arg Glu
1               5                   10                  15

Leu Leu Glu Lys Leu Leu Lys Lys
            20

<210> SEQ ID NO 141
<211> LENGTH: 24
<212> TYPE: PRT
<213> ORGANISM: Artificial Sequence
<220> FEATURE:
<223> OTHER INFORMATION: modified human PTHrP

<400> SEQUENCE: 141

Leu Leu His Asp Lys Gly Lys Ser Ile Gln Asp Leu Arg Arg Arg Ala
1               5                   10                  15

Leu Ala Glu Ala Leu Ala Glu Ala
            20

<210> SEQ ID NO 142
<211> LENGTH: 24
<212> TYPE: PRT
<213> ORGANISM: Artificial Sequence
<220> FEATURE:
<223> OTHER INFORMATION: modified human PTHrP

<400> SEQUENCE: 142

Leu Leu His Asp Lys Gly Lys Ser Ile Gln Asp Leu Arg Arg Arg Ser
1               5                   10                  15

Leu Leu Ser Ser Leu Leu Ser Ser
            20

<210> SEQ ID NO 143
<211> LENGTH: 24
<212> TYPE: PRT
<213> ORGANISM: Artificial Sequence
<220> FEATURE:
<223> OTHER INFORMATION: modified human PTHrP
```

<400> SEQUENCE: 143

Leu Leu His Asp Lys Gly Lys Ser Ile Gln Asp Leu Arg Arg Arg Ala
1               5                   10                  15

Phe Tyr Asp Lys Val Ala Glu Lys
            20

<210> SEQ ID NO 144
<211> LENGTH: 30
<212> TYPE: PRT
<213> ORGANISM: Artificial Sequence
<220> FEATURE:
<223> OTHER INFORMATION: modified human PTHrP

<400> SEQUENCE: 144

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Arg Lys
            20                  25                  30

<210> SEQ ID NO 145
<211> LENGTH: 30
<212> TYPE: PRT
<213> ORGANISM: Artificial Sequence
<220> FEATURE:
<223> OTHER INFORMATION: modified human PTHrP

<400> SEQUENCE: 145

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 146
<211> LENGTH: 33
<212> TYPE: PRT
<213> ORGANISM: Artificial Sequence
<220> FEATURE:
<223> OTHER INFORMATION: modified human PTHrP

<400> SEQUENCE: 146

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr

<210> SEQ ID NO 147
<211> LENGTH: 30
<212> TYPE: PRT
<213> ORGANISM: Artificial Sequence
<220> FEATURE:
<223> OTHER INFORMATION: modified human PTHrP

<400> SEQUENCE: 147

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 148
<211> LENGTH: 30
<212> TYPE: PRT

<213> ORGANISM: Artificial Sequence
<220> FEATURE:
<223> OTHER INFORMATION: modified human PTHrP

<400> SEQUENCE: 148

Ala Val Ser Glu His Gln Leu Leu His Asp Lys Gly Lys Ser Ile Gln
1               5                   10                  15

Asp Leu Ala Arg Arg Glu Leu Leu Glu Lys Leu Leu Glu Lys
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: modified human PTHrP

<400> SEQUENCE: 149

Ala Val Ser Glu His Gln Leu Leu His Asp Lys Gly Lys Ser Ile Gln
1               5                   10                  15

Asp Leu Arg Arg Ala Glu Leu Leu Glu Lys Leu Leu Glu Lys
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: modified human PTHrP

<400> SEQUENCE: 150

Ala Val Ser Glu Ala Gln Leu Leu His Asp Leu Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 151
<211> LENGTH: 30
<212> TYPE: PRT
<213> ORGANISM: Artificial Sequence
<220> FEATURE:
<223> OTHER INFORMATION: modified human PTHrP

<400> SEQUENCE: 151

Ala Val Ser Glu His Gln Leu Leu His Asp Lys Gly Lys Ser Ile Gln
1               5                   10                  15

Asp Leu Arg Arg Arg Glu Leu Leu Glu Arg Leu Leu Glu Arg
            20                  25                  30

<210> SEQ ID NO 152
<211> LENGTH: 29
<212> TYPE: PRT
<213> ORGANISM: Artificial Sequence
<220> FEATURE:
<223> OTHER INFORMATION: modified human PTHrP

<400> SEQUENCE: 152

Ala Val Ser Glu His Gln Leu Leu His Asp Arg Gly Arg Ser Ile Gln
1               5                   10                  15

Asp Arg Arg Arg Glu Leu Leu Glu Arg Leu Leu Glu Arg
            20                  25

<210> SEQ ID NO 153
<211> LENGTH: 30

```
<212> TYPE: PRT
<213> ORGANISM: Artificial Sequence
<220> FEATURE:
<223> OTHER INFORMATION: modified human PTHrP

<400> SEQUENCE: 153

Ala Val Ser Glu His Gln Leu Leu His Asp Arg Gly Lys Ser Ile Gln
1               5                   10                  15

Asp Leu Arg Arg Arg Glu Leu Leu Glu Arg Leu Leu Lys Arg
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: modified human PTHrP

<400> SEQUENCE: 154

Ala Val Ser Glu His Gln Leu Leu His Asp Arg Gly Arg Ser Ile Gln
1               5                   10                  15

Asp Leu Arg Arg Arg Glu Leu Leu Glu Arg Leu Leu Lys Arg
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: modified human PTHrP

<400> SEQUENCE: 155

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: modified human PTHrP

<400> SEQUENCE: 156

Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Ser
            20                  25                  30

<210> SEQ ID NO 157
<211> LENGTH: 30
<212> TYPE: PRT
<213> ORGANISM: Artificial Sequence
<220> FEATURE:
<223> OTHER INFORMATION: modified human PTHrP

<400> SEQUENCE: 157

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys
            20                  25                  30

<210> SEQ ID NO 158
```

```
<211> LENGTH: 30
<212> TYPE: PRT
<213> ORGANISM: Artificial Sequence
<220> FEATURE:
<223> OTHER INFORMATION: modified human PTHrP

<400> SEQUENCE: 158

Ala Val Ser Glu Ile Gln Phe Met His Asn Leu Gly Lys His Leu Ser
1               5                   10                  15

Ser Met Glu Arg Val Glu Leu Leu Glu Lys Leu Leu Glu Lys
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: modified human PTHrP

<400> SEQUENCE: 159

Ala Val Ser Glu Ile Gln Phe Met His Asn Leu Gly Lys His Leu Ser
1               5                   10                  15

Ser Met Arg Arg Arg Glu Leu Leu Glu Lys Leu Leu Glu Lys
            20                  25                  30

<210> SEQ ID NO 160
<211> LENGTH: 39
<212> TYPE: PRT
<213> ORGANISM: Artificial Sequence
<220> FEATURE:
<223> OTHER INFORMATION: TIP39

<400> SEQUENCE: 160

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val Leu Asp Ala Pro
        35

<210> SEQ ID NO 161
<211> LENGTH: 34
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (34)..(34)
<223> OTHER INFORMATION: Optional linker and Fc domain attached at the C-terminus

<400> SEQUENCE: 161

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 162
<211> LENGTH: 34
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (34)..(34)
```

<223> OTHER INFORMATION: Optional linker and Fc domain attached at the C-terminus

<400> SEQUENCE: 162

Ser Val Ser Glu Ile Gln Leu Met His Asn Arg Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 163
<211> LENGTH: 34
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (34)..(34)
<223> OTHER INFORMATION: Optional linker and Fc domain attached at the C-terminus

<400> SEQUENCE: 163

Ser Val Ser Glu Ile Gln Leu Met His Asn Lys Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 164
<211> LENGTH: 34
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (34)..(34)
<223> OTHER INFORMATION: Optional linker and Fc domain attached at the C-terminus

<400> SEQUENCE: 164

Ser Val Ser Glu Ile Gln Leu Met His Asn Leu Gly Lys His Leu Asn
1               5                   10                  15

Ser Met Arg Arg Val Glu Trp Leu Arg Lys Lys Leu Gln Asp Val His
                20                  25                  30

Asn Phe

<210> SEQ ID NO 165
<211> LENGTH: 31
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (31)..(31)
<223> OTHER INFORMATION: Optional linker and Fc domain attached at the C-terminus

<400> SEQUENCE: 165

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
                20                  25                  30

<210> SEQ ID NO 166
<211> LENGTH: 30
<212> TYPE: PRT
<213> ORGANISM: Artificial Sequence
<220> FEATURE:

<223> OTHER INFORMATION: Preferred embodiments - PTH
<221> NAME/KEY: misc_feature
<222> LOCATION: (30)..(30)
<223> OTHER INFORMATION: Optional linker and Fc domain attached at the C-terminus

<400> SEQUENCE: 166

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 167
<211> LENGTH: 29
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (1)..(1)
<223> OTHER INFORMATION: Fc domain attached at the N-terminus through optional linker

<400> SEQUENCE: 167

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 168
<211> LENGTH: 28
<212> TYPE: PRT
<213> ORGANISM: Artificial Sequence
<220> FEATURE:
<223> OTHER INFORMATION: Preferred embodiments - PTH
<221> NAME/KEY: misc_feature
<222> LOCATION: (1)..(1)
<223> OTHER INFORMATION: Fc domain attached at the N-terminus through optional linker

<400> SEQUENCE: 168

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 169
<211> LENGTH: 28
<212> TYPE: PRT
<213> ORGANISM: Artificial Sequence
<220> FEATURE:
<223> OTHER INFORMATION: Preferred embodiments - PTHrP
<221> NAME/KEY: misc_feature
<222> LOCATION: (28)..(28)
<223> OTHER INFORMATION: Optional linker and Fc domain attached at the C-terminus

<400> SEQUENCE: 169

Leu Leu His Asn Leu Gly Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 170
<211> LENGTH: 39
<212> TYPE: PRT
<213> ORGANISM: Artificial Sequence
<220> FEATURE:
<223> OTHER INFORMATION: Preferred embodiments - TIP39
<221> NAME/KEY: misc_feature
<222> LOCATION: (39)..(39)

```
<223> OTHER INFORMATION: Optional linker and Fc domain attached at the C-terminus

<400> SEQUENCE: 170

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
                20                  25                  30

Leu Leu Val Leu Asp Ala Pro
            35
```

MODULATORS OF RECEPTORS FOR PARATHYROID HORMONE AND PARATHYROID HORMONE-RELATED PROTEIN

This application claims the benefit of U.S. Provisional Application No. 60/266,673, filed Feb. 6, 2001, U.S. Provisional Application No. 60/214,860, filed Jun. 28, 2000, and U.S. Provisional Application No. 60/200,053, filed Apr. 27, 2000, which are hereby incorporated by reference.

BACKGROUND OF THE INVENTION

Parathyroid hormone (PTH) and parathyroid hormone-related protein (PTHrP) play important physiological roles in calcium homeostasis and in development, respectively. Calcium concentration in the blood is tightly regulated, due to the essential role of calcium in cell metabolism. PTH is an endocrine hormone which is secreted from the parathyroid gland in response to decreased serum calcium levels. PTH acts directly to increase bone resorption and to stimulate renal calcium reabsorption, thus increasing or preserving circulating calcium stores. PTH also indirectly increases calcium absorption in the gut by stimulating the renal hydroxylation of vitamin D.

Both primary and secondary hyperparathyroidism are conditions that are associated with excessive levels of circulating parathyroid hormone. Through the aforementioned pathways, excess PTH levels can cause hypercalcemia and osteopenia. Bone resorption inhibitors such as bisphosphonates and OPG can effectively protect bone and can inhibit the skeleton's contribution to hypercalcemia. However, the calcemic effects of hyperparathyroidism on the kidney and gut are not addressed by currently available therapy.

PTHrP is produced by many cell types, and plays an important role in regulating skeletal development. Postnatally, the roles for PTHrP are less clearly defined. Circulating levels of PTHrP are essentially non-detectable in normal healthy adults. However, many tumors of diverse embryological origins produce and secrete PTHrP in quantities sufficient to cause hypercalcemia. In fact, humoral hypercalcemia of malignancy (HHM) is the most common paraneoplastic syndrome, which accounts for significant patient morbidity and mortality.

Currently, HHM is treated with saline hydration followed by bone resorption inhibitors such as bisphosphonates. This treatment regimen typically takes 3–4 days to achieve significant reductions in serum calcium, and the effects are relatively short-lived (less than one month). For patients with high circulating levels of PTHrP, the effects of current treatment options are even less impressive. Repeated administration of conventional therapies are usually progressively less effective. These limitations to current therapy strongly indicate an unmet medical need for rapid, effective, and long-lasting treatments for HHM.

A major reason for the limited benefits of current HHM therapy is the failure to directly inhibit PTHrP, which is very well established as the principal pathophysiologic factor in HHM. Bone resorption inhibitors such as bisphosphonates only inhibit bone resorption, while PTHrP also has significant calcemic effects on the kidney and the gut. Total neutralization of PTHrP would be the ideal adjuvant therapeutic approach to treatment of HHM.

Both PTH and PTHrP interact with PTH-1 receptor, which accounts for most of their known effects. Mannstadt et al. (1999), *Am. T. Physiol.* 277. 5Pt 2. F665–75 (1999). Only PTH interacts with the newly discovered PTH-2 receptor. Id. PTHrP can be changed to a PTH-2 receptor agonist, however, by changing two residues to the residues at those positions in PTH. Gardella et al. (1996), *J. Biol. Chem.* 271 (33): 19888–93.

An N-terminal fragment of PTH has been used as a therapeutic agent. Intermittently administered native PTH-(1–84) exhibits osteogenic properties, and it has been recognized for decades that these properties can be fully realized with the C-terminally truncated fragment PTH-(1–34). Both peptides bind and activate the PTH-1 receptor with similar affinities, causing the activation of adenylate cyclase (AC) as well as phospholipase C (PLC). AC activation through PTH-1 receptor generates cAMP, while PLC activation through PTH-1 receptor generates PKC and intracellular calcium transients. PTH-(1–34) can maximally activate both the AC and the PLC pathways. It has been demonstrated that the anabolic effects of PTH-(1–34) require short intermittent (daily) exposures Dobnig (1998), *Endocrinol.* 138: 4607–12. In human trials on postmenopausal women, daily subcutaneous injection of low doses of PTH(1–34) were shown to result in impressive bone formation in the spine and femoral neck with significant reduction in incidence of vertebral fractures. These clinical data reveal PTH as one of the most efficacious agents tested for osteoporosis.

Truncated PTH fragments have diminished AC/cAMP activation and similarly diminished anabolic activity. Rixon et al. (1994), *J. Bone Min. Res.* 9: 1179–89; Hilliker et al. (1996), Bone 19: 469–477; Lane et al. (1996), *J. Bone Min. Res.* 11: 614–25. Such truncated PTH fragments have this diminished activity (Rixon et al. (1994); Hilliker et al. (1996); Lane et al. (1996)) even if they maintain full agonism towards PKC. Rixon et al., (1994). These observations have led to the proposal that the AC/cAMP pathway is critical for the bone anabolic properties of PTH, while the PLC/PKC pathway is dispensable in this regard. Rixon et al, (1994); Whitfield et al. (1996), *Calcified Tissue International* 53: 81–7.

An opposing, but not mutually exclusive, theory suggests that PLC activation (in addition to AC) might also be an important property of anabolic PTH fragments. Takasu (1998), *Endocrinol.* 139: 4293–9. The apparent absence of PLC activation by some anabolic C-terminally truncated PTH peptides may be an artifact of insensitive assay methods combined with lower receptor binding. Takasu (1998). Progressive truncations from the C-terminus of PTH-(1–34) result in stepwise reductions in binding affinity for the PTH1R Takasu (1998). PKC activation through PTH-1 receptor appears to be acutely sensitive to binding affinity and to receptor density (Guo et al. (1995), *Endocrinol* 136: 3884–91), whereas cAMP activation is far less sensitive to these variables. As such, hPTH-(1–31) has a slightly reduced (1–6 fold) affinity for PTH-1 receptor compared to hPTH-(1–34), while hPTH-(1–30) has a significantly reduced (10–100 fold) affinity Takasu (1998). Perhaps due to this decreased PTH-1 receptor affinity, PTH-(1–30) is a weak and incomplete agonist for PLC activation via the rat PTH-1 receptor.

Compared to PTH-(1–34), PTH-(1–31) has similar or slightly reduced anabolic potential (Rixon et al. (1994); Whitfield et al. (1996), *Calcified Tissue International* 53: 81–7; Whitfield et al. (1996), *Calcified Tissue International* 65:143–7), binding affinity for PTH1R, and cAMP induction (Takasu (1998)). PTH-(1–31) also has slightly reduced PLC activation. Takasu (1998). In healthy humans, infusion of PTH-(1–31) and PTH-(1–34) had similar stimulatory effects on plasma and urinary CAMP concentration, but unlike PTH-(1–34), PTH-(1–31) failed to elevate serum calcium, plasma 1,25(OH)2D3, or urinary N-TX levels. Fraher et al. (1999), *J. Clin. Endocrin. Met.* 84: 2739–43. These data suggest that PTH-(1–31) has diminished capacity to induce bone resorption and to stimulation vitamin D synthesis, which is a favorable profile for bone anabolic agents.

PTH-(1–30) was initially shown to lack anabolic properties Whitfield et al. (1996), *Calcified Tissue International* 53: 81–7. More recently, however, it has been demonstrated that PTH-(1–30) is anabolic when administered at very high doses (400–2,000 μg/kg, vs. 80 μg/kg for PTH-(1–34)). The lower potency of PTH-(1–30) could be predicted by its lower binding affinity for PTH-1 receptor, its diminished CAMP activation, and/or to its greatly diminished PKC activation. Takasu (1998). It remains to be determined whether PTH-(1–30) has a similar or even more desirable reduction in apparent bone resorption activity.

PTH-(1–28) is the smallest reported fragment to fully activate CAMP. Neugebauer et al. (1995), *Biochem.* 34: 8835–42. However, hPTH-(1–28) was initially reported to have no osteogenic effects in OVX rats. Miller et al. (1997), *J. Bone Min. Res.* 12: S320 (Abstract). Recently, a very high dose of PTH-(1–28) (1,000 μg/kg/day) was shown to be anabolic in OVX rats, whereas 200 μg/kg/day was ineffective. Whitfield et al. (2000), *J. Bone Min. Res.* 15: 964–70. The diminished or absent anabolic effects of some truncated PTH fragments has been attributed to rapid clearance in vivo. Rixon et al. (1994).

Recombinant and modified proteins are an emerging class of therapeutic agents. Useful modifications of protein therapeutic agents include combination with the "Fc" domain of an antibody and linkage to polymers such as polyethylene glycol (PEG) and dextran. Such modifications are discussed in detail in a patent application entitled, "Modified Peptides as Therapeutic Agents," U.S. Ser. No. 09/428,082, PCT appl. no. WO 99/25044, which is hereby incorporated by reference in its entirety.

A much different approach to development of therapeutic agents is peptide library screening. The interaction of a protein ligand with its receptor often takes place at a relatively large interface. However, as demonstrated for human growth hormone and its receptor, only a few key residues at the interface contribute to most of the binding energy. Clackson et al. (1995), *Science* 267: 383–6. The bulk of the protein ligand merely displays the binding epitopes in the right topology or serves functions unrelated to binding. Thus, molecules of only "peptide" length (2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display peptide libraries have emerged as a powerful method in identifying such peptide agonists and antagonists. See, for example, Scott et al. (1990), *Science* 249: 386; Devlin et al. (1990), *Science* 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, e.g., Cwirla et al. (1997), *Science* 276: 1696–9, in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman (1997), *Ann. Rev. Biophys. Biomol. Struct.* 26: 401–24.

Structural analysis of protein—protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al. (1997), *Nature Biotech.* 15: 1266–70. These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ peptides linked to RNA; for example, PROfusion technology, Phylos, Inc. See, for example, Roberts & Szostak (1997), *Proc. Natl. Acad. Sci. USA*, 94: 12297–303. Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells & Lowman (1992), *Curr. Opin. Biotechnol.* 3: 355–62. Conceptually, one may discover peptide mimetics of any protein using phage display, RNA-peptide screening, and the other methods mentioned above.

SUMMARY OF THE INVENTION

The present invention concerns therapeutic agents that modulate the activity of PTH and PTHrP. In accordance with the present invention, modulators of PTH and PTHrP comprise:

a) a PTH/PTHrP modulating domain, preferably the amino acid sequence of PTH/PTHrP modulating domains of PTH and/or PTHrP, or sequences derived therefrom by phage display, RNA-peptide screening, or the other techniques mentioned above; and b) a vehicle, such as a polymer (e.g., PEG or dextran) or an Fc domain, which is preferred;

wherein the vehicle is covalently attached to the carboxyl terminus of the PTH/PTHrP modulating domain. The preferred vehicle is an Fc domain, and the preferred Fc domain is an IgG Fc domain. Preferred PTH/PTHrP modulating domains comprise the PTH and PTHrP-derived amino acid sequences described hereinafter. Other PTH/PTHrP modulating domains can be generated by phage display, RNA-peptide screening and the other techniques mentioned herein. Such peptides typically will be antagonists of both PTH and PTHrP, although such techniques can be used to generate peptide sequences that serve as selective inhibitors (e.g., inhibitors of PTH but not PTHrP).

Further in accordance with the present invention is a process for making PTH and PTHrP modulators, which comprises:

a) selecting at least one peptide that binds to the PTH-1 or PTH-2 receptor; and b) covalently linking said peptide to a vehicle.

The preferred vehicle is an Fc domain. Step (a) is preferably carried out by selection from the peptide sequences in Tables 1 and 2 hereinafter or from phage display, RNA-peptide screening, or the other techniques mentioned herein.

The compounds of this invention may be prepared by standard synthetic methods, recombinant DNA techniques, or any other methods of preparing peptides and fusion proteins. Compounds of this invention that encompass non-peptide portions may be synthesized by standard organic chemistry reactions, in addition to standard peptide chemistry reactions when applicable.

The primary use contemplated for the compounds of this invention is as therapeutic or prophylactic agents. The vehicle-linked peptide may have activity comparable to—or even greater than—the natural ligand mimicked by the peptide.

The compounds of this invention may be used for therapeutic or prophylactic purposes by formulating them with appropriate pharmaceutical carrier materials and administering an effective amount to a patient, such as a human (or other mammal) in need thereof. Other related aspects are also included in the instant invention.

Of particular interest in the present invention are molecules comprising PTH/PTHRP modulating domains having a shortened PTH C-terminal sequence, such as PTH-(1–28) or (1–34). The prior art shows no anabolic studies using sustained duration delivery of such C-terminally truncated PTH fragments. Although the art does not suggest it, molecules comprising smaller fragments such as PTH-(1–30)-Fc can be anabolic on their own. Despite their weak agonism towards PLC (see Background of the Invention), hPTH-(1–30) is nearly as effective at CAMP stimulation as is hPTH-(1–34). While not wanting to be constrained by theory, the inventors note that the anabolic properties of PTH fragments may be selectively related to their CAMP activation, rather than PLC activation, so that PTH fragments with reduced receptor affinity will have a favorable anabolic profile. It is possible that continuous exposure to truncated PTH fragments would have a different, and more favorable effect on bone compared to continuous exposure to PTH-(1–34) or PTH-(1–84) that has been demonstrated in humans by Fraher et al. (1999).

Numerous additional aspects and advantages of the present invention will become apparent upon consideration of the figures and detailed description of the invention.

BRIEF DESCRIPTION OF THE FIGURES

A: Single disulfide-bonded dimers. IgG1 antibodies typically have two disulfide bonds at the hinge region between the constant and variable domains. The Fc domain in FIG. 1A may be formed by truncation between the two disulfide bond sites or by substitution of a cysteinyl residue with an unreactive residue (e.g., alanyl).

B: Doubly disulfide-bonded dimers. This Fc domain may be formed by truncation of the parent antibody to retain both cysteinyl residues in the Fc domain chains or by expression from a construct including a sequence encoding such an Fc domain.

C: Noncovalent dimers. This Fc domain may be formed by elimination of the cysteinyl residues by either truncation or substitution. One may desire to eliminate the cysteinyl residues to avoid impurities formed by reaction of the cysteinyl residue with cysteinyl residues of other proteins present in the host cell. The noncovalent bonding of the Fc domains is sufficient to hold together the dimer.

Figure 1A:
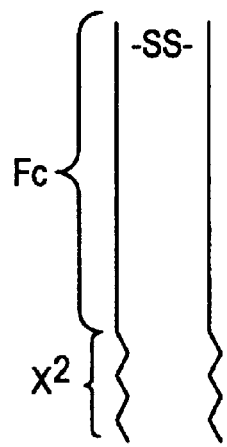
In FIG. 1A, the Fc domain is linked at the C-terminus of the peptide.

D: Single disulfide-bonded dimer as in FIG. 1A except the Fc domain is linked at the N-terminus of the peptide $X^1$.

Figure 1B:
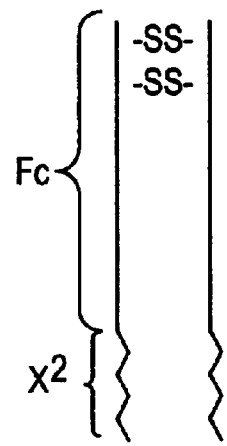
In FIG. 1B, the Fc domain is linked at the C-terminus of the peptide.

E. Doubly disulfide-linked dimers as in FIG. 1B except the Fc domain is linked at the N-terminus of peptide $X^1$.

Figure 1C:
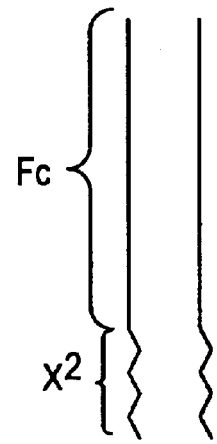
FIG. 1 shows exemplary Fc dimers that may be derived from an IgG1 antibody. "Fc" in the figure represents any of the Fc variants within the meaning of "Fc domain" herein. "$X^1$" and "$X^2$" represent peptides or linker-peptide combinations as defined hereinafter. The specific dimers are as follows.
Figure 1D:
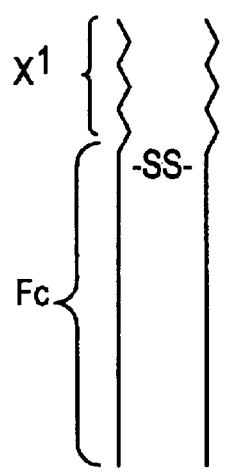
Figure 1E:
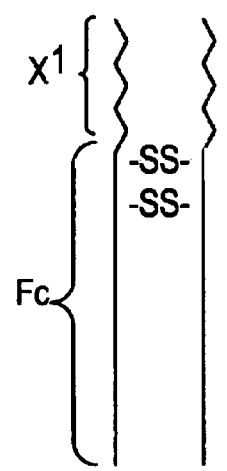
Figure 1F:
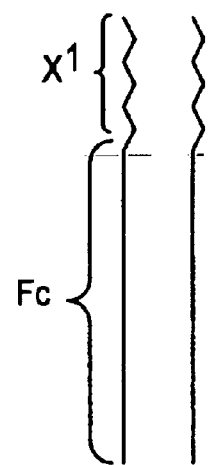

F. Noncovalent dimers as in FIG. 1C except the Fc domain is linked at the N-terminus of peptide $X^1$.

Other dimers may be formed by using Fc domains derived from different types of antibodies (e.g., IgG2, IgM).

Figure 2A:
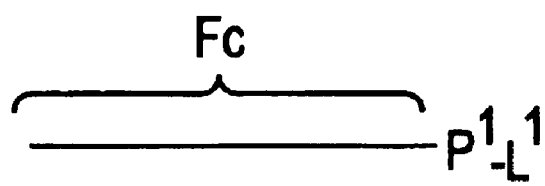
Figure 2B:
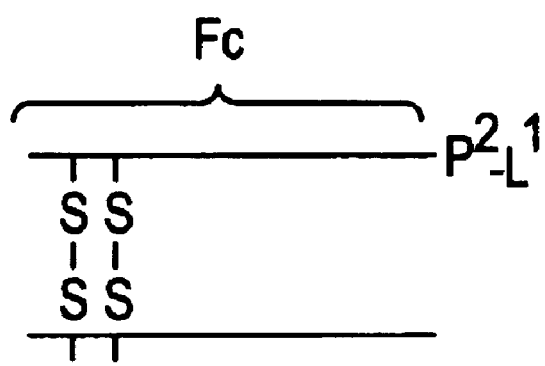
Figure 2C:
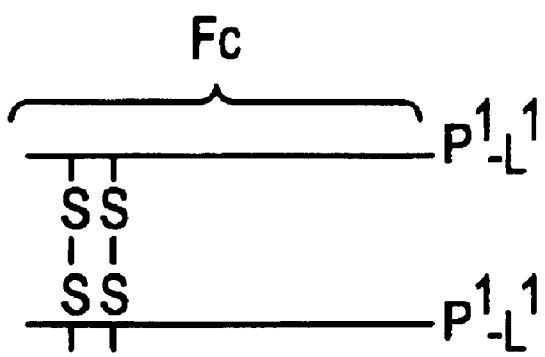

FIG. 2 shows the structure of additional compounds of the invention. FIG. 2A shows a single chain molecule and may also represent the DNA construct for the molecule. FIG. 2B shows a dimer in which the linker-peptide portion is present on only one chain of the dimer. FIG. 2C shows a dimer having the peptide portion on both chains. The dimer of FIG. 2C will form spontaneously in certain host cells upon expression of a DNA construct encoding the single chain as shown in FIG. 3. In other host cells, the cells could be placed in conditions favoring formation of dimers or the dimers can be formed in vitro.

FIGS. 3A, 3B, 3C shows exemplary nucleic acid and amino acid sequences (SEQ ID NOS: 1 and 2, respectively) of human IgG1 Fc that may be used in this invention.

Figure 4:
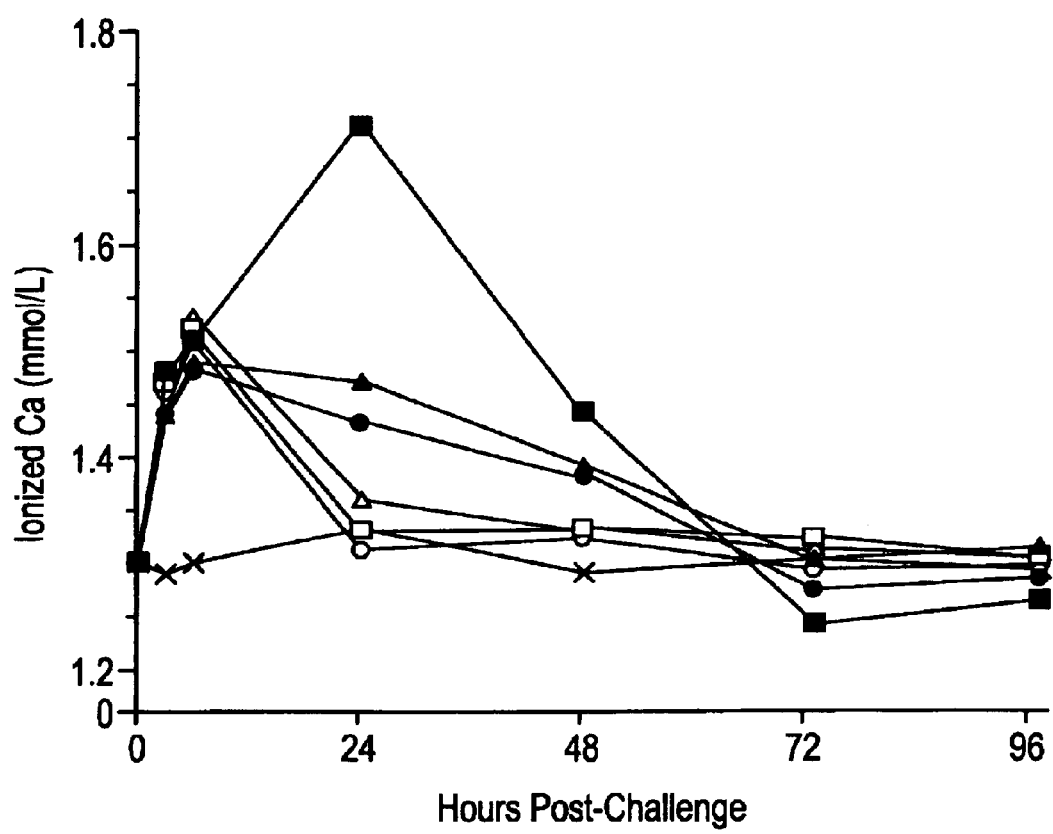

FIG. 4 shows the calcemic response of normal mice to PTH-(1–34) and to PTH-(1–34)-Fc. Mice were challenged with vehicle (PBS, —X—), or with PTH-(1–34) (open symbols) or with PTH-(1–34)-Fc (closed symbols). Doses were 156 nmol/kg (circles), 469 nmol/kg (triangles) or 1,560 nmol/kg (squares). Data represent group means, n=6 mice/group.

Figure 5:
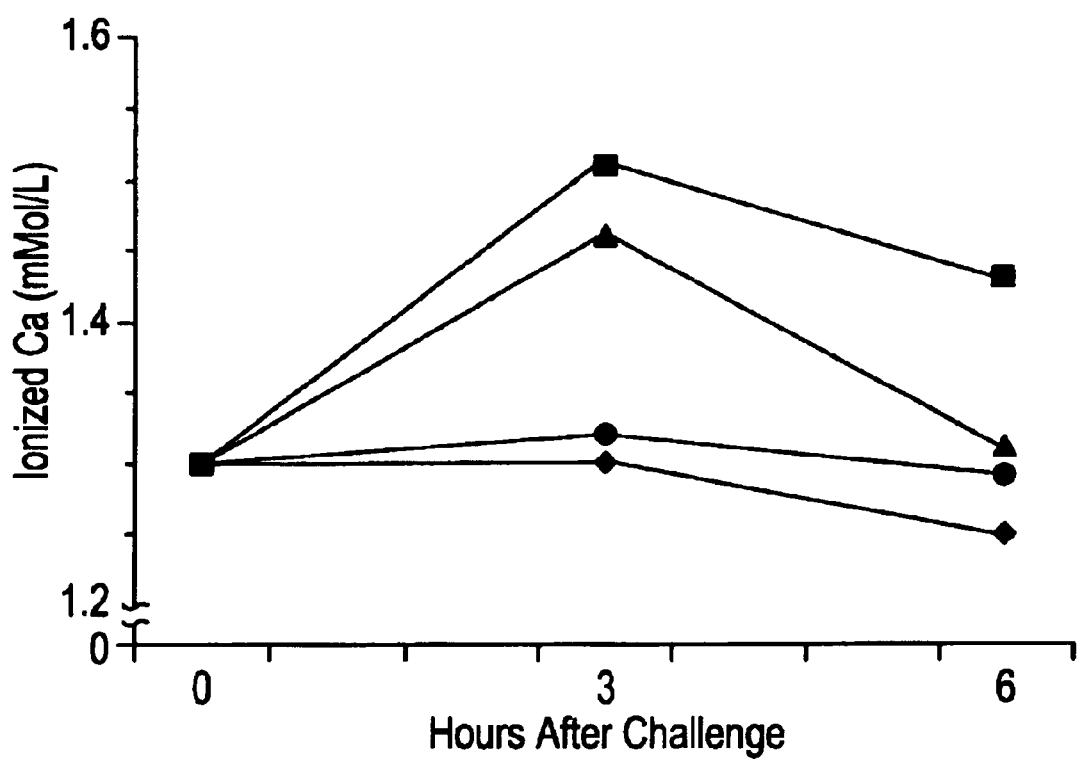

FIG. 5 shows that [Asn10,Leu11]PTHrP-(7–34)-Fc inhibits the calcemic response of normal mice to PTHrP. Normal male mice were injected SC with vehicle (PBS, circles) or with human PTHrP-(1–34) at 0.5 mg/kg (squares). PTHrP-challenged mice were then immediately injected SC with [Asn10,Leu11]PTHrP-(7–34)-Fc at 10 mg/kg (triangles) or 30 mg/kg (diamonds). Data represent group means, with an n of 6 mice/group.

Figure 6:
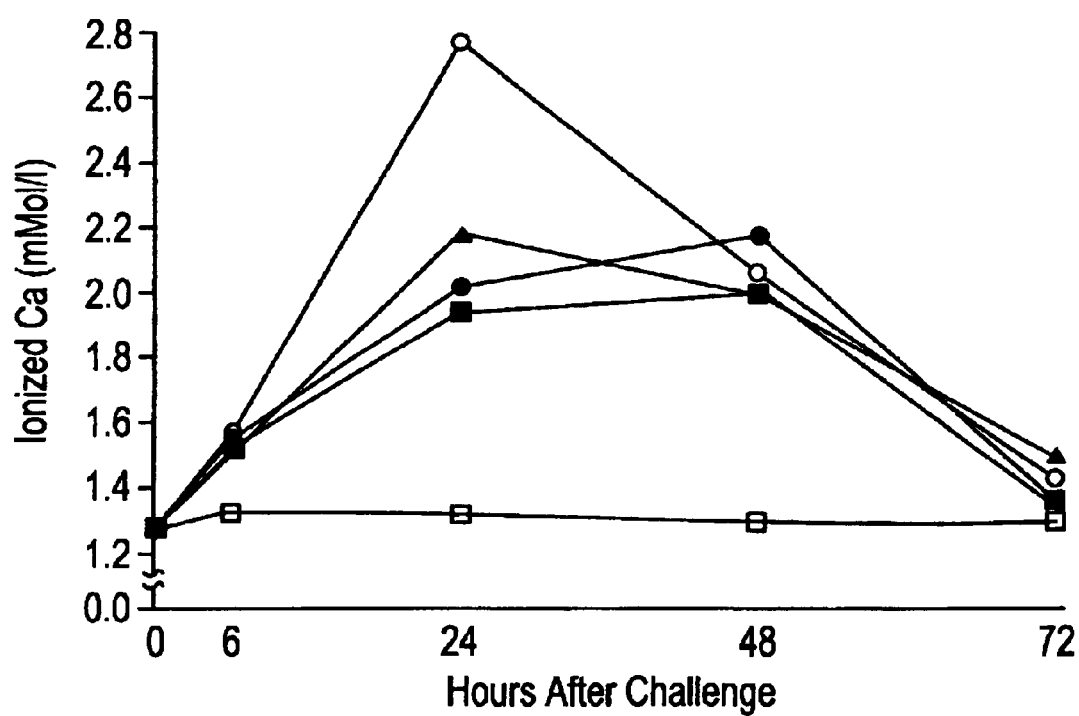

FIG. 6 shows the effect of [Asn10,Leu11]PTHrP-(7–34)-Fc on chronic hypercalcemia induced by PTH-(1–34)-Fc. Normal male mice were challenged once by SC injection with PTH-(1–34)-Fc (30 mg/kg) (open circles), or with vehicle (PBS, open squares). Some PTH-(1–34)-Fcchallenged mice were treated once, at the time of challenge, with [Asn10,Leu11]PTHrP-(7–34)-Fc at 10 (closed triangle), 30 (closed circle), or 100 mg/kg (closed square). All doses of [Asn10,Leu11]PTHrP-(7–34)-Fc caused a significant suppression of PTH-(1–34)-Fc-mediated hypercalcemia. Data represent means±SEM, n=5 mice/group.

Figure 7:
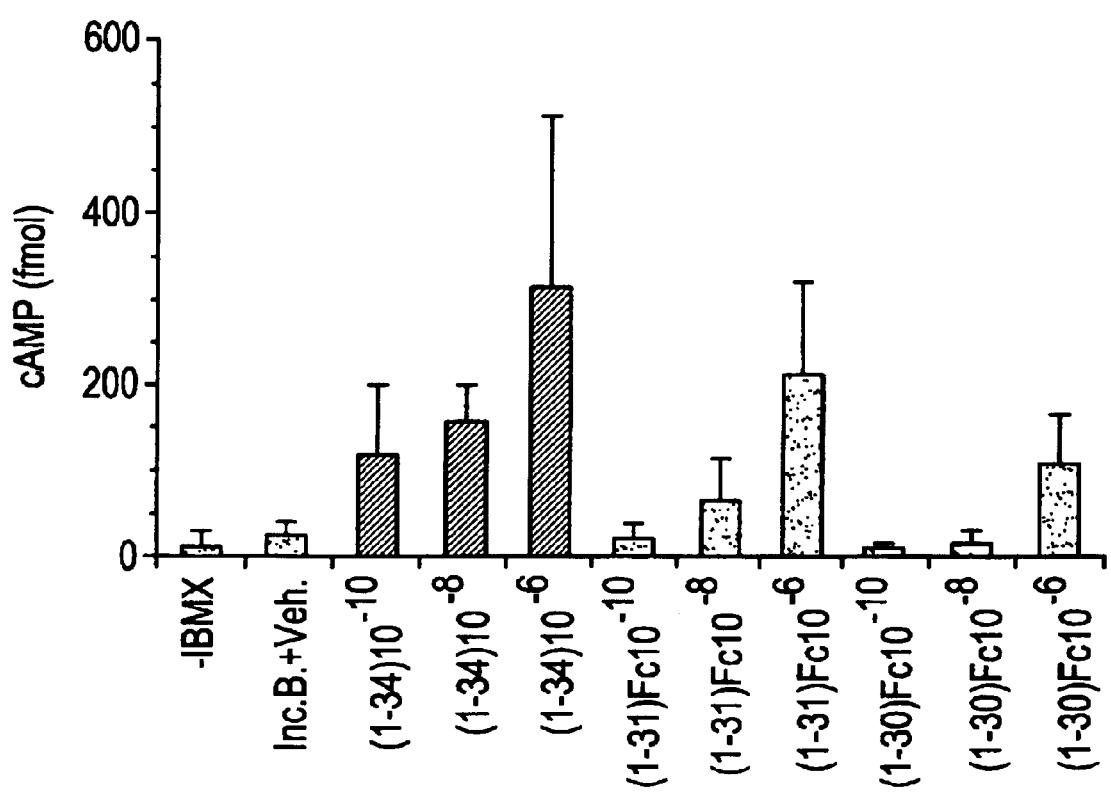

FIG. 7 shows cAMP accumulation in ROS 17/2.8 rat osteoblast-like cells. Cultures were treated with the phosphodiesterase inhibitor IBMX and then challenged for 15 minutes with various PTH fragments. CAMP was measured by ELISA.

cAMP levels are shown for the following cultures:

(-IBMX), without phosphodiesterase inhibitor;

(Inc. B+Veh.), with vehicle (PBS);

$(1-34)^{-10}$, treated with IBMX and challenged with PTH [1–34] at a concentration of $10^{-10}$ M;

$(1-34)10^{-8}$, treated with IBMX and challenged with PTH [1–34] at a concentration of $10^{-8}$ M;

$(1-34)10^{-6}$, treated with IBMX and challenged with PTH [1–34] at a concentration of $10^{-6}$ M;

$(1-31)Fc10^{-10}$, treated with IBMX and challenged with PTH[1–31]-Fc at a concentration of $10^{-10}$ M;

$(1-31)Fc10^{-8}$, treated with IBMX and challenged with PTH[1–31]-Fc at a concentration of $10^{-8}$ M;

$(1-31)Fc10^{-6}$, treated with IBMX and challenged with PTH[1–3]-Fc at a concentration of $10^{-6}$ M;

$(1-30)Fc10^{-10}$, treated with IBMX and challenged with PTH[1–30]-Fc at a concentration of $10^{-10}$ M;

$(1-30)Fc10^{-8}$, treated with IBMX and challenged with PTH[1–30]-Fc at a concentration of $10^{-8}$ M;

$(1-30)Fc10^{-6}$, treated with IBMX and challenged with PTH[1–30]-Fc at a concentration of $10^{-6}$ M.

FIG. 8 shows the effects of single treatments on clinical chemistry. Peripheral blood was obtained daily for 3 days following single subcutaneous injections of the indicated compounds. FIG. 8A shows total serum calcium; FIG. 8B, alkaline phosphatase (AP), a marker of osteoblast activity; FIG. 8C, tartrate-resistant acid phosphatase (TRAP), a marker of osteoclast activity, and FIG. 8D, AP:TRAP ratio, an index of relative osteoblas: osteoclast activity.

Figure 9:
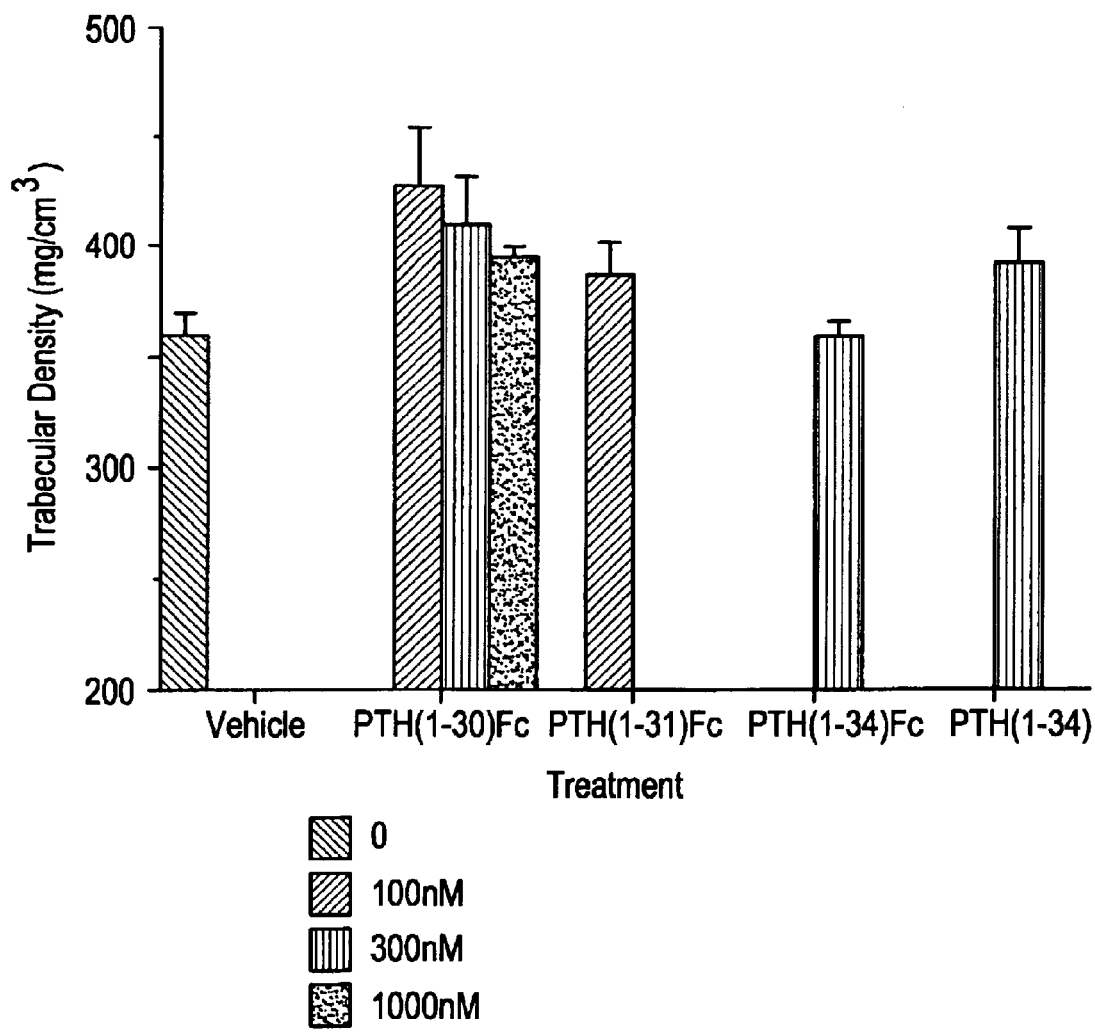

FIG. 9 shows the effects of PTH constructs on bone mineral density. Peripheral quantitative computed tomography (pQCT) was performed on the proximal tibial metaphysis of mice on day 15, after injections of PTH constructs on day 0, 5 and 10.

Figure 10A:
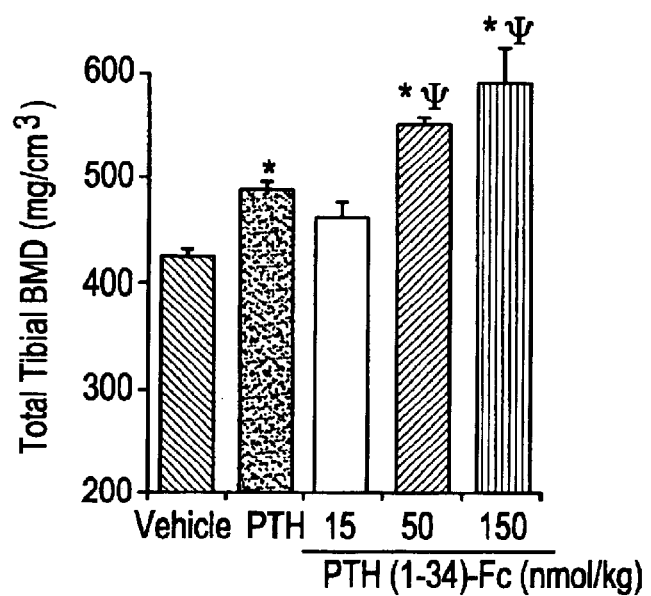
Figure 10B:
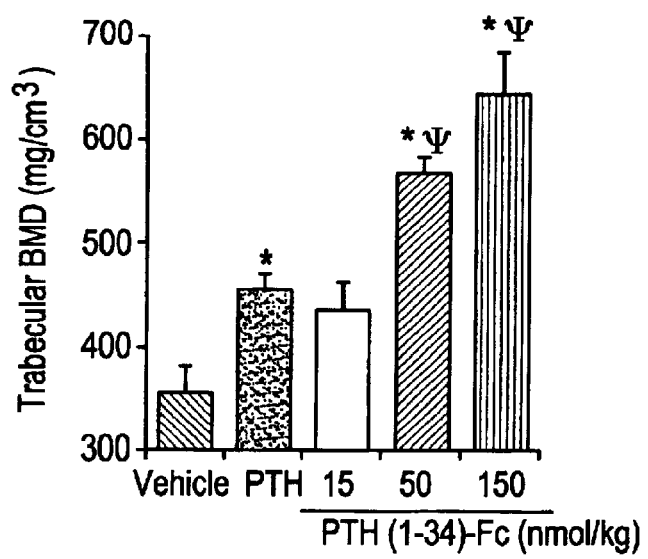
Figure 10C:
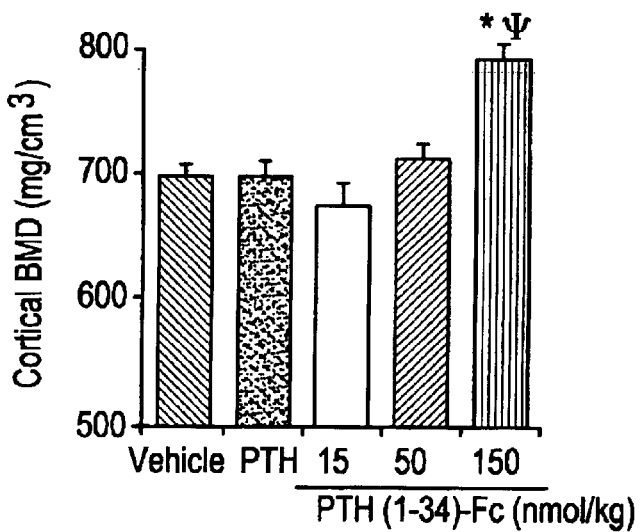
Figure 11A:
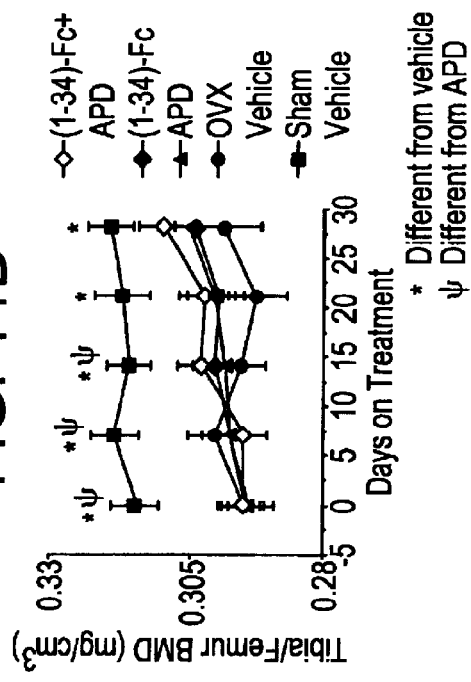
Figure 11B:
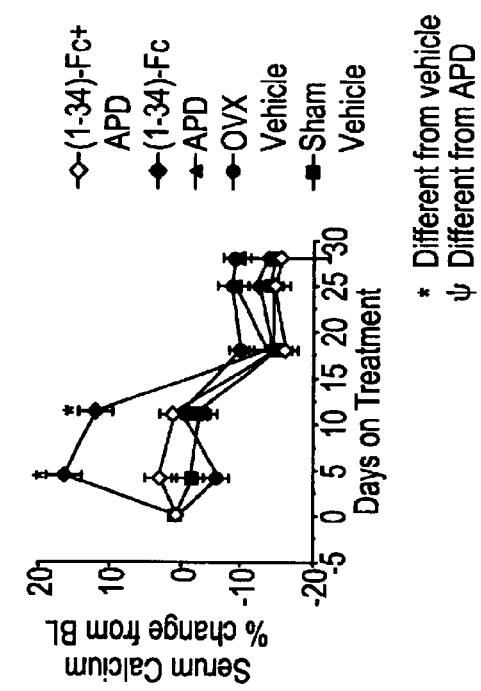
Figure 11C:
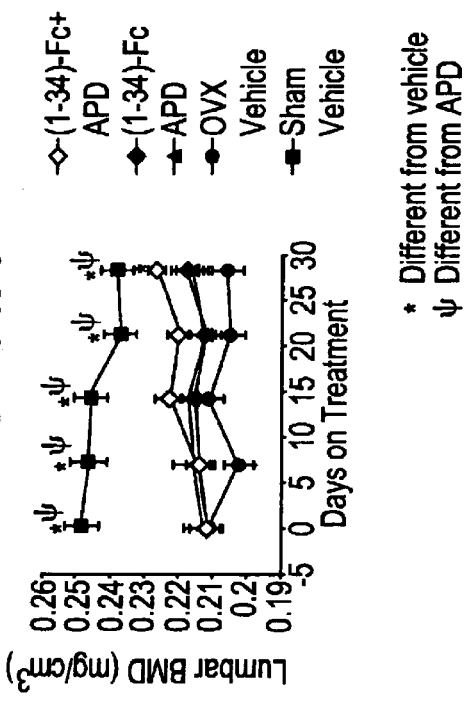
Figure 11D:
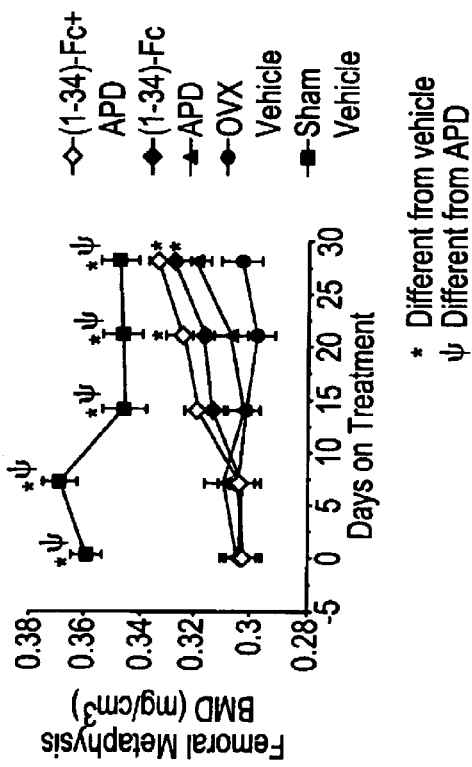

FIG. 10 shows the effect of twice-weekly PTH-(1–34)-Fc versus daily PTH-(1–34) on tibial, trabecular, and cortical bone mineral density (BMD) panels A, B, and C, respectively. Daily PTH [PTH-(1–34)] was given at 80 μg/kg/day (20 nmol/kg/day).

FIG. 11 shows the effects of twice-weekly treatment on BMD and serum calcium in aged ovariectomized (OVX) rats. Eleven months after OVX, rats were treated twice per week with phosphate-buffered saline (PBS, vehicle) or with APD (0.5 mg/kg) or with PTH-(1–34)-Fc (50 nmol/kg). DEXA was performed weekly. Blood was drawn 24 hours after the second weekly injection, when the calcemic effects of PTH-Fc are typically maximal. The effects of PTH-Fc administration on lumbar BMD (FIG. 11A), tibia/femur BMD (FIG. 11B), femoral metaphysis BMD (FIG. 11C), and serum calcium (FIG. 11D) were determined.

Figure 12:
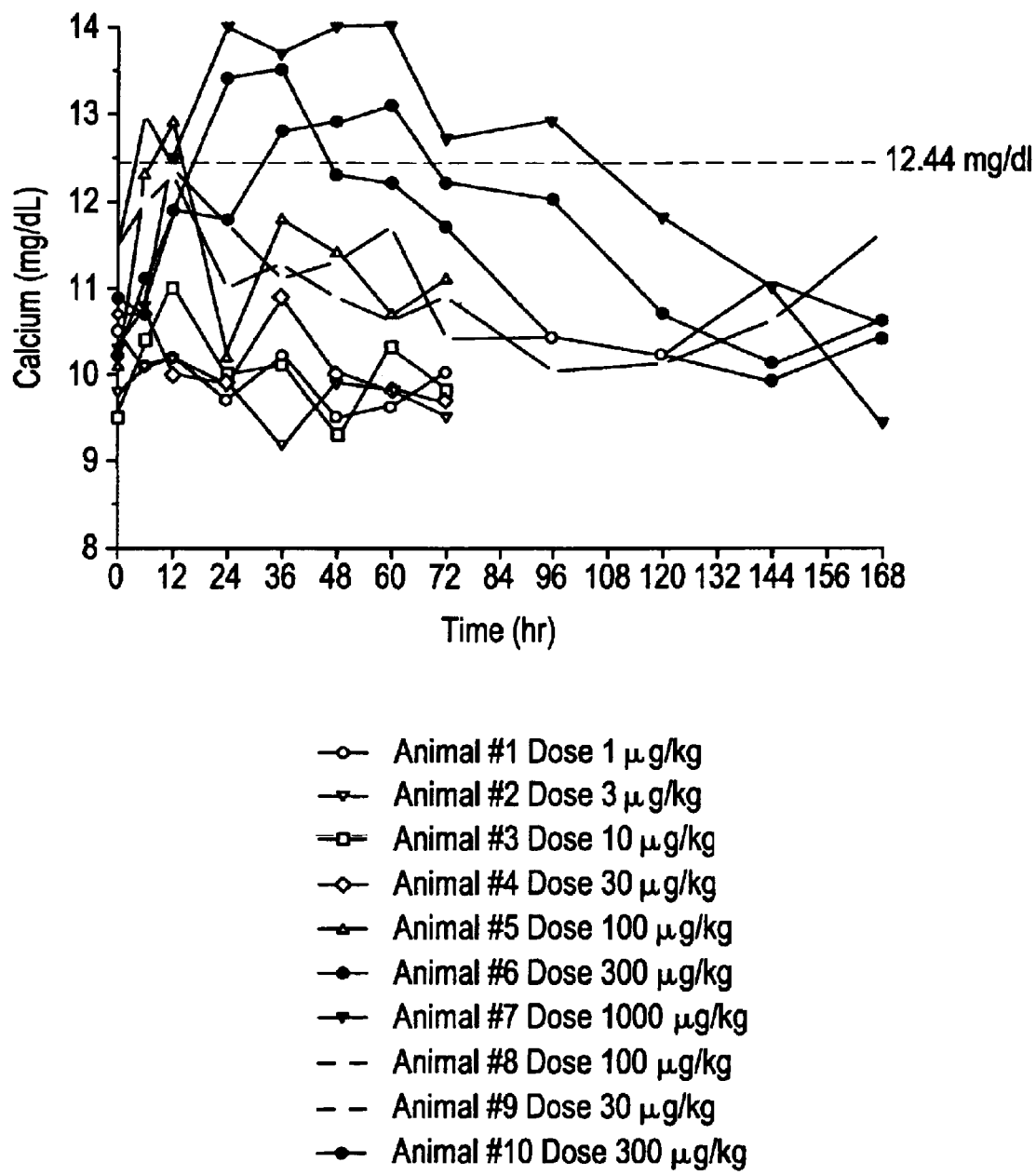

FIG. 12 shows the effect of a single subcutaneous injection of PTH-(1–34)-Fc into OVX cynomolgus monkeys. Monkeys were injected with PTH-(1–34)-Fc at doses of 1–30 μg/kg (n=1/group) or 100–1000 μg/kg (n=2/group). Serum was analyzed for total calcium. The dotted line indicates the threshold for hypercalcemia, based on an elevation of calcium greater than three standard deviations above the normal mean, on two or more consecutive timepoints.

DETAILED DESCRIPTION OF THE INVENTION

Definition of Terms

The terms used throughout this specification are defined as follows, unless otherwise limited in specific instances.

The term "comprising" means that a compound may include additional amino acids on either or both of the N- or C-termini of the given sequence. Of course, these additional amino acids should not significantly interfere with the activity of the compound.

The term "acidic residue" refers to amino acid residues in D- or L-form having sidechains comprising acidic groups. Exemplary acidic residues include D and E.

The term "aromatic residue" refers to amino acid residues in D- or L-form having sidechains comprising aromatic groups. Exemplary aromatic residues include F, Y, and W.

The term "basic residue" refers to amino acid residues in D- or L-form having sidechains comprising basic groups. Exemplary basic residues include H, K, and R.

The terms "hydrophilic residue" and "Haa" refer to amino acid residues in D- or L-form having sidechains comprising at least one hydrophilic functional group or polar group. Exemplary hydrophilic residues include C, D, E, H, K, N, Q, R, S, and T.

The terms "lipophilic residue" and "Laa" refer to amino acid residues in D- or L-form having sidechains comprising uncharged, aliphatic or aromatic groups. Exemplary lipophilic sidechains include F, I, L, M, V, W, and Y. Alanine (A) is amphiphilic—it is capable of acting as a hydrophilic or lipophilic residue. Alanine, therefore, is included within the definition of both "lipophilic residue" and "hydrophilic residue."

The term "nonfunctional residue" refers to amino acid residues in D- or L-form having sidechains that lack acidic, basic, or aromatic groups. Exemplary nonfunctional amino acid residues include M, G, A, V, I, L and norleucine (Nle).

The term "vehicle" refers to a molecule that prevents degradation and/or increases half-life, reduces toxicity, reduces immunogenicity, or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); a carbohydrate or oligosaccharide (e.g., dextran); human serum albumin (HSA) and related molecules; transtheratin (TTR) and related molecules; or any natural or synthetic protein, polypeptide or peptide that binds to a salvage receptor. Vehicles are further described hereinafter.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071–9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently. Thus, exemplary dimers within the scope of this invention are as shown in FIGS. 1 and 2.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N—terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxycarbonyl-NH—, wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) compounds in which individual amino acid moieties are modified through treatment with agents capable of reacting with selected side chains or terminal residues. Derivatives are further described hereinafter.

The term "peptide" refers to molecules of 1 to 85 amino acids, with molecules of 5 to 34 amino acids preferred. Exemplary peptides may comprise the PTH/PTHrP modulating domain of a naturally occurring molecule or comprise randomized sequences.

The term "randomized" as used to refer to peptide sequences refers to fully random sequences (e.g., selected by phage display methods or RNA-peptide screening) and sequences in which one or more residues of a naturally occurring molecule is replaced by an amino acid residue not appearing in that position in the naturally occurring molecule. Exemplary methods for identifying peptide sequences include phage display, *E. coli* display, ribosome display, RNA-peptide screening, chemical screening, and the like.

The term "PTH/PTHrP modulating domain" refers to any amino acid sequence that binds to the PTH-1 receptor and/or the PTH-2 receptor and comprises naturally occurring sequences or randomized sequences. Exemplary PTH/PTHrP modulating domains can be identified or derived as described in the references listed for Tables 1 and 2, which are hereby incorporated by reference in their entirety.

The term "PTH agonist" refers to a molecule that binds to PTH-1 or PTH-2 receptor and increases or decreases one or more PTH activity assay parameters as does full-length native human parathyroid hormone. An exemplary PTH activity assay is disclosed in Example 1.

The term "PTH antagonist" refers to a molecule that binds to PTH-1 or PTH-2 receptor and blocks or prevents the normal effect on those parameters by full length native human parathyroid hormone. An exemplary PTH activity assay is disclosed in Example 2.

The term "bone resorption inhibitor" refers to such molecules as determined by the assays of Examples 4 and 11 of WO 97/23614:, which is hereby incorporated by reference in its entirety. Exemplary bone resorption inhibitors include OPG and OPG-L antibody, which are described in WO 97/23614 and WO98/46751, respectively, which are hereby incorporated by reference in their entirety.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

Structure of Compounds

In General. PTH and PTHrP receptor binding amino acid sequences are described in Tables 1 and 2. Other information on PTH and PTHrP is found in Mannstadt et al. (1999), *Am. J. Physiol.* 277. 5Pt 2: F665–75; and Gardella (1996), *J. Biol. Chem.* 271 (33): 19888–93. Each of these references is hereby incorporated by reference in its entirety.

From the foregoing sequences, the present inventors identified in particular preferred sequences derived from PTH and PTHrP. These sequences can be randomized through the techniques mentioned above by which one or more amino acids may be changed while maintaining or even improving the binding affinity of the peptide.

In the compositions of matter prepared in accordance with this invention, the peptide may be attached to the vehicle through the peptide's C-terminus. Thus, the vehicle-peptide molecules of this invention may be described by the following formula I:

$$P^1\text{-}(L^1)_a\text{-}F^1 \qquad \text{I}$$

and multimers thereof, wherein:

F$^1$ is a vehicle (preferably an Fc domain) and is attached at the C-terminus of P$^1$-(L$^1$)$_a$;

$P^1$ is a sequence of a PTH/PTHrP modulating domain;

$L^1$ is a linker; and a is 0 or 1.

Peptides. Any number of peptides may be used in conjunction with the present invention. Peptides may comprise part of the sequence of naturally occurring proteins, may be randomized sequences derived from the sequence of the naturally occurring proteins, or may be wholly randomized sequences. Phage display and RNA-peptide screening, in particular, are useful in generating peptides for use in the present invention.

A PTH/PTHrP modulating domain sequence particularly of interest is of the formula

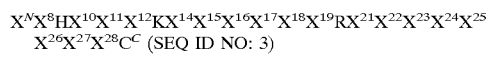
$X^{26}X^{27}X^{28}C^C$ (SEQ ID NO: 3)    II wherein:

$X^N$ is absent or is $X^3X^4X^5X^6X^7$, $X^2X^3X^4X^5X^6X^7$, $X^1X^2X^3X^4X^5X^6X^7$, or $YX^1X^2X^3X^4X^5X^6X^7$;

$X^1$ is an amino acid residue (nonfunctional, hydrophilic or aromatic residue preferred; A, S or Y preferred);

$X^2$ is an amino acid residue (nonfunctional residue preferred, V most preferred);

$X^3$ is an amino acid residue (hydrophilic residue preferred, S most preferred);

$X^4$ is an amino acid residue (acidic residue preferred, E most preferred);

$X^5$ is an amino acid residue (nonfunctional or basic residue preferred, H or I most preferred);

$X^6$ is an amino acid residue (acidic or hydrophilic residue preferred, Q or E most preferred);

$X^7$ is an amino acid residue (nonfunctional or aromatic residue preferred, L or F most preferred);

X8 is an amino acid residue (nonfunctional residue preferred, M or Nle most preferred);

$X^{10}$ is an amino acid residue (an acidic or hydrophilic residue preferred, N or D most preferred);

$X^{11}$ is an amino acid residue (nonfunctional or basic residue preferred, L, R, or K most preferred);

$X^{12}$ is an amino acid residue (nonfunctional or aromatic residue preferred, G, F, or W most preferred);

$X^{14}$ is an amino acid residue (basic or hydrophilic residue preferred, H or S most preferred);

$X^{15}$ is an amino acid residue (nonfunctional residue preferred, with L or I most preferred);

$X^{16}$ is an amino acid residue (nonfunctional or hydrophilic residue preferred, Q, N, S, or A most preferred);

$X^{17}$ is an amino acid residue (acidic, hydrophilic, or nonfunctional residue preferred; S, D, or L most preferred);

$X^{18}$ is an amino acid residue (nonfunctional residue preferred, M, L, V or Nle most preferred);

$X^{19}$ is an amino acid residue (acidic or basic residue preferred, E or R most preferred);

$X^{21}$ is an amino acid residue (nonfunctional residue or basic residue preferred; V, M, R, or Nle most preferred);

$X^{22}$ is an amino acid residue (hydrophilic, acidic, or aromatic residue preferred, E or F most preferred);

$X^{23}$ is an aromatic or lipophilic residue (W or F preferred);

$X^{24}$ is a lipophilic residue (L preferred);

$X^{25}$ is an amino acid residue (hydrophilic or basic residue preferred, R or H most preferred);

$X^{26}$ is an amino acid residue (hydrophilic or basic residue preferred, K or H most preferred);

$X^{27}$ is an amino acid residue (lipophilic, basic, or nonfunctional residue preferred, K or L most preferred);

$X^{28}$ is an amino acid residue (lipophilic or nonfunctional residue preferred, L or I most preferred);

$X^C$ is absent or is $X^{29}$, $X^{29}X^{30}$, $X^{29}X^{30}X^{31}$, $X^{29}X^{30}X^{31}X^{32}$, $X^{29}X^{30}X^{31}X^{32}X^{33}$, $X^{29}X^{30}X^{31}X^{32}X^{33}X^{34}$, $X^{29}X^{30}X^{31}X^{32}X^{33}X^{34}X^{35}$, or $X^{29}X^{30}X^{31}X^{32}X^{33}X^{34}X^{35}X^{36}$;

$X^{29}$ is an amino acid residue (hydrophilic or nonfunctional residue preferred, Q or A most preferred);

$X^{30}$ is an amino acid residue (hydrophilic or acidic residue preferred, D or E most preferred);

$X^{31}$ is an amino acid residue (lipophilic or nonfunctional residue preferred, V or I most preferred);

$X^{32}$ is an amino acid residue (basic residue preferred, H most preferred);

$X^{33}$ is an amino acid residue (hydrophilic residue preferred, N or T most preferred);

$X^{34}$ is an amino acid residue (nonfunctional or aromatic residue preferred, A, F or Y most preferred);

$X^{35}$ is an amino acid residue (acidic residue preferred, E most preferred); and $X^{36}$ is an amino acid residue (aromatic residue preferred, Y most preferred).

A preferred PTH/PTHrP modulating domain sequence formula is

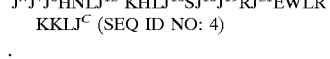
$KKLJ^C$ (SEQ ID NO: 4)    III wherein:

$J^N$ is absent or is selected from $J^1J^2J^3J^4J^5J^6$, $J^2J^3J^4J^5J^6$, $J^3J^4J^5J^6$;

$J^1$ is an amino acid residue (nonfunctional, hydrophilic, or aromatic residue preferred; A, S or Y most preferred);

$J^2$ is an amino acid residue (nonfunctional residue preferred, V most preferred);

$J^3$ is an amino acid residue (hydrophilic residue preferred, S most preferred);

$J^4$ is an amino acid residue (acidic residue preferred, E most preferred);

$J^5$ is an amino acid residue (nonfunctional residue preferred, I most preferred);

$J^6$ is an amino acid residue (basic residue preferred, Q preferred);

$J^7$ is an amino acid residue (nonfunctional or aromatic residue preferred, L or F most preferred);

$J^8$ is an amino acid residue (nonfunctional residue preferred, M or Nle most preferred);

$J^{12}$ is an amino acid residue (nonfunctional or aromatic residue preferred, G or W most preferred);

$J^{16}$ is an amino acid residue (nonfunctional or hydrophilic residue preferred, N, S, or A most preferred);

$J^{18}$ is an amino acid residue (nonfunctional residue preferred, M, Nle, L, or V most preferred);

$J^{19}$ is an acidic or basic residue (E or R preferred);

$J^{21}$ is an amino acid residue (nonfunctional residue preferred, V, M, or Nle most preferred);

$J^C$ is absent or is $J^{29}$, $J^{29}J^{30}$, $J^{29}J^{30}J^{31}$, $J^{29}J^{30}J^{31}J^{32}$, $J^{29}J^{30}J^{31}J^{32}J^{33}$, or $J^{29}J^{30}J^{31}J^{32}J^{33}J^{34}$;

$J^{29}$ is an amino acid residue (hydrophilic or nonfunctional residue preferred, Q or A most preferred);

$J^{30}$ is an amino acid residue (hydrophilic or acidic residue preferred, D or E most preferred);

$J^{31}$ is an amino acid residue (lipophilic or nonfunctional residue preferred, V or I most preferred);

$J^{32}$ is an amino acid residue (basic residue preferred, H most preferred);

$J^{33}$ is an amino acid residue (acidic residue preferred, N most preferred);

$J^{34}$ is an amino acid residue (aromatic residue preferred, F or Y most preferred).

From the formula of SEQ ID NO: 4, peptides appearing in Table 1 below are most preferred.

Another preferred PTH/PTHrP modulating domain sequence is $O^{N}LHO^{10}O^{11}O^{12}KSIO^{15}O^{16}LRRRFO^{23}LHHLIO^{C}$ (SEQ ID NO: 5)   IV wherein:

$O^{N}$ is absent or is $YO^1O^2O^3O^4O^5O^6O^7$, $O^1O^2O^3O^4O^5O^6O^7$, $O^2O^3O^4O^5O^6O^6O^7$, $O^3O^4O^5O^6O^7$, $O^4O^5O^6O^7$, $O^5O^6O^7$, $O^6O^7$, or $O^7$;

$O^1$ is an amino acid residue (nonfunctional residue preferred, A most preferred);

$O^2$ is an amino acid residue (nonfunctional residue preferred, V most preferred);

$O^3$ is an amino acid residue (hydrophilic residue preferred, S most preferred);

$O^4$ is an amino acid residue (acidic residue preferred, E most preferred);

$O^5$ is an amino acid residue (basic or nonfunctional residue preferred, H or I preferred);

$O^6$ is an amino acid residue (hydrophilic residue preferred, Q most preferred);

$O^7$ is an amino acid residue (nonfunctional residue preferred, L most preferred);

$O^{10}$ is an amino acid residue (acidic or hydrophilic residue preferred, N or D most preferred);

$O^{11}$ is an amino acid residue (basic or nonfunctional residue preferred, K or L most preferred);

$O^{12}$ is an amino acid residue (aromatic or nonfunctional residue preferred, G, F, or W most preferred);

$O^{15}$ is an amino acid residue (hydrophilic or nonfunctional residue preferred, I or S most preferred);

$O^{16}$ is an amino acid residue (hydrophilic residue preferred, Q or N most preferred);

$O^{17}$ is an amino acid residue (acidic or nonfunctional residue preferred, D or L most preferred);

$O^{23}$ is an amino acid residue (aromatic residue preferred, with F or W most preferred);

$O^{C}$ is absent or is $O^{29}$, $O^{29}O^{30}$, $O^{29}O^{30}O^{31}$, $O^{29}O^{30}O^{31}O^{32}$, $O^{29}O^{30}O^{31}O^{32}O^{33}$, $O^{29}O^{30}O^{31}O^{32}O^{33}O^{34}$, $O^{29}O^{30}O^{31}O^{32}O^{33}O^{34}O^{35}$, or $O^{29}O^{30}O^{31}O^{32}O^{33}O^{34}O^{35}O^{36}$; and $O^{29}$ through $O^{36}$ are each independently amino acid residues.

From the formula of SEQ ID NO: 5, peptides appearing in Table 2 below are most preferred.

Exemplary peptide sequences for this invention appear in Tables 1 and 2 below. These peptides may be prepared as described in the cited references or in U.S. Pat. Nos. 4,423,037, 4,968,669, 5,001,22, and 6,051,686, each of which is hereby incorporated by reference in its entirety. Molecules of this invention incorporating these peptide sequences may be prepared by methods known in the art. Single letter amino acid abbreviations are used. Any of these peptides may be linked in tandem (i.e., sequentially), with or without linkers. Any peptide containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized as described hereinafter.

TABLE 1

PTH/PTHrP modulating domains based on PTH

| Description | Sequence | SEQ ID NO: |
|---|---|---|
| human PTH(1–84)[1] | SVSEIQLMHNLGKHLNSMERVEWLRKKLQDVHNFV ALGAPLAPRDAGSQRPRKKEDNVLVESHEKSLGEA DKADVNVLTKAKSQ | 10 |
| rat PTH(1–84)[2] | AVSEIQLMHNLGKHLASVERMQWLRKKLQDVHNFV SLGVQMAAREGSYQRPTKKEDNVLVDGNSKSLGEG DKADVDVLVKAKSQ | 11 |
| human PTH[3](7–84) | LMHNLGKHLNSMERVEWLRKKLQDVHNFVALGAPL APRDAGSQRPRKKEDNVLVESHEKSLGEADKADVN VLTKAKSQ | 12 |
| human PTH(1–44)[3] | SVSEIQLMHNLGKHLNSMERVEWLRKKLQDVHNFV ALGAPLAPR | 13 |
| human PTH(1–38)[3] | SVSEIQLMHNLGKHLNSMERVEWLRKKLQDVHNFV ALG | 14 |
| human PTH(2–38)[3] | VSEIQLMHNLGKHLNSMERVEWLRKKLQDVHNFVA LG | 15 |

TABLE 1-continued

PTH/PTHrP modulating domains based on PTH

| Description | Sequence | SEQ ID NO: |
|---|---|---|
| human PTH(1–34)[4] | SVSEIQLMHNLGKHLNSMERVEWLRKKLQDVHNF | 16 |
| [Arg11]human PTH(1–34) | SVSEIQLMHNRGKHLNSMERVEWLRKKLQDVHNF | 17 |
| [Lys11] human PTH(1–34) | SVSEIQLMHNKGKHLNSMERVEWLRKKLQDVHNF | 18 |
| [Arg19] human PTH(1–34) | SVSEIQLNHNLGKHLNSMRRVEWLRKKLQDVHNF | 19 |
| [Tyr1] human PTH(1–34)[3] | YVSEIQLMHNLGKHLNSMERVEWLRKKLQDVHNF | 20 |
| [Leu(8, 18), Tyr34] human PTH(1–34)[3] | SVSEIQLLHNLGKHLNSLERVEWLRKKLQDVHNY | 21 |
| bovine PTH(1–34)[5] | AVSEIQFMHNLGKHLSSMERVEWLRKKLQDVHNF | 22 |
| [Leu(8, 18), Tyr34] bovine PTH (1–34)[6] | AVSEIQFLHNLGKHLSSLERVEWLRKKLQDVHNY | 23 |
| porcine PTH(1–34)[3] | SVSEIQLMHNLGKHLSSLERVEWLRKKLQDVHNF | 24 |
| rat PTH(1–34)[3] | AVSEIQLMHNLGKHLASVERMQWLRKKLQDVHNF | 25 |
| [Leu (8, 21), Tyr34] rat PTH (1–34)[3] | AVSEIQLLHNLGKHLASVERLQWLRKKLQDVHNY | 26 |
| human PTH(1–31)[7] | SVSEIQLMHNLGKHLNSMERVEWLRKKLQDV | 27 |
| [Leu27] human PTH(1–31)[8] | SVSEIQLMHNLGKHLNSMERVEWLRKLLQDV | 28 |
| [Leu(8, 18) Tyr34] PTH(3–34)[9] | SEIQLLHNLGKHLNSLERVEWLRKKLQDVHNY | 29 |
| bovine PTH(3–34)[10] | SEIQFMHNLGKHLSSMERVEWLRKKLQDVHNF | 30 |
| [Leu(8, 18), Tyr34] bovine PTH(3–34)[11] | SEIQFLHNLGKHLSSLERVEWLRKKLQDVHNY | 31 |
| human PTH(7–34)[12] | LMHNLGKHLNSMERVEWLRKKLQDVHNF | 32 |
| [Leu(8, 18) Tyr34] human PTH(7–34)[9] | LLHNLGKHLNSLERVEWLRKKLQDVHNY | 33 |
| bovine PTH 7–34[13] | FMHNLGKHLSSMERVEWLRKKLQDVHNF | 34 |
| [Tyr34] bovine PTH(7–34)[14] | FMHNLGKHLSSMERVEWLRKKLQDVHNY | 35 |
| [Leu(8, 18), Tyr34] bovine PTH(7–34)[15] | FLHNLGKHLSSLERVEWLRKKLQDVHNY | 36 |
| [Leu(8, 18), Trp12, Tyr34] bovine PTH(7–34)[16] | FLHNLWKHLSSLERVEWLRKKLQDVHNY | 37 |
| [D-Trp12, Tyr34] bovine PTH(7–34)[17] | FMHNL-D-Trp-KHLSSMERVEWLRKKLQDVHNY | 38 |
| human PTH(1–30) | SVSEIQLMHNLGKHLNSMERVEWLRKKLQD | 39 |
| [Arg11] human PTH(1–30) | SVSEIQLMHNRGKHLNSMERVEWLRKKLQD | 40 |
| [Lys11] human PTH(1–30) | SVSEIQLMHNKGKHLNSMERVEWLRKKLQD | 41 |
| [Arg19]human PTH(1–30) | SVSEIQLMHNLGKHLNSMRRVEWLRKKLQD | 42 |
| [Tyr1] human PTH(1–30) | YVSEIQLMHNLGKHLNSMERVEWLRKKLQD | 43 |
| [Leu(8, 18)] human PTH(1–30) | SVSEIQLLHNLGKHLNSLERVEWLRKKLQD | 44 |
| bovine PTH(1–30) | AVSEIQFMHNLGKHLSSMERVEWLRKKLQD | 45 |
| [Leu(8, 18)] bovine PTH(1–30) | AVSEIQFLHNLGKHLSSLERVEWLRKKLQD | 46 |
| porcine PTH(1–30) | SVSEIQLMHNLGKHLSSLERVEWLRKKLQD | 47 |

TABLE 1-continued

PTH/PTHrP modulating domains based on PTH

| Description | Sequence | SEQ ID NO: |
|---|---|---|
| rat PTH(1–30) | AVSEIQLMHNLGKHLASVERMQWLRKKLQD | 48 |
| [Leu(8, 21), Tyr34] rat PTH(1–30) | AVSEIQLLHNLGKHLASVERLQWLRKKLQD | 49 |
| [Leu27] human PTH(1–30) | SVSEIQLMHNLGKHLNSMERVEWLRKLLQD | 50 |
| human PTH(1–29) | SVSEIQLMHNLGKHLNSMERVEWLRKKLQ | 51 |
| human PTH(1–28) | SVSEIQLMHNLGKHLNSMERVEWLRKKL | 52 |
| [Leu(8, 18)] PTH(3–30) | SEIQLLHNLGKHLNSLERVEWLRKKLQD | 53 |
| bovine PTH(3–30) | SEIQFMHNLGKHLSSMERVEWLRKKLQD | 54 |
| [Leu(8, 18)] bovine PTH(3–30) | SEIQFLHNLGKHLSSLERVEWLRKKLQD | 55 |
| human PTH(7–30) | LMHNLGKHLNSMERVEWLRKKLQD | 56 |
| [Leu(8, 18)] human PTH(7–30) | LLHNLGKHLNSLERVEWLRKKLQD | 57 |
| bovine PTH(7–30) | FMHNLGKHLSSMERVEWLRKKLQD | 58 |
| [Leu(8, 18)] bovine PTH(7–30) | FLHNLGKHLSSLERVEWLRKKLQD | 59 |
| [Leu(8, 18), Trp12] bovine PTH(7–30) | FLHNLWKHLSSLERVEWLRKKLQD | 60 |
| [D-Trp12] bovine PTH(7–30) | FMHNL-D-Trp-KHLSSMERVEWLRKKLQD | 61 |

[1]Hendy et al. (1981), Proc. Natl. Acad. Sci USA 78: 7365; Kimura et al. (1983), Biochem. Biophys. Res. Commun. 114: 493; Zanelli et al. (1985), Endocrinology 117: 1962; Wingender et al. (1985), J. Biol. Chem. 264: 4367.
[2]Heinrich et al. (1984), J. Biol. Chem. 259: 3320.
[3]Bachem Catalogue (1999).
[4]Doppelt et al. (1981), Calcif. Tissue Int. 33: 649; Podbesek et al. (1983) Endocrinology 112: 1000; Kent et al. (1985), Clin. Sci. 68: 171; McKee and Caulfield (1989), Peptide Res. 2: 161; Lee and Russell (1989); Biopolymers 28: 1115; Reeve et al. (1990), Br. Med. J. 301: 314; Neugebauer et al. (1994), Int. J. Peptide Protein Res. 43: 555.
[5]Nakamura et al. (1981); Proc. Soc. Exp. Biol. Med. 168: 168; Law et al. (1983), J. Clin. Endocrinol. Metab. 56: 1335; Wang et al. (1984), Eur. J. Pharmacol. 97, 209; Sham et al. (1986), Gen. Comp. Endocrinol. 61: 148; Smith et al. (1987), Arch. Biochem. Biophys. 253: 81.
[6]Based on Coltrera et al. (1981), J. Biol. Chem. 256: 10555; Bergeron et al. (1981), Endocrinology 109: 1552.
[7]Jouishomme et al. (1994), J. Bone Miner. Res. 9: 943; Whitfield and Morley; TIPS 16: 382.
[8]Barbier et al. (1997), J. Med. Chem. 40: 1373.
[9]Based on Schipani et al. (1993), Endocrinology 132: 2157–65.
[10]Scharla et al. (1991), Horm. Metab. Res. 23: 66–9; McGowan et al. (1983), Science 219: 67; Lowik et al. (1985), Cell Calcium 6: 311.
[11]Based on Jobert et al. (1997), Endocrinology 138: 5282; Schipani et al. (1993); Rosenblatt et al. (1977), J. Biol. Chem. 252: 5847; Segre et al. (1979), J. Biol. Chem. 254: 6980; Nussbaum et al. (1980), J. Biol. Chem. 225: 10183; Gray et al. (1980), Br. J. Pharmacol. 76: 259.
[12]Nissenson et al. (1999), Endocrinology 140: 1294–1300.
[13]Jueppner et al. (1996), Endocrinology.
[14]Horiuchi et al. (1983), Science 220: 1053.
[15]Schipani et al. (1993); Holick et al. (1995), Bone 16: 140S (abstract 223, Conference, Melbourne, February 1995).
[16]Based on Dresner-Pollak et al. (1996), JBMR 11: 1061–5.
[17]Goldman et al. (1988), Endocrinology 123: 2597.

TABLE 2

PTH/PTHrP Modulating Domains Based on PTHrP

| Description | Sequence | SEQ ID NO: |
| --- | --- | --- |
| human PTHrP(1-86)[3] | AVSEHQLLHDKGKSIQDLRRRFFLHHLIAEIHTAE IRATSEVSPNSKPSPNTKNHPVRFGSDDEGRYLTQ ETNKVETYKEQPLKTP | 62 |
| human PTHrP(1-34)[18] | AVSEHQLLHDKGKSIQDLRRRFFLHHLIAETHTA | 63 |
| [Tyr36] human PTHrP(1-36)[3] | AVSEHQLLHDKGKSIQDLRRRFFLHHLIAEIHTAE Y | 64 |
| [Ile5, Trp23, Tyr36] human PTHrP(1-36)[3] | AVSEIQLLHDKGKSIQDLRRRFWLHHLIAEIHTAE Y | 65 |
| Tyr-human PTHrP(1-34)[3] | YAVSEHQLLHDKGKSIQDLRRRFFLHHLIAEIHTA | 66 |
| [Asn10, Leu11, D-Phe12] human PTHrP(1-34)[19] | AVSEHQLLHNL-D-Phe-KSIQDLRRRFFLHHLIAEIHTA | 67 |
| PTHrP(7-34)[20] | LLHDKGKSIQDLRRRFFLHHLIAEIHTA | 68 |
| [Asn10, Leu11] human PTHrP(7-34) | LLHNLGKSIQDLRRRFFLHHLIAEIHTA | 69 |
| [Asn16, Leu17] PTHrP(7-34)[21] | LLHDKGKSINLLRRRFFLHHLIAEIHTA | 70 |
| [Leu11, D-Trp12] human PTHrP(7-34)[22] | LLHDL-D-Trp-KSIQDLRRRFFLHHLIAEIHTA | 71 |
| [Asn10, Leu11, D-Trp12] PTHrP(7-34)[23] | LLHNL-D-Trp-KSIQDLRRRFFLHHLIAEIHTA | 72 |
| [D-Trp12] PTHrP(8-34) | LHNL-D-Trp-KSIQDLRRRFFLHHLIAEIHTA | 73 |
| [D-Phe12] PTHrP(8-34) | LHNL-D-Phe-KSIQDLRRRFFLHHLIAEIHTA | 74 |
| [Asn10, Leu11, D-Trp12] human PTHrP(7-34)[20] | LLHNL-D-Trp-KSIQDLRRRFFLHHLIAEIHTA | 75 |
| human PTHrP(1-30) | AVSEHQLLHDKGKSIQDLRRRFFLHHLIAE | 76 |
| [Ile5, Trp23] human PTHrP(1-30) | AVSEIQLLHDKGKSIQDLRRRFWLHHLIAE | 77 |
| Tyr-human PTHrP(1-30) | YAVSEHQLLHDKGKSIQDLRRRFFLHHLIAE | 78 |
| [Asn10, Leu11, D-Phe12] human PTHrP(1-30) | AVSEHQLLHNL-D-Phe-KSIQDLRRRFFLHHLIAE | 79 |
| PTHrP(7-30) | LLHDKGKSIQDLRRRFFLHHLIAE | 80 |
| [Asn10, Leu11] human PTHrP(7-30) | LLHNLGKSIQDLRRRFFLHHLIAE | 81 |
| [Asn16, Leu17] PTHrP(7-30) | LLHDKGKSINLLRRRFFLHHLIAE | 82 |
| [Leu11, D-Trp12] human PTHrP(7-30) | LLHDL-D-Trp-KSIQDLRRRFFLHHLIAE | 83 |
| [Asn10, Leu11, D-Trp12] PTHrP(7-30) | LLHNL-D-Trp-KSIQDLRRRFFLHHLIAE | 84 |
| [D-Trp12] PTHrP(8-30) | LHNL-D-Trp-KSIQDLRRRFFLHHLIAE | 85 |
| [D-Phe12] PTHrP(8-30) | LHNL-D-Phe-KSIQDLRRRFFLHHLIAE | 86 |
| [Asn10, Leu11, D-Trp12] human PTHrP(7-30) | LLHNL-D-Trp-KSIQDLRRRFFLHHLIAE | 87 |
| [Haa(Laa Laa Haa Haa)2 Laa 22-31] human PTH(1-34)[24] | SVSEIQLMHNLGKHLNSMERVELLEKLLEKKLHNF | 88 |
| [Haa(Laa Laa Haa Haa)2 Laa 22-31] human PTH(1-34)[24] | SVSEIQLMHNLGKHLNSMERVELLEKLLKKLHNF | 89 |
| [Haa(Laa Laa Haa Haa)2 Laa 22-31] human PTH(1-34)[25] | SVSEIQLMHNLGKHLNSMERVALAEALAEALHNF | 90 |

TABLE 2-continued

PTH/PTHrP Modulating Domains Based on PTHrP

| Description | Sequence | SEQ ID NO: |
|---|---|---|
| [Haa(Laa Laa Haa Haa)2 Laa 22–31] human PTH(1–34)[26] | SVSEIQLMHNLGKHLNSMERVSLLSSLLSSLHNF | 91 |
| [Haa(Laa Laa Haa Haa)2 Laa 22–31] human PTH(1–34)[27] | SVSEIQLMHNLGKHLNSMERVAFYDKVAEKLHNF | 92 |
| [Haa(Laa Laa Haa Haa)$_2$ Laa 22–31] human PTH(7–34)[24] | LMHNLGKHLNSMERVELLEKLLEKLHNF | 93 |
| [Haa(Laa Laa Haa Haa)$_2$ Laa 22–31] human PTH(7–34)[24] | LMHNLGKHLNSMERVELLEKLLKKLHNF | 94 |
| [Haa(Laa Laa Haa Haa)2 Laa 22–31] human PTH(7–34)[25] | LMHNLGKHLNSMERVALAEALAEALHNF | 95 |
| [Haa(Laa Laa Haa Haa)2 Laa 22–31] human PTH(7–34)[26] | LMHNLGKHLNSMERVSLLSSLLSSLHNF | 96 |
| [Haa(Laa Laa Haa Haa)2 Laa 22–31] human PTH(7–34)[27] | LMHNLGKHLNSMERVAFYDKVAEKLHNF | 97 |
| [Haa(Laa Laa Haa Haa)2 Laa 22–31] human PTHrP(1–34)[24] | AVSEHQLLHDKGKSIQDLRRRELLEKLLEKLHTA | 98 |
| [Haa(Laa Laa Haa Haa)2 Laa 22–31] human PTHrP(1–34)[24] | AVSEHQLLHDKGKSIQDLRRRELLEKLLKKLHTA | 99 |
| [Haa(Laa Laa Haa Haa)2 Laa 22–31] human PTHrP(1–34)[25] | AVSEHQLLHDKGKSIQDLRRRALAEALAEALHTA | 100 |
| [Haa(Laa Laa Haa Haa)2 Laa 22–31] human PTHrP(1–34)[26] | AVSEHQLLHDKGKSIQDLRRRSLLSSLLSSLHTA | 101 |
| [Haa(Laa Laa Haa Haa)2 Laa 22–31] human PTHrP(1–34)[27] | AVSEHQLLHDKGKSIQDLRRRAFYDKVAEKLHTA | 102 |
| [Haa(Laa Laa Haa Haa)2 Laa 22–31] human PTHrP(7–34)[28] | LLHDKGKSIQDLRRRELLEKLLEKLHTA | 103 |
| [Haa(Laa Laa Haa Haa)2 Laa 22–31] human PTHrP(7–34)[24] | LLHDKGKSIQDLRRRELLEKLLKKLHTA | 104 |
| [Haa(Laa Laa Haa Haa)2 Laa 22–31] human PTHrP(7–34)[25] | LLHDKGKSIQDLRRRALAEALAEALHTA | 105 |
| [Haa(Laa Laa Haa Haa)2 Laa 22–31] human PTHrP(7–34)[26] | LLHDKGKSIQDLRRRSLLSSLLSSLHTA | 106 |
| [Haa(Laa Laa Haa Haa)2 Laa 22–31] human PTHrP(7–34)[27] | LLHDKGKSIQDLRRRAFYDKVAEKLHTA | 107 |
| [Lys11, Lys13; Arg19, Arg21; Haa(Laa Laa Haa Haa)2 Laa 22–31] human PTHrP(1–34)[29] | AVSEHQLLHDKGKSIQDLRRRELLEKLLRKLHTA | 108 |
| [Lys11, Lys13; Arg19, Arg21; Haa(Laa Laa Haa Haa)2 Laa 22–31] human PTHrP(1–34)[30] | AVSEHQLLHDKGKSIQDLRRRELLEKLLEKLHTS | 109 |
| [Lys11, Lys13; Arg19, Arg21; Haa(Laa Laa Haa Haa)2 Laa 22–31] human PTHrP(1–34)[31] | AVSEHQLLHDKGKSIQDLRRRELLEKLLEKLHTAGRR | 110 |
| [Lys11, Lys13; Arg19, Arg21; Haa(Laa Laa Haa Haa)2 Laa 22–31] human PTHrP(1–34)[32] | AVSEHQLLHDKGKSIQDLRRRELLEKLLEKLKEL | 111 |
| [Lys11, Lys13, Ala19, Arg21, Haa(Laa Laa Haa Haa)$_2$ Laa 22–31] human PTHrP(1–34)[33] | AVSEHQLLHDKGKSIQDLARRELLEKLLEKLHTA | 112 |
| [Lys11, Lys13, Arg19, Ala21, Haa(Laa Laa Haa Haa)$_2$ Laa 22–31] human PTHrP(1–34)[34] | AVSEHQLLHDKGKSIQDLRRAELLEKLLEKLHTA | 113 |

TABLE 2-continued

PTH/PTHrP Modulating Domains Based on PTHrP

| Description | Sequence | SEQ ID NO: |
|---|---|---|
| [Leu11, Lys13, Arg19, Arg21, Haa(Laa Laa Haa Haa)$_2$ Laa 22-31] human PTHrP(1-34)[35] | AVSEAQLLHDLGKSIQDLRRRELLEKLLEKLHAL | 114 |
| [Lys11, Lys13, Arg19, Arg21, Haa(Laa Laa Haa Haa)$_2$ Laa 22-31] human PTHrP(1-34)[36] | AVSEHQLLHDKGKSIQDLRRRELLERLLERLHTA | 115 |
| [Arg11, Arg13, Arg19, Arg21, Haa(Laa Laa Haa Haa)$_2$ Laa 22-31] human PTHrP(1-34)[37] | AVSEHQLLHDRGRSIQDRRRELLERLLERLHTA | 116 |
| [Arg11, Lys13, Arg19, Arg21, Haa(Laa Laa Haa Haa)$_2$ Laa 22-31] human PTHrP(1-34)[38] | AVSEHQLLHDRGKSIQDLRRRELLERLLKRLHTA | 117 |
| [Arg11, Arg13, Arg19, Arg21, Haa(Laa Laa Haa Haa)$_2$ Laa 22-31] human PTHrP(1-34)[39] | AVSEHQLLHDRGRSIQDLRRRELLERLLKRLHTA | 118 |
| Haa(Laa Laa Haa Haa)$_2$ Laa 22-31] human PTHrP(1-34)[40] | AVSEHQLLHDKGKSIQDLRRRALAEALAEALHTA | 119 |
| Haa(Laa Laa Haa Haa)$_2$ Laa 22-31] human PTHrP(1-34)[41] | AVSEHQLLHDKGKSIQDLRRRSLLSSLLSSLHTA | 120 |
| Haa(Laa Laa Haa Haa)$_2$ Laa 22-31] human PTHrP(1-34)[42] | AVSEHQLLHDKGKSIQDLRRRAFYDKVAEKLHTA | 121 |
| Haa(Laa Laa Haa Haa)$_2$ Laa 22-31] human PTHrP(1-34)[43] | AVSEIQFMHNLGKHLSSMERVELLEKLLEKLHNY | 122 |
| Haa(Laa Laa Haa Haa)$_2$ Laa 22-31] human PTHrP(1-34)[44] | AVSEIQFMHNLGKHLSSMRRRELLEKLLEKLHNY | 123 |
| [Haa(Laa Laa Haa Haa)$_2$ Laa 22-30] human PTH(1-30) | SVSEIQLMHNLGKHLNSMERVELLEKLLEK | 124 |
| [Haa(Laa Laa Haa Haa)$_2$ Laa 22-30] human PTH(1-30) | SVSEIQLMHNLGKHLNSMERVELLEKLLKK | 125 |
| [Haa(Laa Laa Haa Haa)$_2$ Laa 22-30] human PTH(1-30) | SVSEIQLMHNLGKHLNSMERVALAEALAEA | 126 |
| [Haa(Laa Laa Haa Haa)$_2$ Laa 22-30] human PTH(1-30) | SVSEIQLMHNLGKHLNSMERVSLLSSLLSS | 127 |
| [Haa(Laa Laa Haa Haa)$_2$ Laa 22-30] human PTH(1-34)[27] | SVSEIQLMHNLGKHLNSMERVAFYDKVAEKLHNF | 128 |
| [Haa(Laa Laa Haa Haa)$_2$ Laa 22-30] human PTH(7-30) | LMHNLGKHLNSMERVELLEKLLEK | 129 |
| [Haa(Laa Laa Haa Haa)$_2$ Laa 22-30] human PTH(7-30) | LMHNLGKHLNSMERVELLEKLLKK | 130 |
| [Haa(Laa Laa Haa Haa)$_2$ Laa 22-30] human PTH(7-30) | LMHNLGKHLNSMERVALAEALAEA | 131 |
| [Haa(Laa Laa Haa Haa)$_2$ Laa 22-30] human PTH(7-30) | LMHNLGKHLNSMERVSLLSSLLSS | 132 |
| [Haa(Laa Laa Haa Haa)$_2$ Laa 22-30] human PTH(7-30) | LMHNLGKHLNSMERVAFYDKVAEK | 133 |
| [Haa(Laa Laa Haa Haa)$_2$ Laa 22-30] human PTHrP(1-30) | AVSEHQLLHDKGKSIQDLRRRELLEKLLEK | 134 |
| [Haa(Laa Laa Haa Haa)$_2$ Laa 22-30] human PTHrP(1-30) | AVSEHQLLHDKGKSIQDLRRRELLEKLLKK | 135 |
| [Haa(Laa Laa Haa Haa)$_2$ Laa 22-30] human PTHrP(1-30) | AVSEHQLLHDKGKSIQDLRRRALAEALAEA | 136 |

TABLE 2-continued

PTH/PTHrP Modulating Domains Based on PTHrP

| Description | Sequence | SEQ ID NO: |
|---|---|---|
| [Haa(Laa Laa Haa Haa)$_2$ Laa 22–30] human PTHrP(1–30) | AVSEHQLLHDKGKSIQDLRRRSLLSSLLSS | 137 |
| [Haa(Laa Laa Haa Haa)$_2$ Laa 22–30] human PTHrP(1–30) | AVSEHQLLHDKGKSIQDLRRRAFYDKVAEK | 138 |
| [Haa(Laa Laa Haa Haa)$_2$ Laa 22–30] human PTHrP(7–30) | LLHDKGKSIQDLRRRELLEKLLEK | 139 |
| [Haa(Laa Laa Haa Haa)$_2$ Laa 22–30] human PTHrP(7–30) | LLHDKGKSIQDLRRRELLEKLLKK | 140 |
| [Haa(Laa Laa Haa Haa)$_2$ Laa 22–30] human PTHrP(7–30) | LLHDKGKSIQDLRRRALAEALAEA | 141 |
| [Haa(Laa Laa Haa Haa)$_2$ Laa 22–30] human PTHrP(7–30) | LLHDKGKSIQDLRRRSLLSSLLSS | 142 |
| [Haa(Laa Laa Haa Haa)$_2$ Laa 22–30] human PTHrP(7–30) | LLHDKGKSIQDLRRRAFYDKVAEK | 143 |
| [Lys11, Lys13; Arg19, Arg21; Haa(Laa Laa Haa Haa)$_2$ Laa 22–30] human PTHrP(1–30) | AVSEHQLLHDKGKSIQDLRRRELLEKLLRK | 144 |
| [Lys11, Lys13; Arg19, Arg21; Haa(Laa Laa Haa Haa)$_2$ Laa 22–30] human PTHrP(1–30) | AVSEHQLLHDKGKSIQDLRRRELLEKLLEK | 145 |
| [Lys11, Lys13; Arg19, Arg21; Haa(Laa Laa Haa Haa)$_2$ Laa 22–30] human PTHrP(1–30) | AVSEHQLLHDKGKSIQDLRRRELLEKLLEKLHT | 146 |
| [Lys11, Lys13; Arg19, Arg21; Haa(Laa Laa Haa Haa)$_2$ Laa 22–30] human PTHrP(1–30) | AVSEHQLLHDKGKSIQDLRRRELLEKLLEK | 147 |
| [Lys11, Lys13, Ala19, Arg21, Haa(Laa Laa Haa Haa)$_2$ Laa 22–30] human PTHrP(1–30) | AVSEHQLLHDKGKSIQDLARRELLEKLLEK | 148 |
| [Lys11, Lys13, Arg19, Ala21, Haa(Laa Laa Haa Haa)$_2$ Laa 22–30] human PTHrP(1–30) | AVSEHQLLHDKGKSIQDLRRAELLEKLLEK | 149 |
| [Leu11, Lys13, Arg19, Arg21, Haa(Laa Laa Haa Haa)$_2$ Laa 22–30] human PTHrP(1–30) | AVSEAQLLHDLGKSIQDLRRRELLEKLLEK | 150 |
| [Lys11, Lys13, Arg19, Arg21, Haa(Laa Laa Haa Haa)$_2$ Laa 22–30] human PTHrP(1–30) | AVSEHQLLHDKGKSIQDLRRRELLERLLER | 151 |
| [Arg11, Arg13, Arg19, Arg21, Haa(Laa Laa Haa Haa)$_2$ Laa 22–30] human PTHrP(1–30) | AVSEHQLLHDRGRSIQDRRRELLERLLER | 152 |
| [Arg11, Lys13, Arg19, Arg21, Haa(Laa Laa Haa Haa)$_2$ Laa 22–30] human PTHrP(1–30) | AVSEHQLLHDRGKSIQDLRRRELLERLLKR | 153 |
| [Arg11, Arg13, Arg19, Arg21, Haa(Laa Laa Haa Haa)$_2$ Laa 22–30] human PTHrP(1–30) | AVSEHQLLHDRGRSIQDLRRRELLERLLKR | 154 |
| Haa(Laa Laa Haa Haa)$_2$ Laa 22–30] human PTHrP(1–30) | AVSEHQLLHDKGKSIQDLRRRALAEALAEA | 155 |
| Haa(Laa Laa Haa Haa)$_2$ Laa 22–30] human PTHrP(1–30) | AVSEHQLLHDKGKSIQDLRRRSLLSSLLSS | 156 |
| Haa(Laa Laa Haa Haa)$_2$ Laa 22–30] human PTHrP(1–30) | AVSEHQLLHDKGKSIQDLRRRAFYDKVAEK | 157 |

TABLE 2-continued

PTH/PTHrP Modulating Domains Based on PTHrP

| Description | Sequence | SEQ ID NO: |
|---|---|---|
| Haa(Laa Laa Haa Haa)$_2$ Laa 22–30] human PTHrP(1–30) | AVSEIQFMHNLGKHLSSMERVELLEKLLEK | 158 |
| Haa(Laa Laa Haa Haa)$_2$ Laa 22–30] human PTHrP(1–30) | AVSEIQFMHNLGKHLSSMRRRELLEKLLEK | 159 |

[18] Moseley et al. (1987), Proc. Natl. Acad. Sci. USA 84: 5048; Suva et al. (1987), Science 237: 893; Kemp et al. (1987), Science 238: 1568; Paspaliaris et al. (1995), Bone 16: 141S (abstract 225, Conference, Melbourne 1995).
[19] Based on JP 07316195, May 25, 1994 (Nippon Kayaku).
[20] Nagasaki et al. (1989), Biochem. Biophys. Res. Commun. 158: 1036; Nutt et al.; Endocrinology 127, 491 (1990).
[21] Williams et al. (1998), J. Reproduction & Fertility 112: 59–67.
[22] Gardella et al. (1996), Endocrinol. 137: 3936–41; Fukayama et al. (1998), Am. J-. Physiol. 274: E297–E303.
[23] Li et al. (1996), Endocrinology.
[24] Incorporating SEQ ID NO: 26 from U.S. Pat. No. 6,051,686.
[25] Incorporating SEQ ID NO: 28 from U.S. Pat. No. 6,051,686.
[26] Incorporating SEQ ID NO: 29 from U.S. Pat. No. 6,051,686.
[27] Incorporating SEQ ID NO: 30 from U.S. Pat. No. 6,051,686.
[28] Incorporating SEQ ID NO: 26 from U.S. Pat. No. 6,051,686
[29] Incorporating SEQ ID NO: 5 from U.S. Pat. No. 6,051,686.
[30] Based on SEQ ID NOS: 8, 9 from U.S. Pat. No. 6,051,686
[31] Incorporating SEQ ID NO: 10 from U.S. Pat. No. 6,051,686
[32] Incorporating SEQ ID NO: 11 from U.S. Pat. No. 6,051,686
[33] Incorporating SEQ ID NO: 12 from U.S. Pat. No. 6,051,686
[34] Incorporating SEQ ID NO: 12 from U.S. Pat. No. 6,051,686
[35] Incorporating SEQ ID NO: 14 from U.S. Pat. No. 6,051,686
[36] Incorporating SEQ ID NO: 15 from U.S. Pat. No. 6,051,686
[37] Incorporating SEQ ID NO: 16 from U.S. Pat. No. 6,051,686
[38] Incorporating SEQ ID NO: 17 and 18 from U.S. Pat. No. 6,051,686
[39] Incorporating SEQ ID NO: 19 from U.S. Pat. No. 6,051,686
[40] Incorporating SEQ ID NO: 20 from U.S. Pat. No. 6,051,686
[41] Incorporating SEQ ID NO: 21 from U.S. Pat. No. 6,051,686
[42] Incorporating SEQ ID NO: 22 from U.S. Pat. No. 6,051,686
[43] Modified from SEQ ID NO: 23 from U.S. Pat. No. 6,051,686
[44] Modified from SEQ ID NO: 24 from U.S. Pat. No. 6,051,686

Another useful PTH/PTHrP modulating domain has the sequence of the peptide known as TIP39:

SLALADDAAFRERARLLAALERRHWLNSYMHKLLVLDAP
(SEQ ID NO: 160)

TIP39 is described by Usdin et al. (1999), *Nature Neurosci.* 2(11): 941–3; Usdin et al. (1996), *Endocrinology* 137(10): 4285–97; Usdin et al. (1995), *J. Biol. Chem.* 270(26): 15455–8; Usdin et al. (1999), *Endocrinol.* 140(7): 3363–71.

Additional useful PTH/PTHrP modulating domain sequences may result from conservative and/or non-conservative modifications of the amino acid sequences of SEQ ID NOS: 3, 4, 5, TIP39, or the sequences listed in Tables 1 and 2.

Conservative modifications will produce peptides having functional and chemical characteristics similar to those of the PTH or PTHrP peptide from which such modifications are made. In contrast, substantial modifications in the functional and/or chemical characteristics of the peptides may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, *Acta Physiol. Scand. Suppl.* 643:55–67; Sasaki et al., 1998, *Adv. Biophys.* 35:1–24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formulae) described herein. Exemplary amino acid substitutions are set forth in Table 3.

TABLE 3

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |

TABLE 3-continued

Amino Acid Substitutions

| Original Residues | Exemplary Substitutions | Preferred Substitutions |
|---|---|---|
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

As noted in the foregoing section "Definition of Terms," naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157: 105–131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in the foregoing sequences using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a peptide to similar peptides. With such a comparison, one can identify residues and portions of the molecules that are conserved among similar polypeptides. It will be appreciated that changes in areas of a peptide that are not conserved relative to such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4): 422–427 (1996), Chou et al., *Biochemistry*, 13(2): 222–245 (1974); Chou et al.

Biochemistry, 113(2): 211–222 (1974); Chou et al., Adv. Enzymol. Relat. Areas Mol. Biol., 47: 45–148 (1978); Chou et al., Ann. Rev. Biochem., 47: 251–276 and Chou et al., Biophys. J., 26: 367–384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1): 244–247 (1999). It has been suggested (Brenner et al. Curr. Op. Struct. Biol., 7(3): 369–376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3): 377–87 (1997); Sippl et al., Structure, 4(1): 15–9 (1996)), "profile analysis" (Bowie et al., Science, 253: 164–170 (1991); Gribskov et al., Meth. Enzym., 183: 146–159 (1990); Gribskov et al., Proc. Nat. Acad. Sci., 84(13): 4355–8 (1987)), and "evolutionary linkage" (See Home, supra, and Brenner, supra).

Vehicles. This invention requires the presence of at least one vehicle ($F^1$) attached to a peptide through the C-terminus or a sidechain of one of the amino acid residues. Multiple vehicles may also be used; e.g., an Fc at the C-terminus and a PEG group at a sidechain.

An Fc domain is the preferred vehicle. The Fc domain may be fused to the C terminus of the peptides.

As noted above, Fc variants are suitable vehicles within the scope of this invention. A native Fc may be extensively modified to form an Fc variant in accordance with this invention, provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 2 or delete or substitute the cysteine residues at positions 7 and 10 of SEQ ID NO: 2. Even when cysteine residues are removed, the single chain Fc domains can still form a dimeric Fc domain that is held together non-covalently.
2. A native Fc is modified to make it more compatible with a selected host cell. For example, one may remove the PA sequence near the N-terminus of a typical native Fc, which may be recognized by a digestive enzyme in E. coli such as proline iminopeptidase. One may also add an N-terminal methionine residue, especially when the molecule is expressed recombinantly in a bacterial cell such as E. coli. The Fc domain of SEQ ID NO: 2 is one such Fc variant.
3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.
4. One or more glycosylation sites are removed. Residues that are typically glycosylated (e.g., asparagine) may confer cytolytic response. Such residues may be deleted or substituted with unglycosylated residues (e.g., alanine).
5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.
6. Sites are removed that affect binding to Fc receptors other than a salvage receptor. A native Fc may have sites for interaction with certain white blood cells that are not required for the fusion molecules of the present invention and so may be removed.
7. The ADCC site is removed. ADCC sites are known in the art; see, for example, Molec. Immunol. 29 (5): 633–9 (1992) with regard to ADCC sites in IgG1. These sites, as well, are not required for the fusion molecules of the present invention and so may be removed.
8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Preferred Fc variants include the following. In SEQ ID NO: 2 (FIG. 4) the leucine at position 15 may be substituted with glutamate; the glutamate at position 99, with alanine; and the lysines at positions 101 and 103, with alanines. In addition, one or more tyrosine residues can be replaced by phenylalanine residues.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display or RNA-peptide screening for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for $F^1$ and $F^2$. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kD to about 50 kD, most preferably from about 5 kD to about 10 kD. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by α1–6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference in its entirety. Dextran of about 1 kD to about 20 kD is preferred when dextran is used as a vehicle in accordance with the present invention.

Linkers. Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly (Gly)$_4$, (Gly)$_5$), poly(Gly-Ala), and polyalanines. Other specific examples of linkers are:

```
(Gly)3Lys(Gly)4         (SEQ ID NO: 6);
(Gly)3AsnGlySer(Gly)2   (SEQ ID NO: 7);
(Gly)3Cys(Gly)4         (SEQ ID NO: 8); and
GlyProAsnGlyGly         (SEQ ID NO: 9).
```

To explain the above nomenclature, for example, (Gly)$_3$Lys(Gly)$_4$ means Gly-Gly-Gly-Lys-Gly-Gly-Gly-Gly (SEQ ID NO: 6). Combinations of Gly and Ala are also preferred. The linkers shown here are exemplary; linkers within the scope of this invention may be much longer and may include other residues.

Non-peptide linkers are also possible. For example, alkyl linkers such as —NH—(CH$_2$)$_s$—C(O)—, wherein s=2–20 could be used. These alkyl linkers may further be substituted by any non-sterically hindering group such as lower alkyl (e.g., C$_1$–C$_6$) lower acyl, halogen (e.g., Cl, Br), CN, NH$_2$, phenyl, etc. An exemplary non-peptide linker is a PEG linker,

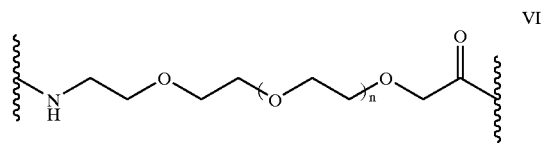

VI wherein n is such that the linker has a molecular weight of 100 to 5000 kD, preferably 100 to 500 kD. The peptide linkers may be altered to form derivatives in the same manner as described above.

Derivatives. The inventors also contemplate derivatizing the peptide and/or vehicle portion of the compounds. Such derivatives may improve the solubility, absorption, biological half life, and the like of the compounds. The moieties may alternatively eliminate or attenuate any undesirable side-effect of the compounds and the like. Exemplary derivatives include compounds in which:

1. The compound or some portion thereof is cyclic. For example, the peptide portion may be modified to contain two or more Cys residues (e.g., in the linker), which could cyclize by disulfide bond formation.

2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus, as in the molecule shown below.

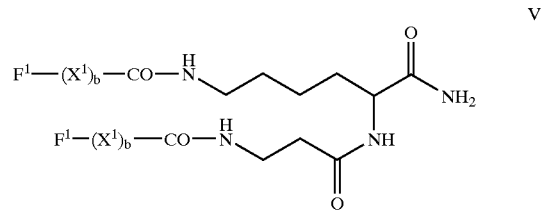

V

3. One or more peptidyl [—C(O)NR—] linkages (bonds) is replaced by a non-peptidyl linkage. Exemplary non-peptidyl linkages are —CH$_2$-carbamate [—CH$_2$—OC(O)NR—], phosphonate, —CH$_2$-sulfonamide [—CH$_2$—S(O)$_2$NR—], urea [—NHC(O)NH—], —CH$_2$-secondary amine, and alkylated peptide [—C(O)NR$^6$— wherein R$^6$ is lower alkyl].

4. The N-terminus is derivatized. Typically, the N-terminus may be acylated or modified to a substituted amine. Exemplary N-terminal derivative groups include —NRR$^1$ (other than —NH$_2$), —NRC(O)R$^1$, —NRC(O)OR$^1$, —NRS(O)$_2$R$^1$, —NHC(O)NHR$^1$, succinimide, or benzyloxycarbonyl-NH— (CBZ-NH—), wherein R and R$^1$ are each independently hydrogen or lower alkyl and wherein the phenyl ring may be substituted with 1 to 3 substituents selected from the group consisting of C$_1$–C$_4$ alkyl, C$_1$–C$_4$ alkoxy, chloro, and bromo.

5. The free C-terminus is derivatized. Typically, the C-terminus is esterified or amidated. Exemplary C-terminal derivative groups include, for example, —C(O)R$^2$ wherein R$^2$ is lower alkoxy or —NR$^3$R$^4$ wherein R$^3$ and R$^4$ are independently hydrogen or C$_1$–C$_8$ alkyl (preferably C$_1$–C$_4$ alkyl).

6. A disulfide bond is replaced with another, preferably more stable, cross-linking moiety (e.g., an alkylene). See, e.g., Bhatnagar et al. (1996), *J. Med. Chem.* 39: 3814–9; Alberts et al. (1993) *Thirteenth Am. Pep. Symp.*, 357–9.

7. One or more individual amino acid residues is modified. Various derivatizing agents are known to react specifically with selected sidechains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R'—N=C=N—R) such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al. (1996), *J. Med. Chem.* 39: 3814–9.

Derivatization with bifunctional agents is useful for cross-linking the peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, *Proteins: Structure and Molecule Properties* (W. H. Freeman & Co., San Francisco), pp. 79–86 (1983).

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Methods of Making

The compounds of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as $E.\ coli$ sp.), yeast (such as Saccharomyces sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), *Chem. Polypeptides*, pp. 335–61 (Katsoyannis and Panayotis eds.); Merrifield (1963), *J. Am. Chem. Soc.* 85: 2149; Davis et al. (1985), *Biochem. Intl.* 10: 394–414; Stewart and Young (1969), *Solid Phase Peptide Synthesis*; U.S. Pat. No. 3,941,763; Finn et al. (1976), *The Proteins* (3rd ed.) 2: 105–253; and Erickson et al. (1976), *The Proteins* (3rd ed.) 2: 257–527. Solid phase synthesis is the preferred technique of making individual peptides since it is the most cost-effective method of making small peptides.

Compounds that contain derivatized peptides or which contain non-peptide groups may be synthesized by well-known organic chemistry techniques.

Uses of the Compounds

The compounds of this invention have pharmacologic activity resulting from their interaction with PTH-1 receptor or PTH-2 receptor. Mannstadt et al. (1999), *Am. J. Physiol.* 277. 5Pt 2. F665-75. PTH and agonists thereof increase bone resorption, increase renal calcium reabsorption, decrease epidermal proliferation, and decrease hair growth. Holick et al. (1994) *Proc. Natl. Sci. USA* 91 (17): 8014–6; Schilli et al. (1997), *J. Invest. Dermatol.* 108(6): 928–32. Thus, antagonists of PTH-1 receptor and/or PTH-2 receptor are useful in treating:

primary and secondary hyperparathyroidism;

hypercalcemia, including hypercalcemia resulting from solid tumors (breast, lung and kidney) and hematologic malignacies (multiple myeloma, lymphoma and leukemia); idiopathic hypercalcemia, and hypercalcemia associated with hyperthyroidism and renal function disorders;

tumor metastases, particularly metastases to bone, and particularly related to breast and prostate cancer;

cachexia and anorexia, particularly as associated with cancer;

osteopenia that is related to or aggravated by aberrant PTH receptor signaling, including various forms of osteoporosis, such as:

primary osteoporosis;

post-menopausal and age-related osteoporosis;

endocrine osteoporosis (hyperthyroidism, hyperparathyroidism, Cushing's syndrome, and acromegaly);

hereditary and congenital forms of osteoporosis (e.g., osteogenesis imperfecta, homocystinuria, Menkes' syndrome, and Riley-Day syndrome);

osteoporosis due to immobilization of extremities;

osteoporosis secondary to other disorders, such as hemochromatosis, hyperprolactinemia, anorexia nervosa, thyrotoxicosis, diabetes mellitus, celiac disease, inflammatory bowel disease, primary biliary cirrhosis, rheumatoid arthritis, ankylosing spondylitis, multiple myeloma, lymphoproliferative diseases, and systemic mastocytosis;

osteoporosis secondary to surgery (e.g., gastrectomy) or to drug therapy, such as chemotherapy, anticonvulsant therapy, immunosuppressive therapy, and anticoagulant therapy;

osteoporosis secondary to glucocorticosteroid treatment for such diseases as rheumatoid arthritis (RA), systemic lupus erythematosus (SLE), asthma, temporal arteritis, vasculitis, chronic obstructive pulmonary disease, polymyalgia rheumatica, polymyositis, chronic interstitial lung disease;

osteoporosis secondary to glucocorticosteroid and/or immunomodulatory treatment to prevent organ rejection following organ transplant such as kidney, liver, lung, heart transplants;

osteoporosis due to submission to microgravity, such as observed during space travel;

osteoporosis associated with malignant disease, such as breast cancer, prostate cancer;

Paget's disease of bone (osteitis deformans) in adults and juveniles;

osteomyelitis, or an infectious lesion in bone, leading to bone loss;

osteopenia following surgery, induced by steroid administration, and associated with disorders of the small and large intestine and with chronic hepatic and renal diseases.

Osteonecrosis, or bone cell death, associated with traumatic injury or nontraumatic necrosis associated with Gaucher's disease, sickle cell anemia, systemic lupus erythematosus, rheumatoid arthritis, periodontal disease, osteolytic metastasis, and other conditions;

alopecia (deficient hair growth or partial or complete hair loss), including androgenic alopecia (male pattern baldness), toxic alopecia, alopecia senilis, alopecia areata, alopecia pelada, and trichotillomania;

and the like.

There are other conditions wherein a patient would benefit from the activity of PTH or PTHrP. For those indications, PTH receptor agonists are useful as a therapeutic treatment. In particular, such indications include fracture repair (including healing of non-union fractures), osteopenia, including various forms of osteoporosis, such as:

primary osteoporosis;

post-menopausal and age-related osteoporosis;

endocrine osteoporosis (hyperthyroidism, Cushing's syndrome, and acromegaly);

hereditary and congenital forms of osteoporosis (e.g., osteogenesis imperfecta, homocystinuria, Menkes' syndrome, and Riley-Day syndrome);

osteoporosis due to immobilization of extremities;

osteoporosis secondary to other disorders, such as hemochromatosis, hyperprolactinemia, anorexia nervosa, thyrotoxicosis, diabetes mellitus, celiac disease, inflammatory bowel disease, primary biliary cirrhosis, rheumatoid arthritis, ankylosing spondylitis, multiple myeloma, lymphoproliferative diseases, and systemic mastocytosis;

osteoporosis secondary to surgery (e.g., gastrectomy) or to drug therapy, such as chemotherapy, anticonvulsant therapy, immunosuppressive therapy, and anticoagulant therapy;

osteoporosis secondary to glucocorticosteroid treatment for diseases such as RA, SLE, asthma, temporal arteritis, vasculitis, chronic obstructive pulmonary disease, polymyalgia rheumatica, polymyositis, chronic interstitial lung disease;

osteoporosis secondary to glucocorticosteroid and/or immunomodulatory treatment to prevent organ rejection following organ transplant such as kidney, liver, lung, heart transplants;

osteoporosis due to submission to microgravity, such as observed during space travel;

osteoporosis associated with malignant disease, such as breast cancer, prostate cancer;

PTH agonists with extended half-life (e.g., those linked to Fc domains) may be used with an inhibitor of bone resorption. Inhibitors of bone resorption include OPG and OPG derivatives, OPG-L (RANKL) antibody, calcitonin (e.g., Miacalcin®, Calcimar®), bisphosphonates (e.g., APD, alendronate, risedronate, etidronate, pamidronate, tiludronate, clodronate, neridronate, ibandronate, zoledronate), estrogens (e.g., Premarin®, Estraderm®, Prempro®, Alora®, Climara®, Vivelle®, Estratab® Ogen®), selective estrogen receptor modulators (e.g., raloxifene, droloxifene, lasofoxifene), tibolone, and the like. Exemplary bone resorption inhibitors are described in WO98/46751 and WO97/23614, which are hereby incorporated by reference in their entirety.

The compounds of this invention may be appropriate as a monotherapy for the treatment of Osteoporosis, and it is possible that the addition of an antiresorptive agent to PTH-Fc treatment will increase both their efficacy and therapeutic window. Both PTH and PTH-Fc cause an increase in both bone formation and bone resorption. The ability of antiresorptives to block the osteoclast response could limit the hypercalcemic effects of PTH-Fc and could also increase bone mass Pharmaceutical Compositions In General. The present invention also provides methods of using pharmaceutical compositions of the inventive compounds. Such pharmaceutical compositions may be for administration for injection, or for oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., *Remington's Pharmaceutical Sciences*, 18th Ed. (1990, Mack Publishing Co., Easton, Pa. 18042) pages 1435–1712 which are herein incorporated by reference in their entirety. The compositions may be prepared in liquid form, or may be in dried powder, such as lyophilized form. Implantable sustained release formulations are also contemplated, as are transdermal formulations.

Twice weekly dosing of the compounds of this invention is superior to daily injection of PTH (1–34) for increasing osteoblast number, bone volume, and bone mineral density in rodents. In adult mice, twice weekly dosing with PTH-(1–34)-Fc caused greater increases in bone density and bone volume compared to daily PTH-(1–34). (See FIG. 10.) In an aged OVX rat model of osteoporosis, twice weekly dosing was able to reverse more than 50% of the bone loss induced by one year of estrogen ablation. The effect seen in the aged rat model was even greater when combined with a bisphosphonate (APD). In rats, a single SC injection of PTH-(1–34)-Fc (340 nmol/kg) caused a hypercalcemic response which persisted for 72 hours (FIG. 8). This duration is concordant with the rate of clearance of PTH-(1–34)-Fc from the serum, and is consistent with an optimal twice-weekly dosing regimen in rats.

The optimal dosing of primates may be less frequent compared to rats or mice. Weekly (or less frequent) dosing may be optimal in primates, based on the observation that the hypercalcemic response of OVX cynomolgus monkeys to a single subcutaneous injection of PTH-(1–34)-Fc (10–34 nmol/kg) persisted for about 168 hours (FIG. 11). This observation suggests that a single subcutaneous dose of PTH-(1–34)-Fc in primates is cleared within about 1 week, which could also represent the maximum dosing frequency required for anabolic effects.

Oral dosage forms. Contemplated for use herein are oral solid dosage forms, which are described generally in Chapter 89 of *Remington's Pharmaceutical Sciences* (1990), 18th Ed., Mack Publishing Co. Easton Pa. 18042, which is herein incorporated by reference in its entirety. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., *Modern Pharmaceutics* (1979), edited by G. S. Banker and C. T. Rhodes, herein incorporated by reference in its entirety. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, *Soluble Polymer-Enzyme Adducts, Enzymes as Drugs* (1981), Hocenberg and Roberts, eds., Wiley-Interscience, New York, N.Y., pp. 367–83; Newmark, et al. (1982), *J. Appl. Biochem.* 4:185–9. Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl] amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary delivery forms. Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., *Pharma. Res.* (1990) 7: 565–9; Adjei et al. (1990), *Internatl. J. Pharmaceutics* 63: 135–44 (leuprolide acetate); Braquet et al. (1989), *J. Cardiovasc. Pharmacol.* 13 (suppl. 5): s. 143–146 (endothelin-1); Hubbard et al. (1989), *Annals Int. Med.* 3: 206–12 (α1- antitrypsin); Smith et al. (1989), *J. Clin. Invest.* 84: 1145–6 (α1-proteinase); Oswein et al. (March 1990), "Aerosolization of Proteins", *Proc. Symp. Resp. Drug Delivery II*, Keystone, Colo. (recombinant human growth hormone); Debs et al. (1988), *J. Immunol.* 140: 3482–8 (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextrin, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextrin. Delivery via transport across other mucous membranes is also contemplated.

Dosages. The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1–1000 micrograms of the inventive compound per kilogram of body weight, preferably 0.1–150 micrograms per kilogram.

Specific preferred embodiments

The inventors have determined preferred structures for the preferred peptides listed in Table 4 below. The symbol "Λ" may be any of the linkers described herein or may simply represent a normal peptide bond (i.e., so that no linker is present). Tandem repeats and linkers are shown separated by dashes for clarity.

TABLE 4

Preferred Embodiments

| Sequence/Structure | Peptide Description | SEQ ID NO: |
| --- | --- | --- |
| SVSEIQLMHNLGKHLNSMERVEWLRKKLQD VHNF-Λ-F$^1$ | PTH (1–34) | 161 |
| SVSEIQLMHNRGKHLNSMERVEWLRKKLQD VHNF-Λ-F$^1$ | (L11R) PTH (1–34) | 162 |
| SVSEIQLMHNKGKHLNSMERVEWLRKKLQD VHNF-Λ-F$^1$ | (L11K) PTH (1–34) | 163 |

TABLE 4-continued

Preferred Embodiments

| Sequence/Structure | Peptide Description | SEQ ID NO: |
|---|---|---|
| SVSEIQLMHNLGKHLNSMRRVEWLRKKLQD VHNF-Λ-F$^1$ | (E19R) PTH (1–34) | 164 |
| SVSEIQLMHNLGKHLNSMERVEWLRKKLQD V-Λ-F$^1$ | PTH (1–31) | 165 |
| SVSEIQLMHNLGKHLNSMERVEWLRKKLQD- Λ-F$^1$ | PTH (1–30) | 166 |
| F$^1$-Λ- SVSEIQLMHNLGKHLNSMERVEWLRKKLQ | PTH (1–29) | 167 |
| F$^1$-Λ- SVSEIQLMHNLGKHLNSMERVEWLRKKL | PTH (1–28) | 168 |
| LLHNLGKSIQDLRRRFFLHHLIAEIHTA- Λ-F$^1$ | (D10N, K11L) PTHrP (7–34) | 169 |
| SLALADDAAFRERARLLAALERRHWLNSY MHKLLVLDAP-Λ-F$^1$ | TIP39 | 170 |

"F$^1$" is an Fc domain as defined previously herein. In addition to those listed in Table 4, the inventors further contemplate heterodimers in which each strand of an Fc dimer is linked to a different peptide sequence; for example, a molecule in which one strand can be described by SEQ ID NO: 166, the other by SEQ ID NO: 170 or an Fc linked with any of the sequences in Tables 1 and 2.

All of the compounds of this invention can be prepared by methods described in PCT appl. no. WO 99/25044.

The invention will now be further described by the following working examples, which are illustrative rather than limiting.

EXAMPLE 1

Bioactivity of AN Fc-Conjugated PTH/PTHrP Receptor (PTH-R1) Agonist [PTH-(1–34)-Fc]

Introduction

Parathyroid hormone [PTH-(1–34) or native PTH-(1–84)] causes increased bone formation and increased bone mass when injected daily. This anabolic response was previously thought to require brief exposure to PTH, which is facilitated by the short half-life (less than 1 h) of PTH. Clinically, the anabolic effect of PTH therapy requires daily SC injection, which is a significant barrier to the widespread use of PTH. Less frequent injections of PTH would be clinically desirable and could be achieved by increasing the in vivo half-life of PTH. Short-term (intermittent) exposure to PTH (<1 h/day) stimulates osteoblastic bone formation, while long-term (continuous) exposure (>2 h/day) stimulates osteoclastic bone resorption (Dobnig et al, *Endocrinology* 138: 4607, 1998). The art suggests that PTH with an extended half-life on its own may increase bone resorption and lead to hypercalcemia. However, it should be possible to prevent PTH-induced osteoclast activity with bone resorption inhibitors. Osteoprotegerin (OPG) may be well suited for this purpose. A single treatment of rats, mice or humans with OPG-Fc causes sustained inhibition of bone resorption, by essentially eradicating the osteoclast population. Co-administration of a potent bone resorption inhibitor, like OPG, may provide greater effect. This regimen would theoretically permit the unopposed stimulation of bone formation by PTH, leading to increased bone mass. It is likely that other bone resorption inhibitors, including bisphosphonates or estrogen, would also inhibit PTH-induced bone resorption and could therefore be used in combination with a long-acting PTH molecule. Towards this goal, we have cloned, expressed and purified human PTH-(1–34)-Fc. Fc conjugation of proteins causes a significant increase in their circulating half life, which may permit injections of PTH-(1–34)-Fc on a schedule similar to or identical to that of OPG-Fc. The benefits of this invention include less frequent injections of PTH, from the current standard of once per day to as infrequently as once per quarter.

Materials, Methods, and Results

Hypercalcemia Assay

We tested the potency and duration of effect of PTH-(1–34)-Fc in a murine hypercalcemia model. Briefly, mice were injected once SC with varying doses of PTH-(1–34) or PTH-(1–34)-Fc, and peripheral blood was collected from the retroorbital sinus for determination of blood ionized calcium. The half-life and the potency of PTH-(1–34)-Fc was greater than that of PTH-(1–34), as evidenced by the sustained hypercalcemic response of mice to the former agent (FIG. 4). Hypercalcemia induced by PTH-(1–34) persisted for 6–24 h, while equimolar doses of PTH-(1–34)-Fc caused more sustained hypercalcemia (48–72 h). This duration of response is consistent with greater half-life of the PTH-(1–34)-Fc construct vs. PTH-(1–34). The potency of PTH-(1–34)-Fc was also significantly greater than that of PTH-(1–34) (FIG. 4). The highest dose of PTH-(1–34)-Fc caused a greater increase in peak ionized calcium levels compared with an equimolar dose of PTH-(1–34). Analysis of the area under the curve (AUC) demonstrated that at the highest dose employed, PTH-(1–34)-Fc caused a 2.6-fold greater hypercalcemic response than did equimolar doses of PTH-(1–34).

Anabolic Assay

Having demonstrated the superior pharmacology and half-life of PTH-(1–34)-Fc over PTH-(1–34), we conducted a pilot study to determine whether PTH-(1–34)-Fc co-treatment with OPG-Fc would increase bone mass. Briefly, 6-month-old male Sprague Dawley (SD) rats were divided into groups of 6. Baseline bone mineral density (BMD) was determined in the third lumbar vertebra (L3) of all rats by dual-energy X-ray absorptiometry (DEXA) (Day 0). Rats were then treated according to the following schedule:

Group 1: Vehicle controls (PBS, injected SC, Days 1, 3, and 5)

Group 2: OPG-Fc, single SC injection (1 mg/kg) on Day 1

Group 3: PTH-(1–34), SC injections on Days 1, 3, and 5, at 20 nMoles PTH/kg/injection. This represents an optimal anabolic PTH regimen.

Group 4: Same as group 3, but with a single OPG-Fc injection on Day 1.

Group 5: Single SC injection of PTH-(1–34)-Fc at 60 nMoles/kg, on Day 1. This represents a molar dose which is equivalent to the total dose of PTH-(1–34) received by group 3, but in a single injection.

Group 6: Same as group 5, but with a single OPG-Fc injection (SC, 1 mg/kg) on Day 1.

DEXA of the lumbar spine was performed again on Day 7 to evaluate changes in BMD. BMD in L3 increased modestly with a single injection of OPG-Fc, or with 3 injections of PTH-(1–34), compared to PBS-treated rats (FIG. 5). PTH-(1–34)+OPG caused a greater increase in BMD than either OPG or PTH-(1–34) alone. As a monotherapy, a single injection of PTH-(1–34)-Fc failed to increase BMD. However, a single injection of PTH-(1–34)-Fc plus a single injection of OPG-Fc caused a significant increase in BMD (FIG. 5). This result provides proof of principle that a PTH construct with extended circulating half life can be combined with a potent antiresorptive, like OPG-Fc, to create an anabolic skeletal response. The anabolic effect of a single treatment with PTH-(1–34)-Fc plus OPG-Fc was greater than that induced by multiple injections of PTH-(1–34), with or without OPG-Fc co-treatment. In conclusion, maximal gains in BMD can be achieved with infrequent injections of PTH-(1–34)-Fc+OPG-Fc, which is a superior treatment regimen compared to PTH-(1–34), which must be injected daily or every second day.

FIG. 5 shows the effect of PTH-Fc+OPG-Fc on bone mineral density (BMD) in the third lumbar vertebra (L3). Normal 6 month old male rats were treated with PTH-Fc or PTH or vehicle by a single SC injection. Some rats also received a single SC injection of OPG. BMD was determined 7 days later by DEXA. Data represent means+SD, N=6 rats/group.

EXAMPLE 2

Bioactivity of an Fc-Conjugated PTH/PTHrP Receptor (PTH-R1) Antagonist ([Asn10,Leu11] PTHrP-(7–34)-Fc)

Introduction

Several disease states are associated with increased circulating levels of PTH or PTHrP. Primary and secondary hyperparathyroidism (PHPT and SHPT, respectively), are associated with increased PTH levels, while humoral hypercalcemia of malignancy (HHM) results in elevated PTHrP levels. Both proteins signal through the common PTH/PTHrP receptor (PTH-R1) to cause increases in bone resorption, renal calcium reabsorption, and renal biosynthesis of vitamin D. While bone resorption inhibitors have variable success in inhibiting osteoclastic bone resorption in these disease states, no therapy currently mitigates the intestinal and renal influence of PTH or PTHrP excess on calcemia. Agents which directly antagonize PTH or PTHrP signaling are therefore likely to have greater efficacy compared to resorption inhibitors.

The most studied antagonists of PTH-R1 signaling are based on amino terminal truncations. PTH-(7–34) peptides are fairly effective PTH-R1 antagonists with very mild agonist activity. Compared to PTH-(7–34), PTHrP-(7–34) peptide has greater affinity for PTH-R1 and as such is a more potent antagonist. However, PTHrP-(7–34) also has greater (but still mild) agonist activity compared to PTH-(7–34) (McKee (1990), *Endocrinol.* 127: 76). The optimal antagonist may combine the weaker agonism of PTH-(7–34) with the stronger antagonism of PTHrP-(7–34). Nutt et al (1990), *Endocrinol.* 127: 491, demonstrates that substituting Asn10 and Leu11 of PTH into the PTHrP sequence (replacing Asp10 and Lys11) results in a peptide ([Asn10,Leu11] PTHrP-(7–34)-Fc) with virtually no agonist activity but with very potent antagonist activity.

Like native PTH, all peptide-based PTH-R1 antagonists share the property of very short circulating half-lives (<1 h). Furthermore, the amino-terminal truncations which are required to remove receptor agonism, also significantly reduce the affinity of these peptides for PTH-R1. These properties limit the clinical potential of conventional peptide antagonists. Fc-conjugation of amino-terminally truncated PTH- or PTHrP peptides should significantly increase their circulating half life, such that continuous antagonism of PTH-R1 might be achieved with sufficient exposure to these Fc-antagonists.

Materials, Methods and Results

We have cloned, expressed and purified [Asn10,Leu11] PTHrP-(7–34)-Fc. We tested the ability of this compound to antagonize both acute and chronic hypercalcemia responses in mice. PTHrP-(1–34) was used as a calcemic agent to evaluate the acute effects of [Asn10,Leu11]PTHrP-(7–34)-Fc. Because PTHrP is the principal mediator of HHM, this study also represents a model for hypercalcemia-inducing tumors. Briefly, blood ionized calcium (BIC) was measured at baseline, and mice were then challenged with vehicle (PBS) or with PTHrP-(1–34) (0.5 mg/kg) by SC injection. Mice were then treated once SC with varying doses of [Asn10,Leu11]PTHrP-(7–34)-Fc, or with vehicle (PBS). In vehicle-treated mice challenged with PTHrP-(1–34), a transient hypercalcemic response was observed. The peak calcemic response occurred at 3 h post challenge, and persisted until at least 6 h post challenge. [Asn10,Leu11]PTHrP-(7–34)-Fc at 10 mg/kg caused a more rapid normalization of PTHrP-induced hypercalcemia compared to vehicle treatment. A dose of 30 mg/kg completely blocked the calcemic response to PTHrP-(1–34) (FIG. 6).

In order to test the ability of [Asn10,Leu11]PTHrP-(7–34)-Fc to antagonize more chronic hypercalcemia, we used PTH-(1–34)-Fc as a long-acting calcemic agent. This study also represents a model for primary and secondary hyperparathyroidism, diseases which are characterized by persistent elevation of PTH levels. In vehicle-treated mice, a single SC injection of PTH-(1–34)-Fc (30 mg/kg) caused a robust hypercalcemic response in normal mice, reaching a level of 2.75 mg/dl at 24 h post challenge (vs. normal control value of 1.35). A single SC injection of [Asn10,Leu11] PTHrP-(7–34)-Fc at 10–100 mg/kg caused a significant decrease in the peak hypercalcemic response to PTH-(1–34)-Fc at 24 h (FIG. 6).

In conclusion, we have demonstrated antagonistic activity of [Asn10,Leu11]PTHrP-(7–34)-Fc, in both acute and chronic animal models of hypercalcemia. These models employed calcemic agents based on both PTH and on PTHrP sequences. These data suggest that [Asn10,Leu11]PTHrP-(7–34)-Fc, as well as other Fc-conjugated PTH-R1 antagonists, may be effective treatment options for hyperparathyroidism, HHM, and other diseases associated with aberrant PTH-R1 signaling.

EXAMPLE 3

Osteogenic Properties of FC-Conjugated and Native C-Terminally Truncated PTH Fragments A. cAMP Assays We tested the relative ability of PTH-Fc constructs to stimulate cAMP accumulation in rat osteoblast-like ROS 17/2.8 cells. Cultures were treated with the phosphodiesterase inhibitor IBMX to promote the accumulation of cAMP. Cultures were then challenged for 15 minutes with either vehicle (PBS), or various PTH constructs. Dose-dependent cAMP accumulation was demonstrated for all fragments. Non-Fc-conjugated PTH-(1–34) was slightly more potent than PTH-(1–31)-Fc and PTH-(1–30)-Fc (FIG. 7). These data demonstrate that Fc-conjugated PTH fragments maintain the ability to activate the AC pathway in osteoblasts.

B. Mouse Bioassay

We then tested the effects of PTH-(1–34), PTH-(1–34)-Fc, PTH-(1–31)-Fc and PTH-(1–30)-Fc in mice. Four week old male mice were injected on days 0, 5, and 10 with vehicle or with PTH fragments, by SC injection. Peripheral blood was obtained for clinical chemistry at 24, 48, and 72 h. Mice were killed on day 15, vertebrae, tibiae and femurs were harvested for histology and one tibia was collected for bone density measurements (peripheral quantitative computed tomography, pQCT). Clinical chemistry endpoints included total serum calcium, serum alkaline phosphatase (AP, a marker of osteoblast activity), and serum tartrate-resistant acid phosphatase (TRAP, a marker of osteoclast activity). For each animal, the ratio of AP:TRAP was calculated as an index of relative osteoblast activity compared to osteoclast activity. A higher AP:TRAP ratio would indicate a potentially more anabolic agent. The relatively high is doses (15-fold greater than optimal anabolic doses) were selected base on previous studies which demonstrated significant changes in clinical chemistry endpoints. It was anticipated that lower doses might be required to demonstrate anabolic effects on bone density, and that antiresorptive co-treatment might also be required to achieve anabolic responses.

The clinical chemistry results are demonstrated in FIG. 8. Serum calcium was not significantly different at 24, 48, or 72 h after injection of 300 nmoles/kg (1.2 mg/kg) of PTH-(1–34). This result is consistent with the short half-life of the non-Fc conjugated peptide, which normally causes a transient (12 h) increase in serum calcium. In contrast, an equimolar dose of PTH-(1–34)-Fc caused a dramatic and sustained increase in serum calcium, which peaked at 24 h. PTH-(1–31)-Fc was a more potent calcemic agent, while PTH-(1–30)-Fc was the least calcemic of the 3 Fc peptides (FIG. 8A). Serum AP (osteoblast marker) was unchanged by PTH-(1–34) administration, but was significantly elevated by 300 nmoles/kg of PTH-(1–34)-Fc and by PTH-(1–31)-Fc at 72 h. PTH-(1–30)-Fc demonstrated the greatest elevation of AP, which peaked 72 h after injection of 1,000 nmoles/kg (FIG. 8B). Serum TRAP (osteoclast marker) was not significantly changed by PTH-(1–34), PTH-(1–34)-Fc, or PTH-(1–30)-Fc, but was dramatically increased by PTH-(1–31)-Fc (FIG. 8C). The calculated AP:TRAP ratios were unchanged by PTH-(1–34), and were increased over time by PTH-(1–34)-Fc. The low dose of PTH-(1–31)-Fc (100 nmoles/kg) increased AP:TRAP, while the high dose (1,000 nmoles/kg) decreased AP:TRAP. The greatest increase in AP:TRAP was realized with PTH-(1–30)-Fc (1,000 nmoles/kg) (FIG. 8D).

Figure 8A:
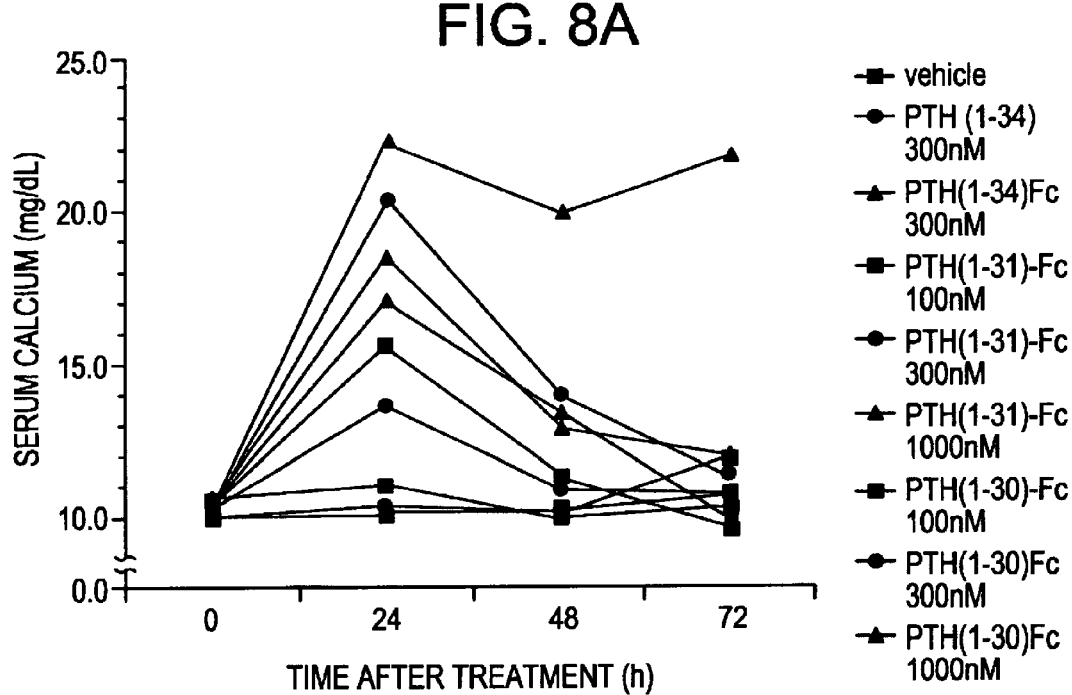
Figure 8B:
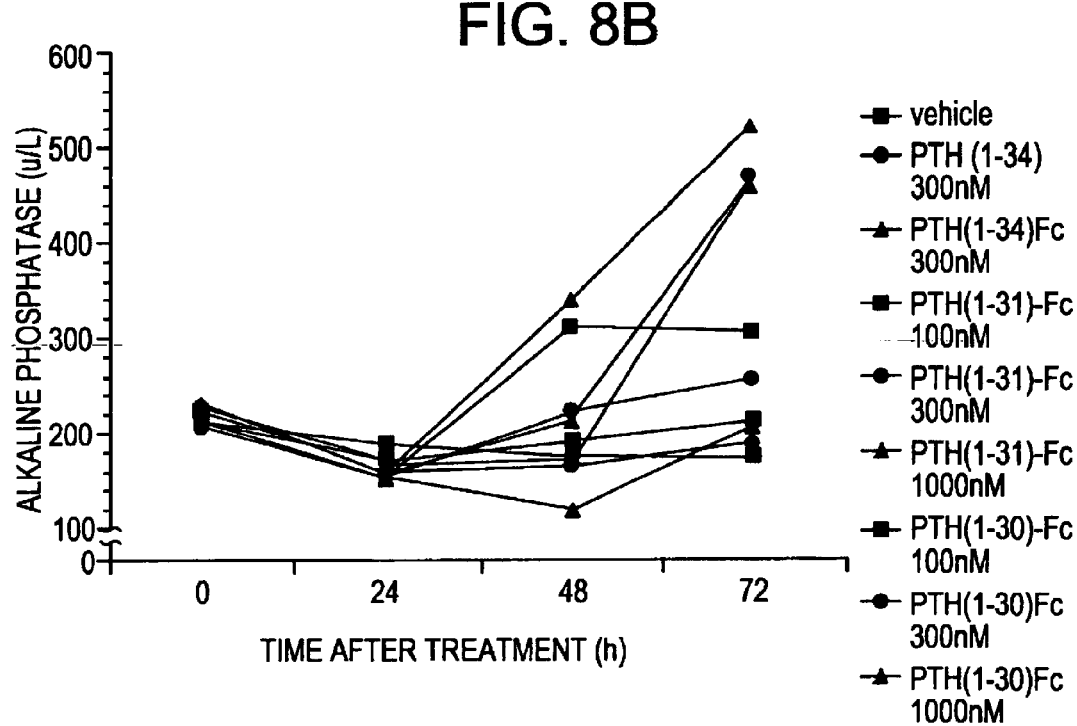
Figure 8C:
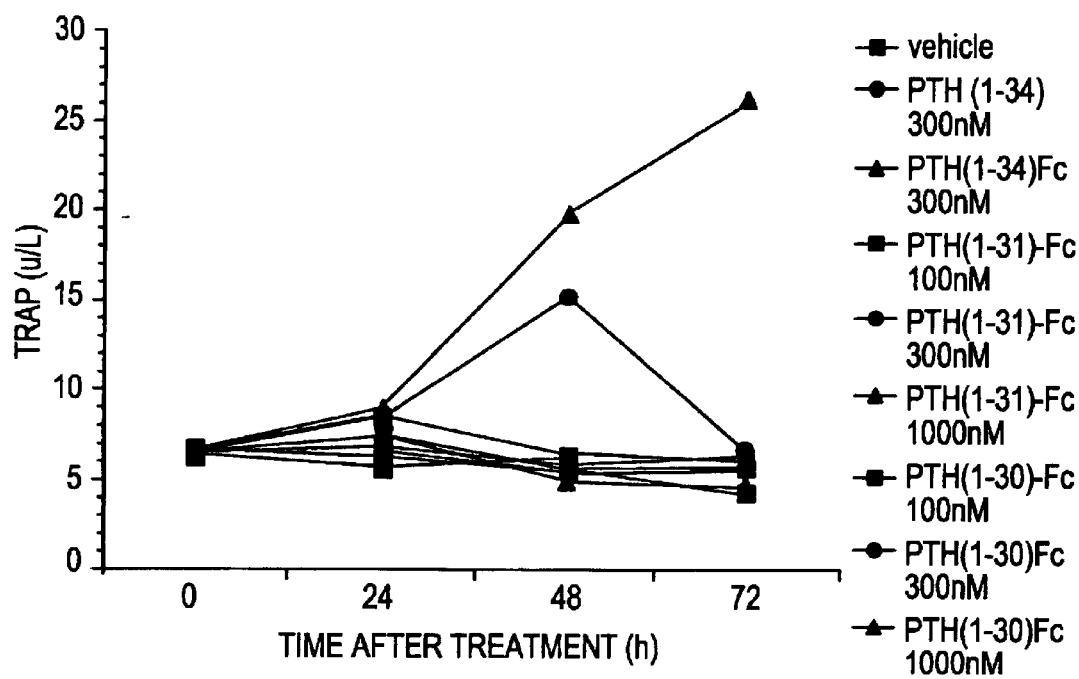
Figure 8D:
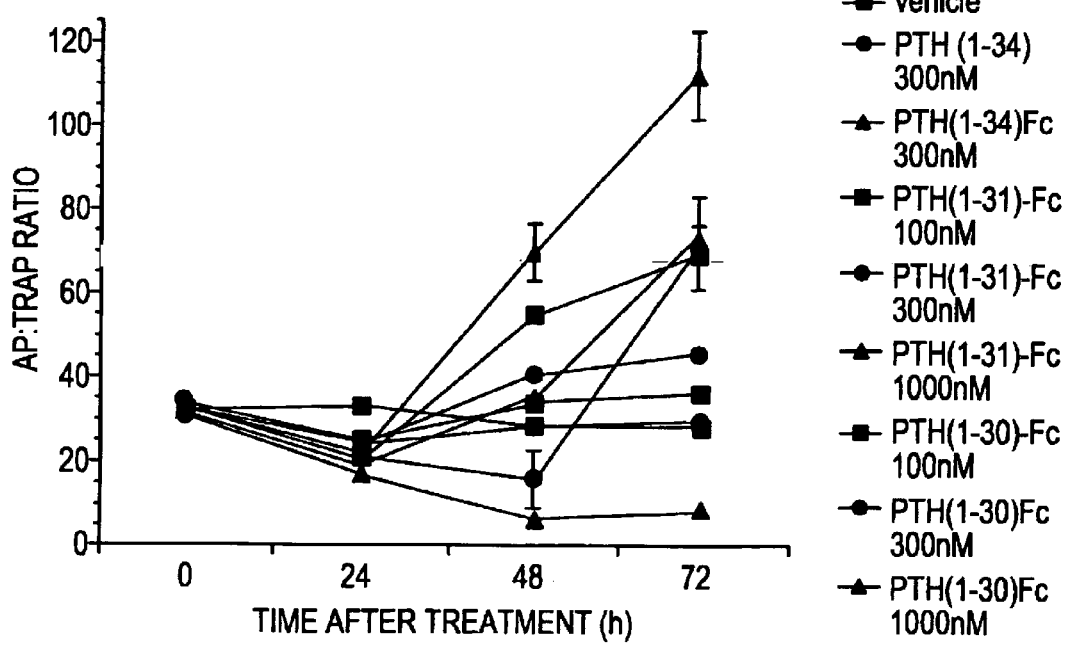

The effects of the various PTH constructs on bone mineral density (proximal tibial metaphysis) are demonstrated in FIG. 9. At the end of the 15-day study, PTH-(1–34) (300 nmoles/kg) was observed to have a modest (non-significant) anabolic effect when injected on day 0, day 5 and day 10. PTH-(1–34)-Fc (300 nmoles/kg) had no effect on bone density, nor did PTH-(1–31)-Fc at 100 nmoles/kg. Higher doses of PTH-(1–31)-Fc (300–1,000 nmoles/kg) caused significant hypercalcemia-related toxicity, and bones were not harvested from these animals for pQCT. PTH-(1–30)-Fc caused the greatest increase in bone density. There was an apparent reverse dose-response, where PTH-(1–30)-Fc at 100 nmoles/kg had the greatest effect and at 1,000 nmoles/kg had the least effect, although at all doses BMD was greater than in controls (FIG. 9). The reverse dose-response was consistent with the notion that doses employed (chosen for clinical chemistry endpoints) were 5–50 fold higher than the optimal anabolic doses. Low doses of PTH (or PTH-Fc) which fail to significantly increase serum calcium are optimal for anabolic effects. See Hock, J. M. (1992), *J. Bone Min. Res.* 7:65–72. In the current study, the treatment regimen with the greatest anabolic effect (PTH-(1–30)-Fc at 100 nmoles/kg) was also the only PTH-Fc treatment which failed to significantly increase serum calcium (FIG. 8A).

These data demonstrate the potential anabolic effects of C-terminally truncated PTH-Fc peptides. The longer half-life conferred by Fc conjugation, combined with the selective stimulation of AC/cAMP by C-terminal truncations, may explain the anabolic effect in the absence of a potent bone resorption inhibitor. It is expected that stepwise C-terminal truncation of PTH-(1–30)-Fc will reveal shorter fragments which maintain or exceed the anabolic profile of PTH-(1–30)-Fc. These fragments may be more selective at stimulating osteoblasts, and may be less calcemic, thus providing a wider therapeutic window for anabolic therapy.

EXAMPLE 4

PTH-Fc Treatment as a Monotherapy

The efficacy of PTH-(1–34)-Fc as a monotherapy was demonstrated in adult mice. Briefly, male BDF1 mice (4 months of age) were treated twice per week by subcutaneous injection with various doses of PTH-(1–34)-Fc or with vehicle (PBS). Other mice were treated daily with SC injections of PTH-(1–34) at a dose of 80 µg/kg/day (20 nmol/kg/day), a treatment regimen which is optimal for increasing bone mass in rodents (M. Gunness-Hey and J. M. Hock, *Metab. Bone Dis. & Rel. Res.* 5:177–181, 1984). After 3 weeks, mice were sacrificed and tibiae were analyzed for bone mineral density (BMD) via pQCT (FIG. 10).

Total tibial BMD and cancelled BMD were both significantly increased by daily PTH-(1–34) injections compared to vehicle-treated controls (FIG. 1, two-way ANOVA, p<0.05). Twice-weekly injections of PTH-(1–34)-Fc caused dose-dependent increases in both total and cancellous BMD which, at the two highest doses (50 and 150 nmol/kg), were significantly greater than the effects of either vehicle or daily PTH-(1–34). Cortical BMD in the tibia was not significantly enhanced by daily PTH-(1–34) treatments. Twice-weekly PTH-(1–34)-Fc caused a dose-dependent increase in cortical BMD which at the highest dose was significantly greater than that observed in mice treated with vehicle or with daily PTH-(1–34) (p<0.05).

Twice-weekly PTH-(1–34)-Fc also effectively increased BMD as a monotherapy in aged ovariectomized (OVX) rats. Sprague Dawley rats were OVX'd at 3 months of age and allowed to lose bone for 11 months. Other rats were sham-operated and treated twice per week with vehicle (PBS). OVX rats were treated twice per week with SC injections of either vehicle or the bisphosphonate APD (pamidronate, 0.5 mg/kg), or with PTH-(1–34)-Fc (50 nmol/kg) or with APD+PTH-(1–34)-Fc. BMD was determined weekly via dual energy X-ray absorptiometry (DEXA). Rats were sacrificed after 4 weeks of treatment. At the start of treatment, OVX rats had significant reductions in BMD at all skeletal sites analyzed, compared to vehicle-treated OVX rats (FIG. 11, p<0.05, 2-way ANOVA). APD alone did not significantly increase BMD at any skeletal site compared to vehicle-treated OVX rats. PTH-(1–34)-Fc alone caused a significant increase in BMD at the femoral metaphysis after 4 weeks of treatment (p<0.05). Treatment of OVX rats with PTH+ABD was associated with an earlier significant increase in BMD at this site (3 weeks). The combination of APD+PTH-(1–34)-Fc also caused significant BMD increases at the lumbar vertebrae and at the femoral metaphysis (p<0.05). PTH-(1–34)-Fc alone caused a mild and transient hypercalcemic response which resolved spontaneously after day 10 despite continued treatments. The co-administration of APD completely blocked the calcemic effect of PTH-(1–34)-Fc.

These data suggest that PTH-(1–34)-Fc is an effective anabolic agent when used as a monotherapy in both adult mice and aged OVX rats. We have also demonstrated that the addition of an antiresorptive agent (APD) to PTH-(1–34)-Fc was associated with similar or more rapid increases in BMD in aged OVX rats. Co-administration of APD also blocked the transient hypercalcemic response produced by PTH-(1–34)-Fc, which suggests that the therapeutic index of PTH-(1–34)-Fc could be significantly improved by co-administering an effective antiresorptive agent.

The invention now being fully described, it will be apparent to one of ordinary skill in the art that many changes and modifications can be made thereto, without departing from the spirit and scope of the invention as set forth herein.

| | Abbreviations |
|---|---|
| AC | adenylate cyclase |
| AP | alkaline phosphatase |
| BMD | bone mineral density |
| cAMP | cyclic adenosine monophosphate |
| DEXA | dual-energy X-ray absorptiometry |
| HHM | humoral hypercalcemia of malignancy |
| OPG | osteoprotegerin |
| OVX | ovariectomized |
| PBS | phosphate-buffered saline |
| pQCT | peripheral quantitative computed tomography |
| PTH | parathyroid hormone |
| PTHrP | parathyroid hormone-related protein |
| TRAP | tartrate-resistant acid phosphatase |

What is claimed is:

1. A polypeptide comprising a parathyroid hormone (PTH) peptide and a Fc domain, wherein said Fc domain is covalently attached to the C-terminus of said PTH peptide.

2. The polypeptide of claim 1 further comprising a linker attaching said Fc domain to said PTH peptide.

3. The polypeptide of claim 1, wherein said Fc domain is an IgG Fc domain.

4. The polypeptide of claim 1, wherein said Fc domain is an IgG1 Fc domain.

5. The polypeptide of claim 1, wherein said Fc domain comprises the sequence of SEQ ID NO: 2.

6. The polypeptide of claim 1, wherein said PTH peptide is PTH-(1–84) or a fragment thereof having PTH activity.

7. The polypeptide of claim 1, wherein said PTH peptide is modified with one or more conservative amino acid substitutions.

8. The polypeptide of claim 6, wherein said PTH peptide is selected from the group consisting of PTH-(7–84), PTH-(1–44), PTH-(1–38), PTH-(2–38), PTH-(1–34), PTH-(7–34), PTH-(1–31), PTH-(1–30), PTH-(7–30), PTH-(1–29), and PTH-(1–28).

9. The polypeptide of claim 1, wherein said PTH peptide is selected from the group consisting of SEQ ID NO: 161, SEQ ID NO: 162, SEQ ID NO: 163, SEQ ID NO: 164, SEQ ID NO: 165, SEQ ID NO: 166, SEQ ID NO: 167, and SEQ ID NO: 168.

10. A polypeptide comprising a parathyroid hormone-related protein (PTHrP) peptide and a Fc domain, wherein said Fc domain is covalently attached to the C-terminus of PTHrP.

11. The polypeptide of claim 10 further comprising a linker attaching said Fc domain to said PTHrP peptide.

12. The polypeptide of claim 10, wherein said Fc domain is an IgG Fc domain.

13. The polypeptide of claim 10, wherein said Fc domain is an IgG1 Fc domain.

14. The polypeptide of claim 10, wherein said Fc domain comprises the sequence of SEQ ID NO: 2.

15. The polypeptide of claim 10, wherein said PTHrP peptide is PTHrP-(1–86) or a fragment thereof having PTHrP activity.

16. The polypeptide of claim 10, wherein said PTHrP peptide is modified with one or more conservative amino acid substitutions.

17. The polypeptide of claim 10, wherein said PTHrP peptide is selected from the group consisting of PTHrP-(1–36), PTHrP-(1–34), PTHrP-(7–34), [Asn10, Leu11] PTHrP-(7–34), PTHrP-(8–34), PTHrP-(1–30), PTHrP-(7–30), and PTHrP-(8–30).

18. The polypeptide of claim 7, wherein said PTHrP peptide is SEQ ID NO: 169.

19. A polypeptide comprising a tuberoinfundibular peptide of 39 residues (TIP39 peptide) and a Fc domain, wherein said Fc domain is covalently attached to the C-terminus of said TIP39 peptide.

20. The polypeptide of claim 19, further comprising a linker attaching said Fc domain to said TIP39 peptide.

21. The polypeptide of claim 20, wherein said Fc domain is an IgG Fc domain.

22. The polypeptide of claim 20, wherein said Fc domain is an IgG1 Fc domain.

23. The polypeptide of claim 20, wherein said Fc domain comprises the sequence of SEQ ID NO: 2.

24. The polypeptide of claim 16, wherein said TIP39 peptide is SEQ ID NO: 170.

* * * * *